(12) United States Patent
Faghih et al.

(10) Patent No.: US 7,741,364 B2
(45) Date of Patent: Jun. 22, 2010

(54) PYRROLE DERIVATIVES AND THEIR METHODS OF USE

(75) Inventors: Ramin Faghih, Lake Forest, IL (US); Gregory A. Gfesser, Lindenhurst, IL (US); Christopher L. Lynch, Trevor, WI (US); Murali Gopalakrishnan, Libertyville, IL (US); Sujatha Gopalakrishnan, Libertyville, IL (US); John Malysz, Round Lake, IL (US); Earl J. Gubbins, Libertyville, IL (US); Rachid El Kouhen, Libertyville, IL (US); Jinhe Li, Long Grove, IL (US)

(73) Assignee: Abbott Laboratories, Abbott Park, IL (US)

( * ) Notice: Subject to any disclaimer, the term of this patent is extended or adjusted under 35 U.S.C. 154(b) by 74 days.

(21) Appl. No.: 11/769,395

(22) Filed: Jun. 27, 2007

(65) Prior Publication Data

US 2008/0064695 A1 Mar. 13, 2008

Related U.S. Application Data

(60) Provisional application No. 60/816,813, filed on Jun. 27, 2006.

(51) Int. Cl.
*A01N 43/36* (2006.01)
(52) U.S. Cl. .................. 514/428; 514/429; 548/530; 548/537; 548/540
(58) Field of Classification Search ............... 514/428, 514/429; 548/530, 537, 540
See application file for complete search history.

(56) References Cited

U.S. PATENT DOCUMENTS

| 2005/0065178 A1 | 3/2005 | Basha et al. |
| 2005/0137204 A1 | 6/2005 | Ji et al. |
| 2005/0245531 A1 | 11/2005 | Ji et al. |

FOREIGN PATENT DOCUMENTS

| EP | 0 799 823 | 8/1997 |
| JP | 11-180871 | 6/1999 |
| WO | 01/47880 | 5/2001 |
| WO | 2004/029053 | 8/2004 |

OTHER PUBLICATIONS

Jordan, V. C. Nature Reviews: Drug Discovery, 2, 2003, p. 205.*
Dörwald, F. Zaragoza. Side Reactions in Organic Synthesis: A Guide to Successful Synthesis Design, Weinheim: WILEY-VCH Verlag GmbH & Co. KGaA, 2005, Preface.*
Wolff, Manfred E. "Burger's Medicinal Chemistry, 5ed, Part I", John Wiley & Sons, 1995, pp. 975-977.*
Banker et al, "Modern Pharmaceutics, 3ed.", Marcel Dekker, New York, 1996, pp. 451 and 596.*
Adler, L.E., et al., "Schizophrenia, Sensory Gating, and Nicotinic Receptors", *Schizophrenia Bull.*, 24:189-202 (1998).
Albuquerque, E.X., et al., "Modulation of Nicotinic Receptor Activity in the Central Nervous System: A Novel Approach to the Treatment of Alzheimer Disease",*Alz. Dis. & Assoc. Disord.*, 15(Suppl. 1):S19-S25 (2001).
Alkondon, M. & Albuquerque, E.X., "The nicotinic acetylcholine receptor subtypes and their function in the hippocampus and cerebral cortex", *Prog. In Br. Es.*, 145:109-120 (2004).
Cordero-Erausquin, M. & Changeux, J-P., "Tonic nicotinic modulation of serotoninergic transmission in the spinal cord", *PNAS*, 98(5):2803-2807 (2001).
Couturier, S., et al., "A neuronal Nicotinic Acetylcholine Receptor Subunit (α7) Is Developmentally Regulated and Forms a Homo-Oligomeric Channel Blocked by α-BTX", *Neuron*, 5:847-856 (1990).
D'Andrea, M.R. & Nagele, R.G., "Targeting the Alpha 7 Nicotinic Acetylcholine Receptor to Reduce Amyloid Accumulation in Alzheimer's Disease Pyramidal Neurons", *Curr. Pharm. Des.*, 12:677-684 (2006).
Dajas-Bailador, F. & Wonnacott, S., "Nicotinic acetylcholine receptors and the regulation of neuronal signaling", *Trends in Pharm. Sci.*, 26(6):317-324 (2004).
Demirayak, S., et al., "Synthesis and cytotoxic and analgesic activities of some 1, 5-diaryl-3-ethoycarbonylpyrrole derivatives", *J. of Enz. Inhib. & Medic. Chem.*, 21(1):113-118 (2006).
Friedman, J.I., et al., "A Double Blind Placebo Controlled Trial of Donepezil Adjunctive Treatment to Risperidone for the Cognitive Impairment of Schizophreniz",*Biol. Psych.*, 51:349-357 (2002).
Gotti, C., et al., "Brain Neuronal Nicotinic Receptors as New Targets for Drug Discovery", *Curr. Pharm Des.*, 12:407-428 (2006).
Hajós, M., et al., "The Selective α7 Nicotinic Acetylcholine Receptor Agonist PNU-282987 [N-[(3R)-1-Azabicyclo[2.2.2]oct-3-yl]-4-chlorobenzamide Hydrochloride] Enhances GABAergic Synaptic Activity in Brain Slices and Restores Auditory Gating Deficits in Anesthetized Rats",*J. of Pharm. & Exp. Ther.*, 312(3):1213-1222 (2005).
Heeschen, C., et al., "Nicotine stimulates angiogenesis and promotes tumor growth and atherosclerosis", *Nature Med.*, 7(7):833-839 (2001).
Heeschen, C., et al., "A novel angiogenic pathway mediated by non-neuronal nicotinic acetylcholine receptors",*J. of Clin. Invest*, 110(4):527-536 (2002).
Hevers, W. & Lüddens, H., "The Diversity of GABA Receptors", *Molec. Neurobiol*, 18:35-86 (1998).
Higuchi, T. & Stella. V., "Pro-drugs as Novel Delivery Systems", vol. 14 of the A.C.S. Symposium Series, (1975).
Hogg, R.C., et al., "Nicotinic acetylcholine receptors: from structure to brain function", *Rev. Physiol. Biochem. Pharmacol.*, 147:1-46 (2003).

(Continued)

*Primary Examiner*—Kamal A Saeed
*Assistant Examiner*—Valerie Rodriguez-Garcia
(74) *Attorney, Agent, or Firm*—Antonia M. Holland

(57) ABSTRACT

The invention relates to a series of substituted pyrrole derivatives, compositions comprising the same, and methods of treating conditions and disorders using such compounds and compositions.

7 Claims, 4 Drawing Sheets

OTHER PUBLICATIONS

Hunter. B.E., et al., "A novel nicotinic agonist facilitates induction of long-term potentiation in the rat hippocampus". *Neurosci. Ltrs.*, 168:130-134 (1994).

Hurst, R.S., et al., "A Novel Positive Allosteric Modulator of the α7 Neuronal Nicotinic Acetylcholine Receptor: In Vitro and In Vivo Characterization",*J. of Neurosci.*, 26(17):4396-4405 (2005).

Jonnala, R.R. & Buccalusco, J.J., "Relationship Between the Increased Cell Surface α7 Nicotinic Receptor Expression and Neuroprotection Induced by Several Nicotinic Receptor Agonists",*J. of Neurosci. Res.*, 66:565-572 (2001).

Keller, J.J., et al, "Performance of α7 nicotinic receptor null mutants is impaired in appetitive learning measured in a signaled nose poke task", *Behav. Br. Res.*, 162:143-152 (2005).

Kihara, T., et al., "α7 Nicotinic Receptor Transduces Signals to Phosphatidylinositol 3-Kinase to Block A β-Amyloid-induced Neurotoxicity",*J. Of. Biol. Chem.*, 276(17)1:13541-13546 (2001).

Leonard, S., et al., "Smoking and schizophrenia: abnormal nicotinic receptor expression", *Eur. J. of Pharm.*,393:237-242(2000).

Levin, E.D., "Nicotinic Receptor Subtypes and Cognitive Function",*J. Neurobiol.*, 53:633-640 (2002).

Liu. Q-s., et al., "β-Amyloid peptide blocks the response of α7-containing nicotinic receptors on hippocampal neurons", *PNAS*, 98(8):4734-4739 (2001).

Martin, L.F., et al., "Alpha-7 nicotinic receptor agaonists: potential new candidates for the treatment of schizophrenia". *Psychopharm.*, 174:54-64 (2004).

Paterson, D. & Nordberg, A., "Neuronal nicotinic receptors in the human brain", *Prog. In Neurobiol.*, 61:75-111 (2000).

Pichat, P., et al., "SSR180711, a novel selective alpha7 nicotinic receptor partial agaonist: (II) efficacy in experimental models predictive of activity against cognitive symptoms of schizophrenia",*Soc. For Neurosci.*, Abstr. #583.3 (2004).

Prescott, D.M., "Methods in Cell Biology", *Academic Press*, vol. XIV:Table of Contents (1976).

Roche, ed., E.B., "Bioreversible Carriers in Drug Design", *Amer. Pharm. Assoc. & Perg Press*, Tble of Cont.,(1987).

Rowley, M., et al., "Current and Novel Approaches to the Drug Treatment of Schizophrenia", *J. of Medic. Chem.*, 44(4):477-501 (2001).

Shimohama, S., et al., "Nicotinic α7 receptors protect against glutamate neurotixicity and neuronal ischemic damage",*Brain Res.*, 779:359-363 (1998).

Son, J.-H., & Meizel, S., "Evidence Suggesting That the Mouse Sperm Acrosome Reaction Initiated by the Zona Pellucida Involves an α7 Nicotinic Acetylcholine Receptor", *Biol of Reprod.*, 68:1348-1353 (2003).

Stevens, K.E., e al., "Selective $\alpha_7$-nicotinic agonists normalize inhibition of auditory response in DBA mice", *Psychopharm.*, 136:320-327 (1998).

Ulloa, L., "The Vagus Nerve and the Nicotinic Anti-Inflammatory Pathway",*Nature Rev.*, 4(8):673-684 (2005).

Van Kampen, M., et al., "AR-17779 improves social recognition in rats by activation of nicotinic $\alpha_7$ receptors", *Psychopharm.*, 172:375-383 (2004).

Wang, H., et al. "Nicotinic acetylcholine receptor α7 subunit is an essential regulator of inflammation", *Nature*, 421:384-388 (2003).

* cited by examiner

PYRROLE DERIVATIVES AND THEIR METHODS OF USE

This application claims the benefit of U.S. Provisional Patent Application No. 60/816,813, filed Jun. 27, 2006, which is herein incorporated by reference in its entirety.

BACKGROUND OF THE INVENTION

1. Technical Field

The invention relates to pyrrole derivatives, compositions comprising such compounds, and methods of treating conditions and disorders using such compounds and compositions.

2. Description of Related Technology

Neuronal nicotinic acetylcholine receptors (nAChRs) are neurotransmitter receptors that are widely distributed throughout the central nervous system (CNS) and the peripheral nervous system (PNS) and are widely understood to play an important role in regulating CNS function. Primarily, nAChRs play a significant part of regulating the release of many neurotransmitters, for example acetylcholine (ACh), norepinephrine, dopamine, serotonin, and GABA, among others. Consequently, nAChRs mediate a wide range of physiological effects.

Twelve protein subunits of neuronal nicotinic receptors have been reported to date (Paterson, D. and Nordberg, A.: Neuronal nicotinic receptors in the human brain. Prog. Neurobiol. 2000; 61:75-111. Hogg, R. C., Raggenbass, M. and Bertrand, D.: Nicotinic acetylcholine receptors: From structure to brain function, Rev. Physiol., Biochem Pharmacol. 2003; 147: 1-46). These subunits are identified as $\alpha 2$, $\alpha 3$, $\alpha 4$, $\alpha 5$, $\alpha 6$, $\alpha 7$, $\alpha 8$, $\alpha 9$, $\alpha 10$; $\beta 2$, $\beta 3$, and $\beta 4$. Of these subunits, nine subunits, $\alpha 2$ through $\alpha 7$ and $\beta 2$ through $\beta 4$, prominently exist in the mammalian brain. Multiple functionally distinct nAChR complexes also exist, for example five $\alpha 7$ subunits can form a receptor as a homomeric functional pentamer or combinations of different subunits can complex together as in case of $\alpha 4 \beta 2$ and $\alpha 3 \beta 4$ receptors. In the mammalian brain, $\alpha 4 \beta 2$ and $\alpha 7$ nAChRs are prominently found.

The role of $\alpha 7$ nAChR in neuronal signaling in the CNS also has been actively investigated. (Couturier, S., Bertrand, D., Matter, J. M., Hernandez, M. C., Bertrand, S., Millar, N., Valera, S., Barkas, T., Ballivet, M. A. Neuronal nicotinic acetylcholine receptor subunit (alpha 7) is developmentally regulated and forms a homo-oligomeric channel blocked by alpha-BTX. Neuron 1990; 5: 847-56). The $\alpha 7$ nAChRs have been demonstrated to regulate interneuron excitability, modulate the release of excitatory and inhibitory neurotransmitters, and lead to neuroprotective effects in experimental in vitro models of cellular damage (Alkondon, M., Albuquerque, E. X. The nicotinic acetylcholine receptor subtypes and their function in the hippocampus and cerebral cortex. Prog. Brain Res. 2004; 145:109-20). Also, studies support that $\alpha 7$ nAChRs are involved in various cognitive functions, including memory, attention, and in schizophrenia (Keller, J. J., Keller, A. B., Bowers, B. J., Wehner, J. M. Performance of alpha7 nicotinic receptor null mutants is impaired in appetitive learning measured in a signaled nose poke task. Behav. Brain Res. 2005; 162:143-52). Biophysical studies have shown that $\alpha 7$ subunits, when expressed in heterologous expression systems, activate and desensitize rapidly, and furthermore, exhibit relatively higher calcium permeability compared to other nAChR combinations (Dajas-Bailador, F., Wonnacott, S. Nicotinic acetylcholine receptors and the regulation of neuronal signalling. Trends Pharmacol. Sci. 2004; 25:317-24).

As such, modulating, or modifying, the activity of $\alpha 7$ nAChRs demonstrates promising potential to prevent or treat a variety of diseases with an underlying pathology that involves cognitive function including, for example, aspects of learning, memory, and attention, as well as schizophrenia and neurodegeneration, such as in Alzheimer's disease and other dementias (reviewed in Gotti, C., Riganti, L., Vailati, S., Clementi, F. Brain neuronal nicotinic receptors as new targets for drug discovery. Curr. Pharm. Des. 2006; 12:407-28). More particularly, the $\alpha 7$ nAChRs have been linked to conditions and disorders related to attention deficit disorder (ADD), attention deficit hyperactivity disorder (ADHD), Alzheimer's disease (AD), mild cognitive impairment (MCI), senile dementia, dementia associated with Lewy bodies, dementia associated with Down's syndrome, AIDS dementia, Pick's disease, as well as cognitive deficits associated with schizophrenia, among other systemic activities (for example, Martin, L. F., Kem, W. R., Freedman, R. Alpha-7 nicotinic receptor agonists: Potential new candidates for the treatment of schizophrenia. Psychopharmacology (Berl). 2004; 174:54-64). The $\alpha 7$ nAChRs have also been reported to slow disease progression in Alzheimer's disease (D'Andrea, M. R., Nagele, R. G. Targeting the alpha 7 nicotinic acetylcholine receptor to reduce amyloid accumulation in Alzheimer's disease pyramidal neurons. Curr. Pharm. Des. 2006; 12:677-84). Additionally, recent studies indicate that $\alpha 7$ nAChRs are involved in non-neuronal cell function, which supports that compounds targeting $\alpha 7$ nAChRs are useful for treating or preventing inflammation and inflammatory pain, septic shock, wound healing, tumor growth inhibition, angiogenesis and skin disorders as well (Ulloa, L. The vagus nerve and the nicotinic anti-inflammatory pathway. Nat. Rev. Drug Discov. 2005; 4: 673-84; Wang, H., Yu, M., Ochani, M., Amella, C. A., Tanovic, M., Susarla, S., Li, J. H., Wang, H., Yang, H., Ulloa, L., Al-Abed, Y., Czura, C. J., Tracey, K. J. Nicotinic acetylcholine receptor alpha7 subunit is an essential regulator of inflammation. Nature 2003; 421:384-8).

One well-known compound, nicotine, is known to provide enhanced attention and cognitive performance, reduced anxiety, enhanced sensory gating, and analgesia and neuroprotective effects when administered. Such effects are mediated by the non-selective effect of nicotine at a variety of nicotinic receptor subtypes. However, nicotine also produces adverse consequences, such as cardiovascular and gastrointestinal problems. Accordingly there is a need to identify subtype-selective compounds that embrace the beneficial effects of nicotine, or a nAChR ligand, while eliminating or decreasing adverse effects.

Examples of reported nAChR ligands are $\alpha 7$ nAChR agonists, such as PNU-282987 (Hajos, M., Hurst, R. S., Hoffmann, W. E., Krause, M., Wall, T. M., Higdon, N. R., Groppi, V. E. The selective alpha7 nicotinic acetylcholine receptor agonist PNU-282987 [N-[(3R)-1-azabicyclo[2.2.2]oct-3-yl]-4-chlorobenzamide hydrochloride] enhances GABAergic synaptic activity in brain slices and restores auditory gating deficits in anesthetized rats. J. Pharmacol. Exp. Ther. 2005; 312:1213-22). Another compound is SSR180711A (Pichat, P., Bergins, O. E., Terranova, J., Santucci, V., Gueudet, C., Francon, D., Voltz, C., Steinberg, R., Griebel, G., Scatton, B., Avenet, P., Oury-Donat, F., Soubri, P. (2004) SSR180711A, a novel selective alpha7 nicotinic receptor partial agonist III effects in models predictive of therapeutic activity on cognitive symptoms of schizophrenia. Society for Neuroscience Abstract number 583.3). Yet another compound, AR-R17779 (Van Kampen, M., Selbach, K., Schneider, R., Schiegel, E., Boess, F., Schreiber, R. AR-R17779 improves social recognition in rats by activation of nicotinic alpha7 receptors. Psychopharmacology (Berl) 2004; 172:375-83), has been reported to improve performance in rats in social recognition, water maze performance, or inhibitory avoidance models of cognitive domains. AR-R17779 also reportedly facilitates the induction of hippocampal long term potentiation (LTP), a proposed cellular model for learning and memory, in rats (Hunter, B. E., de Fiebre, C. M., Papke, R. L., Kem, W. R., Meyer, E. M. A novel nicotinic agonist facilitates induction of long-term potentiation in the rat hippocampus. Neurosci. Lett. 1994; 168:130-134).

Despite the beneficial effects of nAChR ligands, it remains uncertain whether chronic treatment with agonists affecting nAChRs may provide suboptimal benefit due to sustained activation and desensitization of the nAChR. In contrast to agonists, administering a nicotinic positive allosteric modulator can reinforce endogenous cholinergic transmission without directly stimulating the target receptor (Albuquerque, E. X., Santos, M. D., Alkondon, M., Pereira, E. F., Maelicke, A. Modulation of nicotinic receptor activity in the central nervous system: A novel approach to the treatment of Alzheimer disease. Alzheimer Dis. Assoc. Disord. 2001; 15 Suppl 1:S19-25). Accordingly, it would be beneficial to target α7 nAChR function by enhancing effects of the endogenous neurotransmitter acetylcholine via positive allosteric modulators that can reinforce the endogenous cholinergic neurotransmission (ACh) without directly activating α7 nAChRs like agonists. Indeed, allosteric modulators for enhancing channel activity have been proven clinically successful for $GABA_A$ receptors where benzodiazepines, barbiturates, and neurosteroids behave as allosteric positive modulators acting at distinct sites (Hevers, W., Luddens, H.: The diversity of GABAA receptors. Pharmacological and electrophysiological properties of GABAA channel subtypes. Mol. Neurobiol. 1998; 18:35-86).

To date, only a few nAChR allosteric modulators are known, including: 5-hydroxyindole (5-HI), ivermectin, galantamine, bovine serum albumin, and SLURP-1, a peptide derived from acetylcholinesterase (AChE). Recently, genistein, a kinase inhibitor was reported to increase α7 responses, and PNU-120596, a urea analog, was reported to increase the potency and maximal efficacy of ACh as well as improve auditory gating deficits induced by amphetamine in rats (Hurst, R. S., Hajos, M., Raggenbass, M., Wall, T. M., Higdon, N. R., Lawson, J. A., Rutherford-Root, K. L., Berkenpas, M. B., Hoffmann, W. E., Piotrowski, D. W., Groppi, V. E., Allaman, G., Ogier, R., Bertrand, S., Bertrand, D., Arneric, S. P. A novel positive allosteric modulator of the alpha7 neuronal nicotinic acetylcholine receptor: in vitro and in vivo characterization. J. Neurosci. 2005; 25:4396-405). However, positive allosteric modulator compounds presently known generally demonstrate weak activity, have a range of non-specific effects, or can only achieve limited access to the central nervous system where α7 nAChRs are abundantly expressed.

Accordingly, it would be beneficial to identify and provide new positive allosteric modulator compounds and compositions for treating or preventing conditions associated with α7 nAChRs. It would further be particularly beneficial if such compounds can provide improved efficacy of treatment while reducing adverse effects associated with compounds targeting neuronal nicotinic receptors, for example by selectively modulating α7 nAChRs.

BRIEF DESCRIPTION OF THE DRAWINGS

FIG. 1 demonstrates that when an α7 nAChR positive allosteric modulator and a known α7 nAChR agonist are applied together in the assay, a positive calcium response is triggered.

In FIG. 2, the Y-axis is the normalized change in fluorescence and the X-axis represents increasing concentrations of the modulator.

In FIG. 3, the Y-axis is the normalized change in fluorescence and the X-axis represents increasing concentrations of a known agonist.

In FIG. 4, the Y-axis is the normalized change in phospho-ERK1/2 to total ERK ratio and the X-axis represents increasing concentrations of an allosteric modulator.

SUMMARY OF THE INVENTION

Figure 1:
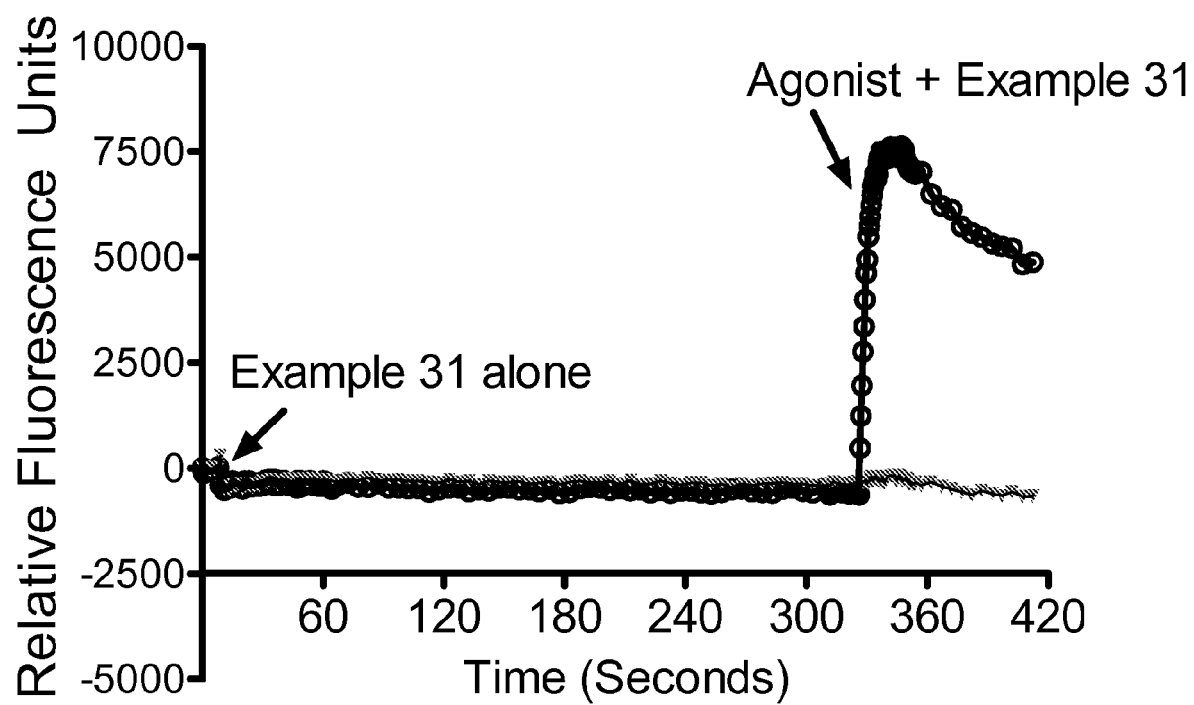
FIG. 1 is a graphical representation of relative fluorescence measured in relative fluorescence units represented as a function of time (in seconds) obtained by assaying a compound, Example 31, in the presence of selective α7 nAChR agonists in cells natively expressing α7 nAChRs, for example the IMR-32 cell line.

The invention relates to compounds, compositions comprising such compounds, and methods of using such compounds, for example for diseases and conditions related to α7 nAChR functions. Such compounds also can be suitable for identifying other useful pharmaceutical compounds.

In one embodiment, the invention relates to compounds of formula (I),

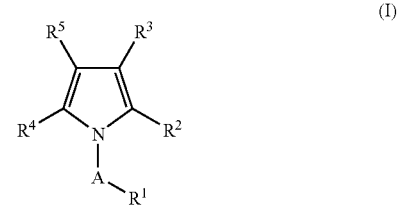

or a pharmaceutically acceptable salts, esters, amides, or prodrugs thereof, wherein:

A is a 5- or 6-membered heteroaryl ring or a 6-membered aryl ring;

$R^1$ is —$SO_2R^{10}$;

$R^2$ is hydrogen, alkyl, aryl, or heteroaryl;

$R^3$ is aryl, heteroaryl, bicyclic heteroaryl, or —$C(O)R^{12}$;

$R^4$ is aryl or —$R^{14}$—$R^{15}$;

$R^5$ is hydrogen, halo, aryl, heteroaryl, bicyclic heteroaryl, —$R^{23}$—$R^{24}$, or —$R^{23}$—$C(O)$—$R^{24}$;

$R^{10}$ is alkyl, —N=CHN(CH$_3$)$_2$, or —NR$^{11a}$R$^{11b}$;

$R^{11a}$ and $R^{11b}$ are independently hydrogen or alkyl; or $R^{11a}$ and $R^{11b}$ taken together with the nitrogen atom to which each is attached form a 4-, 5-, or 6-membered heterocycle;

$R^{12}$ is hydrogen, alkyl, aryl, arylalkyl, cycloalkyl, heterocycle, heteroaryl, heteroarylalkyl, —OR$^{13}$ or —NR$^{16}$R$^{17}$, $R^{13}$ is hydrogen, alkyl or arylalkyl;

$R^{14}$ is aryl;

$R^{15}$ is aryl, heteroaryl, heterocycle or —R$^{21}$—R$^{22}$;

$R^{16}$ and $R^{17}$ are independently hydrogen, alkyl, alkoxy, alkoxyalkyl, aryl, arylalkyl, cycloalkyl, heteroaryl, heteroarylalkyl, heterocycle, heterocyclealkyl, hydroxyalkyl or $R^{18}R^{19}$N-alkyl-;

$R^{18}$ and $R^{19}$ are independently hydrogen or alkyl;

$R^{21}$ is aryl or heteroaryl;

$R^{22}$ is arylalkyl;

$R^{23}$ is aryl; and $R^{24}$ is heteroaryl or heterocycle.

The invention also is directed to the methods of preventing or treating conditions and disorders that are regulated by the nicotinic acetylcholine receptors (nAChR) using compounds of formula (II) or therapeutically acceptable compositions of compounds of formula (II)

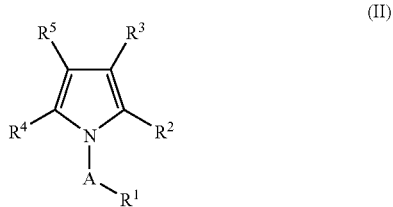

(II)

or a pharmaceutically acceptable salt, ester, amide, or prodrug thereof, wherein:

A is a 5- or 6-membered heteroaryl ring or a 6-membered aryl ring;

$R^1$ is hydrogen, alkyl, alkenyl, alkynyl, halo, haloalkyl, OR$^6$, nitro, —NR$^{8a}$R$^{8b}$, CH$_2$NR$^{8a}$R$^{8b}$, —C(O)OR$^9$, —C(O)R$^{10}$ or —SO$_2$R$^{10}$;

$R^2$ is hydrogen, alkyl, aryl, or heteroaryl;

$R^3$ is hydrogen, alkyl, alkenyl, alkynyl, aryl, halo, haloalkyl, heteroarylbicyclic heteroaryl-C(O)R$^{12}$; —OR$^9$, nitro, or —NR$^{8a}$R$^{8b}$;

$R^4$ is hydrogen, alkyl, aryl or —R$^{14}$—R$^{15}$;

$R^5$ is hydrogen, halo, aryl, heteroaryl, bicyclic heteroaryl, bicyclic heteroaryl, —R$^{23}$—R$^{24}$ or —R$^{23}$—C(O)—R$^{24}$;

$R^6$ at each occurrence is independently hydrogen, alkyl, aryl, or heteroaryl;

$R^{8a}$ and $R^{8b}$ at each occurrence are independently hydrogen, alkyl, aryl, heteroaryl, —C(O)OR$^9$ or —C(O)R$^{10}$;

$R^9$ is hydrogen, alkyl or arylalkyl;

$R^{10}$ is alkyl, —N=CHN(CH$_3$)$_2$, or —NR$^{11a}$R$^{11b}$;

$R^{11a}$ and $R^{11b}$ are independently hydrogen, alkyl, alkylcarbonyl, aryl, heteroaryl or heterocycle; or $R^{11a}$ and $R^{11b}$ taken together with the nitrogen atom to which each is attached form a 4-, 5-, or 6-membered heterocycle;

$R^{12}$ is selected from the group consisting of hydrogen, alkyl, aryl, arylalkyl, cycloalkyl, heterocycle, heteroaryl, heteroarylalkyl, —OR$^{13}$ or —NR$^{16}$R$^{17}$;

$R^{13}$ is hydrogen, alkyl or arylalkyl;

$R^{14}$ is aryl;

$R^{15}$ is aryl, heteroaryl, heterocycle or —R$^{21}$—R$^{22}$;

$R^{16}$ and $R^{17}$ are independently hydrogen, alkyl, alkoxy, alkoxyalkyl, aryl, arylalkyl, cycloalkyl, heteroaryl, heteroarylalkyl, heterocycle, heterocyclealkyl, hydroxyalkyl or $R^{18}R^{19}$N-alkyl-;

$R^{18}$ and $R^{19}$ are independently hydrogen or alkyl;

$R^{21}$ is aryl or heteroaryl;

$R^{22}$ is arylalkyl;

$R^{23}$ is aryl; and $R^{24}$ is heteroaryl or heterocycle.

The invention also is directed to the methods of treating conditions and disorders that are regulated by the nicotinic acetylcholine receptors (nAChR) using compounds of formula (I) or (II) or therapeutically acceptable compositions of compounds of formula (I) or (II).

Such compositions containing compounds of formula (I) or (II) can be administered in accordance with described methods, typically as part of a therapeutic regimen for treatment or prevention of conditions and disorders related to nAChR activity, and more particularly allosteric modulation of nAChR activity.

Compounds of formula (I) or (II) can be used in a method for treating or preventing conditions and disorders related to nAChR modulation in mammals. More particularly, the method is useful for conditions and disorders related to attention deficit disorder (ADD), attention deficit hyperactivity disorder (ADHD), Alzheimer's disease (AD), mild cognitive impairment, senile dementia, AIDS dementia, Pick's Disease, dementia associated with Lewy bodies, dementia associated with Down's syndrome, amyotrophic lateral sclerosis, Huntington's disease, diminished CNS function associated with traumatic brain injury, acute pain, post-surgical pain, chronic pain, inflammation, inflammatory pain, neuropathic pain, infertility, need for new blood vessel growth associated with wound healing, need for new blood vessel growth associated with vascularization of skin grafts and lack of circulation, rheumatoid arthritis, Crohn's disease, ulcerative colitis, inflammatory bowel disease, organ transplant rejection, acute immune disease associated with organ transplantation, chronic immune disease associated with organ transplantation, septic shock, toxic shock syndrome, sepsis syndrome, depression, and rheumatoid spondylitis, and various other conditions modulated by α4β2 nAChRs, α7 nAChRs, or both α4β2 and α7 nAChRs.

In another embodiment, the invention relates to a method of identifying a positive α7 allosteric modulator comprising the steps of allowing a compound to interact with cells or cell lines endogenously expressing α7 nAChRs or cells expressing recombinant α7 nAChRs in a fluorescent medium and measuring changes in such fluorescence. In one aspect, the positive α7 allosteric modulator is identified by measuring changes in fluorescence related to calcium ion flux or cell membrane potential. In another aspect, the positive α7 allosteric modulator identified by measuring the changes in fluorescence related to phosphorylation of ERK.

Another embodiment of the invention relates to a method of assessing or diagnosing conditions or disorders related to α7 receptor activity comprising allowing isotope-labelled forms of compounds of formula (II) to interact with cells expressing endogenous α7 nAChRs or cells expressing recombinant α7 nAChRs and measuring the effects of such isotope-labelled forms of compounds on such cells.

Another method of the invention relates to identifying an α7 nAChR agonist comprising the steps of allowing a compound to interact with cells or cell lines endogenously expressing α7 nAChRs or cells expressing recombinant α7 nAChRs in a fluorescent medium and then measuring changes in such fluorescence.

Accordingly, various aspects of the invention also describe the use of nAChR ligands, and particularly allosteric modulator compounds, to identify other useful target compounds or for treating or preventing, or both, diseases or conditions associated with nAChR function, in cell-based assays, for example in high-throughput format, using cells or tissues that express native α7 receptors for the purpose of identifying novel α7 agonists or α7 allosteric modulators.

The compounds, compositions comprising the compounds, and methods for treating or preventing conditions and disorders by administering the compounds are further described herein.

DETAILED DESCRIPTION OF THE INVENTION

Definition of Terms

Certain terms as used in the specification are intended to refer to the following definitions, as detailed below.

The term "acyl", as used herein, means an alkyl group, as defined herein, appended to the parent molecular moiety through a carbonyl group, as defined herein. Representative examples of acyl include, but are not limited to, acetyl, 1-oxopropyl, 2,2-dimethyl-1-oxopropyl, 1-oxobutyl, and 1-oxopentyl.

The term "acyloxy", as used herein, means an acyl group, as defined herein, appended to the parent molecular moiety through an oxygen atom. Representative examples of acyloxy include, but are not limited to, acetyloxy, propionyloxy, and isobutyryloxy.

The term "alkenyl", as used herein, means a straight or branched chain hydrocarbon containing from 2 to 10 carbons and containing at least one carbon-carbon double bond formed by the removal of two hydrogens. Representative examples of alkenyl include, but are not limited to, ethenyl, 2-propenyl, 2-methyl-2-propenyl, 3-butenyl, 4-pentenyl, 5-hexenyl, 2-heptenyl, 2-methyl-1-heptenyl, and 3-decenyl.

The term "alkoxy", as used herein, means an alkyl group as defined herein, appended to the parent molecular moiety through an oxygen atom. Representative examples of alkoxy include, but are not limited to, methoxy, ethoxy, propoxy, 2-propoxy, butoxy, tert-butoxy, pentyloxy, and hexyloxy.

The term "alkoxyalkoxy", as used herein, means an alkoxy group, as defined herein, appended to the parent molecular moiety through another alkoxy group, as defined herein. Representative examples of alkoxyalkoxy include, but are not limited to, tert-butoxymethoxy, 2-ethoxyethoxy, 2-methoxyethoxy, and methoxymethoxy.

The term "alkoxyalkyl", as used herein, means an alkoxy group, as defined herein, appended to the parent molecular moiety through an alkyl group, as defined herein. Representative examples of alkoxyalkyl include, but are not limited to, tert-butoxymethyl, 2-ethoxyethyl, 2-methoxyethyl, and methoxymethyl.

The term "alkoxycarbonyl", as used herein, means an alkoxy group, as defined herein, appended to the parent molecular moiety through a carbonyl group, represented by —C(O)—, as defined herein. Representative examples of alkoxycarbonyl include, but are not limited to, methoxycarbonyl, ethoxycarbonyl, and tert-butoxycarbonyl.

The term "alkoxyimino", as used herein, means an alkoxy group, as defined herein, appended to the parent molecular moiety through an imino group, as defined herein. Representative examples of alkoxyimino include, but are not limited to, ethoxy(imino)methyl and methoxy(imino)methyl.

The term "alkoxysulfonyl", as used herein, means an alkoxy group, as defined herein, appended to the parent molecular moiety through a sulfonyl group, as defined herein. Representative examples of alkoxysulfonyl include, but are not limited to, methoxysulfonyl, ethoxysulfonyl and propoxysulfonyl.

The term "alkyl", as used herein, means a straight or branched chain hydrocarbon containing from 1 to 6 carbon atoms. Representative examples of alkyl include, but are not limited to, methyl, ethyl, n-propyl, iso-propyl, n-butyl, sec-butyl, iso-butyl, tert-butyl, n-pentyl, isopentyl, neopentyl, and n-hexyl.

The term "alkylcarbonyl", as used herein, means an alkyl group, as defined herein, appended to the parent molecular moiety through a carbonyl group, as defined herein. Representative examples of alkylcarbonyl include, but are not limited to, acetyl, 1-oxopropyl, 2,2-dimethyl-1-oxopropyl, 1-oxobutyl, and 1-oxopentyl.

The term "alkylcarbonyloxy", as used herein, means an alkylcarbonyl group, as defined herein, appended to the parent molecular moiety through an oxygen atom. Representative examples of alkylcarbonyloxy include, but are not limited to, acetyloxy, ethylcarbonyloxy, and tert-butylcarbonyloxy.

The term "alkylsulfonyl", as used herein, means an alkyl group, as defined herein, appended to the parent molecular moiety through a sulfonyl group, as defined herein. Representative examples of alkylsulfonyl include, but are not limited to, methylsulfonyl and ethylsulfonyl.

The term "alkylthio", as used herein, means an alkyl group, as defined herein, appended to the parent molecular moiety through a sulfur atom. Representative examples of alkylthio include, but are not limited, methylthio, ethylthio, tert-butylthio, and hexylthio.

The term "alkynyl", as used herein, means a straight or branched chain hydrocarbon group containing from 2 to 10 carbon atoms and containing at least one carbon-carbon triple bond. Representative examples of alkynyl include, but are not limited, to acetylenyl, 1-propynyl, 2-propynyl, 3-butynyl, 2-pentynyl, and 1-butynyl.

The term "amido", as used herein, means an amino ($H_2N$—), alkylamino (alkylN(H)—), dialkylamino ($alkyl_2N$—), arylamino (arylN(H)—), arylalkylamino (arylalkylN(H)—) or another substituted amine group appended to the parent molecular moiety through a carbonyl group, as defined herein. Representative examples of amido include, but are not limited to, aminocarbonyl, methylaminocarbonyl, dimethylaminocarbonyl, and ethyl methylaminocarbonyl.

The term "aryl", as used herein, means a monocyclic or bicyclic aromatic ring system. Representative examples of aryl include, but are not limited to, phenyl and naphthyl.

The aryl groups of this invention are substituted with 0, 1, 2, 3, 4, or 5 substituents independently selected from acyl, acyloxy, alkenyl, alkoxy, alkoxyalkoxy, alkoxyalkyl, alkoxycarbonyl, alkoxyimino, alkoxysulfonyl, alkyl, alkylcarbonyl, alkylsulfonyl, alkynyl, amino, carboxy, cyano, cyanoalkyl, formyl, haloalkoxy, haloalkyl, halo, hydroxy, hydroxyalkyl, mercapto, nitro, thioalkoxy, —$NR_AR_B$, ($NR_AR_B$)alkyl, ($NR_AR_B$)alkoxy, ($NR_AR_B$)carbonyl, and ($NR_AR_B$)sulfonyl.

The term "arylalkyl" as used herein, means an aryl group, as defined herein, appended to the parent molecular moiety through an alkyl group, as defined herein. Representative examples of arylalkyl include, but are not limited to, benzyl, 2-phenylethyl, 3-phenylpropyl, and 2-naphth-2-ylethyl.

The term "arylsulfonyl", as used herein, means an aryl group, as defined herein, appended to the parent molecular moiety through a sulfonyl group, as defined herein. Representative examples of arylsulfonyl include, but are not limited to, phenylsulfonyl, (methylaminophenyl)sulfonyl, (dimethylaminophenyl)sulfonyl, and (naphthyl)sulfonyl.

The term "carbonyl", as used herein, means a —C(O)— group.

The term "carboxy", as used herein, means a —CO$_2$H group.

The term "cyano", as used herein, means a —CN group.

The term "cycloalkyl" as used herein, means a monocyclic, bicyclic, or tricyclic ring system. Monocyclic ring systems are exemplified by a saturated cyclic hydrocarbon group containing from 3 to 8 carbon atoms. Examples of monocyclic ring systems include cyclopropyl, cyclobutyl, cyclopentyl, cyclohexyl, cycloheptyl, and cyclooctyl. Bicyclic ring systems are exemplified by a bridged monocyclic ring system in which two non-adjacent carbon atoms of the monocyclic ring are linked by an alkylene bridge of between one and three additional carbon atoms. Representative examples of bicyclic ring systems include, but are not limited to, bicyclo[3.1.1]heptane, bicyclo[2.2.1]heptane, bicyclo[2.2.2]octane, bicyclo[3.2.2]nonane, bicyclo[3.3.1]nonane, and bicyclo[4.2.1]nonane. Tricyclic ring systems are exemplified by a bicyclic ring system in which two non-adjacent carbon atoms of the bicyclic ring are linked by a bond or an alkylene bridge of between one and three carbon atoms. Representative examples of tricyclic-ring systems include, but are not limited to, tricyclo[3.3.1.0$^{3,7}$]nonane and tricyclo[3.3.1.1$^{3,7}$]decane (adamantane).

The cycloalkyl groups of the present invention are optionally substituted with 1, 2, 3, 4 or 5 substituents selected from the group consisting of alkenyl, alkoxy, alkoxyalkoxy, alkoxyalkyl, alkoxycarbonyl, alkoxysulfonyl, alkyl, alkylcarbonyl, alkylcarbonyloxy, alkylsulfonyl, alkylthio, alkylthioalkyl, alkynyl, carboxy, cyano, formyl, haloalkoxy, haloalkyl, halogen, hydroxy, hydroxyalkyl, mercapto, oxo, —NZ$_1$Z$_2$, and (NZ$_3$Z$_4$)carbonyl.

The term "formyl", as used herein, means a —C(O)H group.

The term "halo" or "halogen", as used herein, means —Cl, —Br, —I or —F.

The term "haloalkoxy", as used herein, means at least one halogen, as defined herein, appended to the parent molecular moiety through an alkoxy group, as defined herein. Representative examples of haloalkoxy include, but are not limited to, chloromethoxy, 2-fluoroethoxy, trifluoromethoxy, and pentafluoroethoxy.

The term "haloalkyl", as used herein, means at least one halogen, as defined herein, appended to the parent molecular moiety through an alkyl group, as defined herein. Representative examples of haloalkyl include, but are not limited to, chloromethyl, 2-fluoroethyl, trifluoromethyl, pentafluoroethyl, and 2-chloro-3-fluoropentyl.

The term "heteroaryl" means an aromatic five- or six-membered ring containing 1, 2, 3, or 4 heteroatoms independently selected from nitrogen, oxygen, or sulfur. The heteroaryl groups are connected to the parent molecular moiety through a carbon or nitrogen atom. Representative examples of heteroaryl include, but are not limited to, furyl, imidazolyl, isoxazolyl, isothiazolyl, oxadiazolyl, oxazolyl, pyrazinyl, pyrazolyl, pyridazinyl, pyridinyl, pyrimidinyl, pyrrolyl, tetrazolyl, thiadiazolyl, thiazolyl, thienyl, triazinyl, and triazolyl.

The heteroaryl groups of the invention are substituted with 0, 1, 2, or 3 substituents independently selected from alkenyl, alkoxy, alkoxyalkoxy, alkoxyalkyl, alkoxycarbonyl, alkoxysulfonyl, alkyl, alkylcarbonyl, alkylcarbonyloxy, alkylsulfonyl, alkylthio, alkynyl, carboxy, cyano, cyanoalkyl, formyl, haloalkoxy, haloalkyl, halo, hydroxy, hydroxyalkyl, mercapto, nitro, —NR$_A$R$_B$, (NR$_A$R$_B$)alkyl, (NR$_A$R$_B$)alkoxy, (NR$_A$R$_B$)carbonyl, and (NR$_A$R$_B$)sulfonyl.

The term "bicyclic heteroaryl" refers to fused aromatic nine- and ten-membered bicyclic rings containing 1, 2, 3, or 4 heteroatoms independently selected from nitrogen, oxygen, or sulfur, or a tautomer thereof. The bicyclic heteroaryl groups are connected to the parent molecular moiety through a carbon or nitrogen atom. Representative examples of bicyclic heteroaryl rings include, but are not limited to, indolyl, benzodioxolyl, benzothiazolyl, benzofuranyl, isoquinolinyl, and quinolinyl. Bicyclic heteroaryl groups of the invention are substituted with 0, 1, 2, or 3 substituents independently selected from alkenyl, alkoxy, alkoxyalkoxy, alkoxyalkyl, alkoxycarbonyl, alkoxysulfonyl, alkyl, alkylcarbonyl, alkylcarbonyloxy, alkylsulfonyl, alkylthio, alkynyl, carboxy, cyano, cyanoalkyl, formyl, haloalkoxy, haloalkyl, halo, hydroxy, hydroxyalkyl, mercapto, nitro, —NR$_A$R$_B$, (NR$_A$R$_B$)alkyl, (NR$_A$R$_B$)alkoxy, (NR$_A$R$_B$)carbonyl, and (NR$_A$R$_B$)sulfonyl.

The term "heteroarylalkyl" as used herein, means a heteroaryl, as defined herein, appended to the parent molecular moiety through an alkyl group, as defined herein. Representative examples of heteroarylalkyl include, but are not limited to, fur-3-ylmethyl, 1H-imidazol-2-ylmethyl, 1H-imidazol-4-ylmethyl, 1-(pyridin-4-yl)ethyl, pyridin-3-ylmethyl, 6-chloropyridin-3-ylmethyl, pyridin-4-ylmethyl, (6-(trifluoromethyl)pyridin-3-yl)methyl, (6-(cyano)pyridin-3-yl)methyl, (2-(cyano)pyridin-4-yl)methyl, (5-(cyano)pyridin-2-yl)methyl, (2-(chloro)pyridin-4-yl)methyl, pyrimidin-5-ylmethyl, 2-(pyrimidin-2-yl)propyl, thien-2-ylmethyl, and thien-3-ylmethyl.

The term "heterocycle" or "heterocyclic" as used herein, means a monocyclic heterocycle or a bicyclic heterocycle. The monocyclic heterocycle is a 3, 4, 5, 6 or 7 membered ring containing at least one heteroatom independently selected from the group consisting of O, N, and S. The 3 or 4 membered ring contains 1 heteroatom selected from the group consisting of O, N and S. The 5 membered ring contains zero or one double bond and one, two, three or four heteroatoms selected from the group consisting of O, N and S. The 6 or 7 membered ring contains zero, one or two double bonds and one, two, three or four heteroatoms selected from the group consisting of O, N and S. The monocyclic heterocycle is connected to the parent molecular moiety through any carbon atom or any nitrogen atom contained within the monocyclic heterocycle. Representative examples of monocyclic heterocycle include, but are not limited to, azetidinyl, azepanyl, aziridinyl, diazepanyl, 1,3-dioxanyl, 1,3-dioxolanyl, 1,3-dithiolanyl, 1,3-dithianyl, imidazolinyl, imidazolidinyl, isothiazolinyl, isothiazolidinyl, isoxazolinyl, isoxazolidinyl, morpholinyl, oxadiazolinyl, oxadiazolidinyl, oxazolinyl, oxazolidinyl, piperazinyl, piperidinyl, pyranyl, pyrazolinyl, pyrazolidinyl, pyrrolinyl, pyrrolidinyl, tetrahydrofuranyl, tetrahydrothienyl, thiadiazolinyl, thiadiazolidinyl, thiazolinyl, thiazolidinyl, thiomorpholinyl, 1,1-dioxidothiomorpholinyl (thiomorpholine sulfone), thiopyranyl, and trithianyl. The bicyclic heterocycle is a monocyclic heterocycle fused to a phenyl group, or a monocyclic heterocycle fused to a cycloalkyl, or a monocyclic heterocycle fused to a cycloalkenyl, a monocyclic heterocycle fused to a monocyclic heterocycle or a monocyclic heterocycle fused to a monocyclic heteroaryl. The bicyclic heterocycle is connected to the parent molecular moiety through any carbon atom or any nitrogen atom contained within the monocyclic heterocycle. Representative examples of bicyclic heterocycle include, but are not limited to, 1,3-benzodioxolyl, 1,3-benzodithiolyl, 2,3-dihydro-1,4-benzodioxinyl, 2,3-dihydro-1-benzofuranyl, 2,3-dihydro-1-benzothienyl, 2,3-dihydro-1H-indolyl, and 1,2,3,4-tetrahydroquinolinyl.

The heterocycles of this invention are optionally substituted with 1, 2, or 3 substituents independently selected from the group consisting of alkenyl, alkoxy, alkoxyalkoxy, alkoxyalkyl, alkoxycarbonyl, alkoxysulfonyl, alkyl, alkylcarbonyl, alkylcarbonyloxy, alkylsulfonyl, alkylthio, alkynyl, carboxy, cyano, cyanoalkyl, formyl, haloalkoxy, haloalkyl, halo, hydroxy, hydroxyalkyl, mercapto, nitro, $-NR_AR_B$, $(NR_AR_B)$alkyl, $(NR_AR_B)$alkoxy, $(NR_AR_B)$carbonyl, and $(NR_AR_B)$sulfonyl.

The term "heterocyclealkyl" as used herein, means a heterocycle, as defined herein, appended to the parent molecular moiety through an alkyl group, as defined herein.

The term "hydroxy", as used herein, means an —OH group.

The term "hydroxyalkyl", as used herein, means at least one hydroxy group, as defined herein, is appended to the parent molecular moiety through an alkyl group, as defined herein. Representative examples of hydroxyalkyl include, but are not limited to, hydroxymethyl, 2-hydroxyethyl, 3-hydroxypropyl, 2,3-dihydroxypentyl, and 2-ethyl-4-hydroxyheptyl.

The term "mercapto", as used herein, means a —SH group.

The term "nitro", as used herein, means a —NO₂ group.

The term "—$NR_AR_B$", as used herein, means two groups, $R_A$ and $R_B$, which are appended to the parent molecular moiety through a nitrogen atom. $R_A$ and $R_B$ are each independently hydrogen, alkyl, alkylcarbonyl, alkylsulfonyl or formyl. Representative examples of —$NR_AR_B$ include, but are not limited to, amino, methylamino, acetylamino, and acetylmethylamino.

The term "$(NR_AR_B)$alkyl", as used herein, means a —$NR_AR_B$ group, as defined herein, appended to the parent molecular moiety through an alkyl group, as defined herein. Representative examples of $(NR_AR_B)$alkyl include, but are not limited to, (amino)methyl, (dimethylamino)methyl, and (ethylamino)methyl.

The term "$(NR_AR_B)$alkoxy", as used herein, means a —$NR_AR_B$ group, as defined herein, appended to the parent molecular moiety through an alkoxy group, as defined herein. Representative examples of $(NR_AR_B)$alkoxy include, but are not limited to, (amino)methoxy, (dimethylamino)methoxy, and (diethylamino)ethoxy.

The term "$(NR_AR_B)$carbonyl", as used herein, means a —$NR_AR_B$ group, as defined herein, appended to the parent molecular moiety through a carbonyl group, as defined herein. Representative examples of $(NR_AR_B)$carbonyl include, but are not limited to, aminocarbonyl, (methylamino)carbonyl, (dimethylamino)carbonyl, and (ethylmethylamino)carbonyl.

The term "$(NR_AR_B)$sulfonyl", as used herein, means a —$NR_AR_B$ group, as defined herein, appended to the parent molecular moiety through a sulfonyl group, as defined herein. Representative examples of $(NR_AR_B)$sulfonyl include, but are not limited to, aminosulfonyl, (methylamino)sulfonyl, (dimethylamino)sulfonyl, and (ethylmethylamino)sulfonyl.

The term "$NZ_1Z_2$" as used herein, means two groups, $Z_1$ and $Z_2$, which are appended to the parent molecular moiety through a nitrogen atom. $Z_1$ and $Z_2$ are each independently selected from the group consisting of hydrogen, alkyl, alkylcarbonyl, alkoxycarbonyl, aryl, arylalkyl, formyl and $(NZ_5Z_6)$carbonyl. In certain instances within the present invention, $Z_1$ and $Z_2$ taken together with the nitrogen atom to which they are attached form a heterocyclic ring. Representative examples of $NZ_1Z_2$ include, but are not limited to, amino, methylamino, acetylamino, acetylmethylamino, phenylamino, benzylamino, azetidinyl, pyrrolidinyl and piperidinyl.

The term "$NZ_3Z_4$" as used herein, means two groups, $Z_3$ and $Z_4$, which are appended to the parent molecular moiety through a nitrogen atom. $Z_3$ and $Z_4$ are each independently selected from the group consisting of hydrogen, alkyl, aryl and arylalkyl. Representative examples of $NZ_3Z_4$ include, but are not limited to, amino, methylamino, phenylamino and benzylamino.

The term "sulfonyl", as used herein, means a —$S(O)_2$— group.

The term "thioalkoxy", as used herein, means an alkyl group, as defined herein, appended to the parent molecular moiety through a sulfur atom. Representative examples of thioalkoxy include, but are no limited to, methylthio, ethylthio, and propylthio The term "Positive Allosteric Modulator" as used herein, means a compound that enhances activity of an endogenous, or naturally occurring, ligand, such as but not limited to ACh, or an exogenously administered agonist.

Although typically it may be recognized that an asterisk is used to indicate that the exact subunit composition of a receptor is uncertain, for example, α3β4* indicates a receptor that contains the α3 and β4 proteins in combination with other subunits, the term α7 as used herein is intended to include receptors wherein the exact subunit composition is both certain and uncertain. For example, as used herein α7 includes homomeric $(α7)_5$ receptors and α7* receptors, which denote a nAChR containing at least one α7 subunit.

Compounds of the Invention

Compounds of the invention can have the formula (I) as described above. More particularly, compounds of formula (I) can include, but are not limited to, compounds wherein A is phenyl; and $R^2$ is alkyl. More particularly, compounds of formula (I) exist wherein A is phenyl; and $R^2$ is methyl.

In addition, compounds of formula (I) exist, wherein $R^1$ is —$SO_2$alkyl, —$SO_2NH_2$, or $SO_2NR^{11a}R^{11b}$, wherein $R^{11a}$ and $R^{11b}$ taken together with the nitrogen atom to which each is attached form a 4-, 5-, or 6-membered heterocycle.

More particularly, compounds of formula (I) exist wherein A is phenyl; $R^2$ is methyl; $R^1$ is —$SO_2$alkyl, —$SO_2NH_2$, or —$SO_2NR^{11a}R^{11b}$ wherein $R^{11a}$ and $R^{11b}$ taken together with the nitrogen atom to which each is attached form a 4-, 5-, or 6-membered heterocycle; $R^4$ is aryl, wherein aryl is optionally substituted with 1, 2 or 3 substitutents selected from the group consisting of alkyl, alkylcarbonyl, alkoxy, alkylsulfonyl, cyano, halo, haloalkyl, nitro, and —$NR_AR_B$, wherein $R_A$ and $R_B$ are independently hydrogen, alkyl, alkylcarbonyl and alkylsulfonyl.

Specific embodiments contemplated as part of the invention include, but are not limited to, compounds of formula (I), as defined, wherein:

ethyl 1-[4-(aminosulfonyl)phenyl]-5-(4-bromophenyl)-2-methyl-1H-pyrrole-3-carboxylate;

ethyl 5-(4-bromophenyl)-2-methyl-1-[3-(methylsulfonyl)phenyl]-1H-pyrrole-3-carboxylate;

5-biphenyl-4-yl-2-methyl-1-(4-sulfamoyl-phenyl)-1H-pyrrole-3-carboxylic acid ethyl ester;

5-(4'-chloro-biphenyl-4-yl)-2-methyl-1-(4-sulfamoyl-phenyl)-1H-pyrrole-3-carboxylic acid ethyl ester;

5-(4'-methoxy-biphenyl-4-yl)-2-methyl-1-(4-sulfamoyl-phenyl)-1H-pyrrole-3-carboxylic acid ethyl ester;

5-(3',5'-difluoro-biphenyl-4-yl)-2-methyl-1-(4-sulfamoyl-phenyl)-1H-pyrrole-3-carboxylic acid ethyl ester;

5-(3'-cyano-biphenyl-4-yl)-2-methyl-1-(4-sulfamoyl-phenyl)-1H-pyrrole-3-carboxylic acid ethyl ester;
5-(4-furan-3-yl-phenyl)-2-methyl-1-(4-sulfamoyl-phenyl)-1H-pyrrole-3-carboxylic acid ethyl ester;
2-methyl-1-(4-sulfamoyl-phenyl)-5-(4-thiophen-3-yl-phenyl)-1H-pyrrole-3-carboxylic acid ethyl ester;
2-methyl-5-(4-pyridin-4-yl-phenyl)-1-(4-sulfamoyl-phenyl)-1H-pyrrole-3-carboxylic acid ethyl ester;
1-(3-methanesulfanyl-phenyl)-2-methyl-5-[4-(1-methyl-1H-pyrazol-4-yl)-phenyl]-1H-pyrrole-3-carboxylic acid ethyl ester;
5-[4-(1-benzyl-1H-pyrazol-4-yl)-phenyl]-1-(3-methanesulfonyl-phenyl)-2-methyl-1H-pyrrole-3-carboxylic acid ethyl ester;
1-(3-methanesulfonyl-phenyl)-2-methyl-5-(4-pyridin-4-yl-phenyl)-1H-pyrrole-3-carboxylic acid ethyl ester;
5-[4-(5-cyano-pyridin-3-yl)-phenyl]-1-(3-methanesulfonyl-phenyl)-2-methyl-1H-pyrrole-3-carboxylic acid ethyl ester;
5-(4'-chloro-biphenyl-4-yl)-1-(3-methanesulfonyl-phenyl)-2-methyl-1H-pyrrole-3-carboxylic acid ethyl ester;
1-(3-methansulfonyl-phenyl)-5-(4'-methoxy-biphenyl-4-yl)-2-methyl-1H-pyrrole-3-carboxylic acid ethyl ester;
5-(4'-cyano-biphenyl-4-yl)-1-(3-methanesulfonyl-phenyl)-2-methyl-1H-pyrrole-3-carboxylic acid ethyl ester;
1-(3-methanesulfonyl-phenyl)-2-methyl-5-(4-morpholin-4-yl-phenyl)-1H-pyrrole-3-carboxylic acid ethyl ester;
2-methyl-5-(4-pentyl-phenyl)-1-(4-sulfamoyl-phenyl)-1H-pyrrole-3-carboxylic acid ethyl ester;
5-(4-chloro-phenyl)-2-methyl-1-[4-(piperidine-1-sulfonyl)-phenyl]-1H-pyrrole-3-carboxylic acid ethyl ester;
5-(4-chloro-phenyl)-1-(4-dimethylsulfamoyl-phenyl)-2-methyl-1H-pyrrole-3-carboxylic acid ethyl ester;
5-(4-chloro-phenyl)-2-methyl-1-[3-(pyrrolidine-1-sulfonyl)-phenyl]-1H-pyrrole-3-carboxylic acid ethyl ester;
ethyl 5-(4-chlorophenyl)-2-methyl-1-[3-(piperidin-1-ylsulfonyl)phenyl]-1H-pyrrole-3-carboxylate;
ethyl 1-[3-(aminosulfonyl)phenyl]-5-(4-chlorophenyl)-2-methyl-1H-pyrrole-3-carboxylate;
5-(4-chloro-phenyl)-2-methyl-1-(4-sulfamoyl-phenyl)-1H-pyrrole-3-carboxylic acid ethyl ester;
sodium 5-(4-chloro-phenyl)-2-methyl-1-(4-sulfamoyl-phenyl)-1H-pyrrole-3-carboxylate;
5-(4-chloro-phenyl)-1-[4-(dimethylaminomethylene-sulfamoyl)-phenyl]-2-methyl-1H-pyrrole-3-carboxylic acid N-methoxy-N-methyl-amide;
4-[5-(4-chloro-phenyl)-2-methyl-3-propionyl-pyrrol-1-yl]-benzenesulfonamide;
4-[5-(4-chloro-phenyl)-3-isobutyryl-2-methyl-pyrrol-1-yl]-benzenesulfonamide;
4-[5-(4-chloro-phenyl)-3-cyclopropanecarbonyl-2-methyl-pyrrol-1-yl]-benzenesulfonamide;
4-[5-(4-chloro-phenyl)-2-methyl-3-(4-methyl-benzoyl)-pyrrol-1-yl]-benzenesulfonamide;
4-[3-(4-chloro-3-methyl-benzoyl)-5-(4-chloro-phenyl)-2-methyl-pyrrol-1-yl]-benzenesulfonamide;
4-[3-(4-chloro-benzoyl)-5-(4-chloro-phenyl)-2-methyl-pyrrol-1-yl]-benzenesulfonamide;
4-[5-(4-chloro-phenyl)-3-(5-fluoro-2-methoxy-benzoyl)-2-methyl-pyrrol-1-yl]-benzenesulfonamide;
5-(4-chloro-phenyl)-1-(3-methanesulfonyl-phenyl)-2-methyl-1H-pyrrol-1-yl]-benzenesulfonamide;
5-(4-chloro-phenyl)-1-(3-methanesulfonyl-phenyl)-2-methyl-1H-pyrrole-3-carboxylic acid;
5-(4-chloro-phenyl)-1-(3-methanesulfonyl-phenyl)-2-methyl-1H-pyrrole-3-carboxylic acid methoxy-methyl amide;
1-[5-(4-chloro-phenyl)-1-(3-methanesulfonyl-phenyl)-2-methyl-1H-pyrrol-3-yl]propan-1-one;
ethyl 2-methyl-1-(3-(methylsulfonyl)phenyl)-5-phenyl-1H-pyrrole-3-carboxylate;
5-(4-chloro-phenyl)-1-(3-ethanesulfonyl-phenyl)-2-methyl-1H-pyrrole-3-carboxylic acid ethyl ester;
1-(3-ethanesulfonyl-phenyl)-2-methyl-5-phenyl-1H-pyrrole-3-carboxylic acid ethyl ester;
2-methyl-5-phenyl-1-[3-(propane-2-sulfonyl)-phenyl]-1H-pyrrole-3-carboxylic acid ethyl ester;
5-(4-chloro-phenyl)-1-(3-methanesulfonyl-phenyl)-2-phenyl-1H-pyrrole-3-carboxylic acid ethyl ester;
5-(4-chloro-phenyl)-2-(4-fluoro-phenyl)-1-(3-methanesulfonyl-phenyl)-1H-pyrrole-3-carboxylic acid ethyl ester;
5-(4-chloro-phenyl)-2-(2-fluoro-phenyl)-1-(3-methanesulfonyl-phenyl)-1H-pyrrole-3-carboxylic acid ethyl ester;
5-(4-chloro-phenyl)-2-ethyl-1-(3-methanesulfonyl-phenyl)-1H-pyrrole-3-carboxylic acid ethyl ester;
5-(4-chloro-phenyl)-1-(3-methanesulfonyl-phenyl)-2-methyl-1H-pyrrole-3-carboxylic acid benzyl ester;
5-(4-chloro-phenyl)-1-(4-methanesulfonyl-phenyl)-2-methyl-1H-pyrrole-3-carboxaldehyde;
4-[5-(4-chloro-phenyl)-3-(4-hydroxymethyl-phenyl)-2-methyl-pyrrol-1-yl]-benzenesulfonamide;
4-[3-benzofuran-2-yl-5-(4-chloro-phenyl)-2-methyl-pyrrol-1-yl]-benzenesulfonamide;
5-(4-chloro-phenyl)-4-iodo-2-methyl-1-(4-sulfamoyl-phenyl)-1H-pyrrole-3-carboxylic acid ethyl ester;
5-(4-chloro-phenyl)-4-(4-hydroxymethyl-phenyl)-2-methyl-1-(4-sulfamoyl-phenyl)-1H-pyrrole-3-carboxylic acid ethyl ester;
5-(4-chloro-phenyl)-2-methyl-4-phenyl-1-(4-sulfamoyl-phenyl)-1H-pyrrole-3-carboxylic acid ethyl ester;
4-(3-amino-phenyl)-5-(4-chloro-phenyl)-2-methyl-1-(4-sulfamoyl-phenyl)-1H-pyrrole-3-carboxylic acid ethyl ester;
5-(4-chloro-phenyl)-4-(3-hydroxy-phenyl)-2-methyl-1-(4-sulfamoyl-phenyl)-1H-pyrrole-3-carboxylic acid ethyl ester;
5-(4-chloro-phenyl)-4-(3-methoxy-phenyl)-2-methyl-1-(4-sulfamoyl-phenyl)-1H-pyrrole-3-carboxylic acid ethyl ester;
5-(4-chloro-phenyl)-4-(3-chloro-phenyl)-2-methyl-1-(4-sulfamoyl-phenyl)-1H-pyrrole-3-carboxylic acid ethyl ester;
4,5-bis-(4-chloro-phenyl)-2-methyl-1-(4-sulfamoyl-phenyl)-1H-pyrrole-3-carboxylic acid ethyl ester;
5-(4-chloro-phenyl)-4-(3-cyano-phenyl)-2-methyl-1-(4-sulfamoyl-phenyl)-1H-pyrrole-3-carboxylic acid ethyl ester;
5-(4-chloro-phenyl)-4-(4-cyano-phenyl)-2-methyl-1-(4-sulfamoyl-phenyl)-1H-pyrrole-3-carboxylic acid ethyl ester;
4-(3-acetyl-phenyl)-5-(4-chloro-phenyl)-2-methyl-1-(4-sulfamoyl-phenyl)-1H-pyrrole-3-carboxylic acid ethyl ester;
4-benzo[1,3]dioxol-5-yl-5-(4-chloro-phenyl)-2-methyl-1-(4-sulfamoyl-phenyl)-1H-pyrrole-3-carboxylic acid ethyl ester;
5-(4-chloro-phenyl)-4-(3,5-dichloro-phenyl)-2-methyl-1-(4-sulfamoyl-phenyl)-1H-pyrrole-3-carboxylic acid ethyl ester;
5-(4-chloro-phenyl)-4-furan-3-yl-2-methyl-1-(4-sulfamoyl-phenyl)-1H-pyrrole-3-carboxylic acid ethyl ester;
5-(4-chloro-phenyl)-2-methyl-1-(4-sulfamoyl-phenyl)-4-thiophen-3-yl-1H-pyrrole-3-carboxylic acid ethyl ester;
4-benzofuran-2-yl-5-(4-chloro-phenyl)-2-methyl-1-(4-sulfamoyl-phenyl)-1H-pyrrole-3-carboxylic acid ethyl ester;
5-(4-chloro-phenyl)-2-methyl-4-(3-nitro-phenyl)-1-(4-sulfamoyl-phenyl)-1H-pyrrole-3-carboxylic acid ethyl ester;

5-(4-chloro-phenyl)-2-methyl-4-naphthalen-2-yl-1-(4-sulfamoyl-phenyl)-1H-pyrrole-3-carboxylic acid ethyl ester;

5-(4-chloro-phenyl)-4-(4-methanesulfonyl-phenyl)-2-methyl-1-(4-sulfamoyl-phenyl)-1H-pyrrole-3-carboxylic acid ethyl ester;

5-(4-chloro-phenyl)-4-(1H-indol-4-yl)-2-methyl-1-(4-sulfamoyl-phenyl)-1H-pyrrole-3-carboxylic acid ethyl ester;

5-(4-chloro-phenyl)-4-(3-dimethylamino-phenyl)-2-methyl-1-(4-sulfamoyl-phenyl)-1H-pyrrole-3-carboxylic acid ethyl ester;

4-(4-acetylamino-phenyl)-5-(4-chloro-phenyl)-2-methyl-1-(4-sulfamoyl-phenyl)-1H-pyrrole-3-carboxylic acid ethyl ester;

5-(4-chloro-phenyl)-4-(4-methanesulfonylamino-phenyl)-2-methyl-1-(4-sulfamoyl-phenyl)-1H-pyrrole-3-carboxylic acid ethyl ester;

5-(4-chloro-phenyl)-4-(3-dimethylcarbamoyl-phenyl)-2-methyl-1-(4-sulfamoyl-phenyl)-1H-pyrrole-3-carboxylic acid ethyl ester;

5-(4-chloro-phenyl)-4-(4-cyanomethyl-phenyl)-2-methyl-1-(4-sulfamoyl-phenyl)-1H-pyrrole-3-carboxylic acid ethyl ester;

5-(4-chloro-phenyl)-2-methyl-4-[3-(4-methyl-piperazine-1-carbonyl)-phenyl]-1-(4-sulfamoyl-phenyl)-1H-pyrrole-3-carboxylic acid ethyl ester;

5-(4-chloro-phenyl)-2-methyl-1-(4-sulfamoyl-phenyl)-1H-pyrrole-3-carboxylic acid isopropylamide;

5-(4-chloro-phenyl)-2-methyl-1-(4-sulfamoyl-phenyl)-1H-pyrrole-3-carboxylic acid butylamide;

5-(4-chloro-phenyl)-2-methyl-1-(4-sulfamoyl-phenyl)-1H-pyrrole-3-carboxylic acid (2-methoxy-ethyl)-amide;

5-(4-chloro-phenyl)-2-methyl-1-(4-sulfamoyl-phenyl)-1H-pyrrole-3-carboxylic acid-(3-propoxy-propyl)-amide;

5-(4-chloro-phenyl)-2-methyl-1-(4-sulfamoyl-phenyl)-1H-pyrrole-3-carboxylic acid-(R)-(tetrahydro-furan-2-ylmethyl)-amide;

5-(4-chloro-phenyl)-2-methyl-1-(4-sulfamoyl-phenyl)-1H-pyrrole-3-carboxylic acid (tetrahydro-furan-3-ylmethyl)-amide;

5-(4-chloro-phenyl)-2-methyl-1-(4-sulfamoyl-phenyl)-1H-pyrrole-3-carboxylic acid cyclobutylamide;

5-(4-chloro-phenyl)-2-methyl-1-(4-sulfamoyl-phenyl)-1H-pyrrole-3-carboxylic acid dimethylamide;

5-(4-chloro-phenyl)-2-methyl-1-(4-sulfamoyl-phenyl)-1H-pyrrole-3-carboxylic acid ethyl-methyl-amide;

5-(4-chloro-phenyl)-2-methyl-1-(4-sulfamoyl-phenyl)-1H-pyrrole-3-carboxylic acid isopropyl-methyl-amide;

4-[5-(4-chloro-phenyl)-2-methyl-3-(pyrrolidine-1-carbonyl)-pyrrol-1-yl]-benzenesulfonamide;

4-[5-(4-chloro-phenyl)-2-methyl-3-(piperidine-1-carbonyl)-pyrrol-1-yl]-benzenesulfonamide;

5-(4-chloro-phenyl)-2-methyl-1-(4-sulfamoyl-phenyl)-1H-pyrrole-3-carboxylic acid-(2-methoxy-ethyl)-methyl-amide;

5-(4-chloro-phenyl)-2-methyl-1-(4-sulfamoyl-phenyl)-1H-pyrrole-3-carboxylic acid-bis-(2-methoxy-ethyl)-amide;

4-[5-(4-chloro-phenyl)-2-methyl-3-(morpholine-4-carbonyl)-pyrrol-1-yl]-benzenesulfonamide;

5-(4-chloro-phenyl)-2-methyl-1-(4-sulfamoyl-phenyl)-1H-pyrrole-3-carboxylic acid benzylamide;

5-(4-chloro-phenyl)-2-methyl-1-(4-sulfamoyl-phenyl)-1H-pyrrole-3-carboxylic acid (pyridin-3-ylmethyl)-amide;

5-(4-chloro-phenyl)-2-methyl-1-(4-sulfamoyl-phenyl)-1H-pyrrole-3-carboxylic acid (2-dimethylamino-ethyl)-amide;

5-(4-chloro-phenyl)-2-methyl-1-(4-sulfamoyl-phenyl)-1H-pyrrole-3-carboxylic acid-(3-dimethylamino-propyl)-amide;

5-(4-chloro-phenyl)-2-methyl-1-(4-sulfamoyl-phenyl)-1H-pyrrole-3-carboxylic acid-(2-hydroxy-ethyl)-propyl-amide;

5-(4-chloro-phenyl)-2-methyl-1-(4-sulfamoyl-phenyl)-1H-pyrrole-3-carboxylic acid-(3-hydroxy-propyl)-amide;

N-acetyl-4-[5-(4-chloro-phenyl)-2-methyl-3-propionyl-pyrrol-1-yl]-benzenesulfonamide N-acetyl-4-[5-(4-chloro-phenyl)-2-methyl-3-propionyl-pyrrol-1-yl]-benzenesulfonamide-N-sodium salt;

4-[5-(4-chloro-phenyl)-2-methyl-3-propionyl-pyrrol-1-yl]-N-propionyl-benzenesulfonamide; and 4-[5-(4-chloro-phenyl)-2-methyl-3-propionyl-pyrrol-1-yl]-N-propionyl-benzenesulfonamide-N-sodium salt.

Compound names are assigned by using AUTONOM naming software, which is provided by MDL Information Systems GmbH (formerly known as Beilstein Informationssysteme) of Frankfurt, Germany, and is part of the CHEMDRAW® ULTRA v. 6.0.2 software suite. Alternatively, compound names are assigned by using Struct=Name naming algorithm, which is part of the CHEMDRAW® ULTRA v. 9.0.7 software suite.

Compounds of the invention may exist as stereoisomers wherein, asymmetric or chiral centers are present. These stereoisomers are "R" or "S" depending on the configuration of substituents around the chiral element. The terms "R" and "S" used herein are configurations as defined in IUPAC 1974 Recommendations for Section E, Fundamental Stereochemistry, Pure Appl. Chem., 1976, 45: 13-30. The invention contemplates various stereoisomers and mixtures thereof that are specifically included within the scope of this invention. Stereoisomers include enantiomers and diastereomers, and mixtures of enantiomers or diastereomers. Individual stereoisomers of compounds of the invention may be prepared synthetically from commercially available starting materials which contain asymmetric or chiral centers or by preparation of racemic mixtures followed by resolution well-known to those of ordinary skill in the art. These methods of resolution are exemplified by (1) attachment of a mixture of enantiomers to a chiral auxiliary, separation of the resulting mixture of diastereomers by recrystallization or chromatography and optional liberation of the optically pure product from the auxiliary as described in Furniss, Hannaford, Smith, and Tatchell, "Vogel's Textbook of Practical Organic Chemistry", 5th edition (1989), Longman Scientific & Technical, Essex CM20 2JE, England, or (2) direct separation of the mixture of optical enantiomers on chiral chromatographic columns or (3) fractional recrystallization methods.

Methods of the Invention

Compounds and compositions of the invention are useful for modulating the effects of nAChRs, particularly by allosteric modulation. In particular, the compounds and compositions of the invention can be used for treating and preventing disorders modulated by nAChRs. Typically, such disorders can be ameliorated by modulating the nAChRs in a mammal, preferably by administering a compound or composition of the invention, either alone or in combination with another active agent, for example, as part of a therapeutic regimen.

Certain substituted pyrrole compounds, including but not limited to those specified as compounds of the invention, demonstrate the ability to affect nAChR activity, and particularly for allosteric modulation of nAChRs. Such compounds can be useful for the treatment and prevention of a number of nAChR-mediated diseases or conditions. Substituted pyrrole compounds contemplated to demonstrate such activity have the formula:

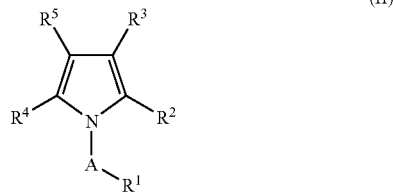

or a pharmaceutically acceptable salt, ester, amide, or prodrug thereof, wherein:

A is a 5- or 6-membered heteroaryl ring or a 6-membered aryl ring;

$R^1$ is hydrogen, alkyl, alkenyl, alkynyl, halo, haloalkyl, $OR^6$, nitro, $-NR^{8a}R^{8b}$, $CH_2NR^{8a}R^{8b}$, $-C(O)OR^9$, $-C(O)R^{10}$ or $-SO_2R^{10}$;

$R^2$ is hydrogen, alkyl, aryl, or heteroaryl;

$R^3$ is hydrogen, alkyl, alkenyl, alkynyl, aryl, halo, haloalkyl, heteroarylbicyclic heteroaryl-$C(O)R^{12}$; $-OR^9$, nitro or $-NR^{8a}R^{8b}$;

$R^4$ is hydrogen, alkyl, aryl or $-R^{14}-R^{15}$;

$R^5$ is hydrogen, halo, aryl, heteroaryl, bicyclic heteroaryl, bicyclic heteroaryl-$R^{23}-R^{24}$, or $-R^{23}C(O)-R^{24}$;

$R^6$ at each occurrence is independently hydrogen, alkyl, aryl, or heteroaryl;

$R^{8a}$ and $R^{8b}$ at each occurrence are independently hydrogen, alkyl, aryl, heteroaryl, $-C(O)OR^9$ or $-C(O)R^{10}$;

$R^9$ is hydrogen, alkyl or arylalkyl;

$R^{10}$ is alkyl, $-N=CHN(CH_3)_2$, or $-NR^{11a}R^{11b}$;

$R^{11a}$ and $R^{11b}$ are independently hydrogen, alkyl, alkylcarbonyl, aryl, heteroaryl or heterocycle; or $R^{11a}$ and $R^{11b}$ taken together with the nitrogen atom to which each is attached form a 4-, 5-, or 6-membered heterocycle;

$R^{12}$ is selected from the group consisting of hydrogen, alkyl, aryl, arylalkyl, cycloalkyl, heterocycle, heteroaryl, heteroarylalkyl, $-OR^{13}$ or $-NR^{16}R^{17}$;

$R^{13}$ is hydrogen, alkyl or arylalkyl;

$R^{14}$ is aryl;

$R^{15}$ is aryl, heteroaryl, heterocycle or $-R^{21}-R^{22}$;

$R^{16}$ and $R^{17}$ are independently hydrogen, alkyl, alkoxy, alkoxyalkyl, aryl, arylalkyl, cycloalkyl, heteroaryl, heteroarylalkyl, heterocycle, heterocyclealkyl, hydroxyalkyl or $R^{18}R^{19}N$-alkyl-;

$R^{18}$ and $R^{19}$ are independently hydrogen or alkyl;

$R^{21}$ is aryl or heteroaryl;

$R^{22}$ is arylalkyl;

$R^{23}$ is aryl; and $R^{24}$ is heteroaryl or heterocycle.

More particularly, compounds of formula (II), including, but not limited to, compounds wherein A is phenyl; and $R^2$ is alkyl are useful for the method of the invention. Compounds of formula (II) wherein A is phenyl; and $R^2$ is methyl are particularly beneficial.

In addition, compounds of formula (II) exist, wherein $R^1$ is $-SO_2$alkyl or $-SO_2NR^{11a}R^{11b}$ wherein $R^{11a}$ and $R^{11b}$ are independently selected from hydrogen, alkyl, alkylcarbonyl, aryl, heteroaryl, or heterocycle, or $R^{11a}$ and $R^{11b}$ taken together with the nitrogen atom to which each is attached form a 4-, 5-, or 6-membered heterocycle. More particularly, compounds of formula (II) exist wherein A is phenyl; $R^2$ is methyl; $R^1$ is $-SO_2$alkyl, $-SO_2NH_2$, or $-SO_2NR^{11a}R^{11b}$ wherein $R^{11a}$ and $R^{11b}$ taken together with the nitrogen atom to which each is attached form a 4-, 5-, or 6-membered heterocycle; $R^4$ is aryl, wherein aryl is optionally substituted with 1, 2 or 3 substituents selected from the group consisting of alkyl, alkylcarbonyl, alkoxy, alkylsulfonyl, cyano, halo, haloalkyl, nitro, and $-NR_AR_B$, wherein $R_A$ and $R_B$ are independently hydrogen, alkyl, alkylcarbonyl and alkylsulfonyl. Such compounds are useful for the method of the invention.

Specific embodiments contemplated as part of the method of the invention include, but are not limited to, the Examples provided in the Detailed Description of the Invention. Such embodiments include the compounds of Examples 1-146, excluding Examples 27, 61, and 62.

Accordingly, compounds of formula (I) or (II) are useful for preventing or treating a disorder mediated by nicotinic acetylcholine receptors. Such compounds can be administered to a subject having such a disorder or susceptible to such disorders in a therapeutically effective amount. The compounds are particularly useful for a method of treating a mammal having a condition where modulation of nicotinic acetylcholine receptor activity is of therapeutic benefit, wherein the method is accomplished by administering a therapeutically effective amount of a compound of formula (I) or (II) to a subject having, or susceptible to, such a disorder.

For example, α7 nAChRs have been shown to play a significant role in enhancing cognitive function, including aspects of learning, memory and attention (Levin, E. D., J. Neurobiol. 2002; 53: 633-640). As such, α7 ligands are suitable for the treatment of cognitive disorders including, for example, attention deficit disorder (ADD), attention deficit hyperactivity disorder (ADHD), Alzheimer's disease (AD), mild cognitive impairment, senile dementia, AIDS dementia, Pick's Disease, dementia associated with Lewy bodies, and dementia associated with Down's syndrome, as well as cognitive deficits associated with schizophrenia.

In addition, α7-containing nAChRs have been shown to be involved in the neuroprotective effects of nicotine both in vitro (Jonnala, R. B. and Buccafusco, J. J., J. Neurosci. Res. 2001; 66: 565-572) and in vivo (Shimohama, S. et al., Brain Res. 1998; 779: 359-363). More particularly, neurodegeneration underlies several progressive CNS disorders, including, but not limited to, Alzheimer's disease, Parkinson's disease, amyotrophic lateral sclerosis, Huntington's disease, dementia with Lewy bodies, as well as diminished CNS function resulting from traumatic brain injury. For example, the impaired function of α7 nAChRs by β-amyloid peptides linked to Alzheimer's disease has been implicated as a key factor in development of the cognitive deficits associated with the disease (Liu, Q.-S., Kawai, H., Berg, D. K., PNAS 2001; 98: 4734-4739). The activation of α7 nAChRs has been shown to block this neurotoxicity (Kihara, T. et al., J. Biol. Chem. 2001; 276: 13541-13546). As such, selective ligands that enhance α7 activity can counter the deficits of Alzheimer's and other neurodegenerative diseases.

Schizophrenia is a complex disease that is characterized by abnormalities in perception, cognition, and emotions. Significant evidence implicates the involvement of α7 nAChRs in this disease, including a measured deficit of these receptors in post-mortem patients (Leonard, S. Eur. J. Pharmacol. 2000; 393: 237-242). Deficits in sensory processing (gating) are one of the hallmarks of schizophrenia. These deficits can be normalized by nicotinic ligands that operate at the α7 nAChR (Adler L. E. et al., Schizophrenia Bull. 1998; 24: 189-202; Stevens, K. E. et al., Psychopharmacology 1998; 136: 320-327). Thus, α7 ligands demonstrate potential in the treatment schizophrenia.

Angiogenesis, a process involved in the growth of new blood vessels, is important in beneficial systemic functions, such as wound healing, vascularization of skin grafts, and enhancement of circulation, for example, increased circulation around a vascular occlusion. Non-selective nAChR agonists like nicotine have been shown to stimulate angiogenesis (Heeschen, C. et al., Nature Medicine 2001; 7: 833-839). Improved angiogenesis has been shown to involve activation of the α7 nAChR (Heeschen, C. et al, J. Clin. Invest. 2002; 110: 527-536). Therefore, nAChR ligands that are selective for the α7 subtype offer improved potential for stimulating angiogenesis with an improved side effect profile.

A population of α7 nAChRs in the spinal cord modulate serotonergic transmission that have been associated with the pain-relieving effects of nicotinic compounds (Cordero-Erausquin, M. and Changeux, J.-P. PNAS 2001; 98:2803-2807). The α7 nAChR ligands demonstrate therapeutic potential for the treatment of pain states, including acute pain, post-surgical pain, as well as chronic pain states including inflammatory pain and neuropathic pain. Moreover, α7 nAChRs are expressed on the surface of primary macrophages that are involved in the inflammation response, and that activation of the α7 receptor inhibits release of TNF and other cytokines that trigger the inflammation response (Wang, H. et al Nature 2003; 421: 384-388). TNF-α plays a pathological role in diverse inflammatory diseases including arthritis and psoriasis and endometriosis. Therefore, selective α7 ligands demonstrate potential for treating conditions involving inflammation and pain.

The mammalian sperm acrosome reaction is an exocytosis process important in fertilization of the ovum by sperm. Activation of an α7 nAChR on the sperm cell has been shown to be essential for the acrosome reaction (Son, J.-H. and Meizel, S. Biol. Reproduct. 2003; 68: 1348-1353). Consequently, selective α7 agents demonstrate utility for treating fertility disorders.

Compounds of the invention are particularly useful for treating and preventing a condition or disorder affecting cognition, neurodegeneration, and schizophrenia.

Cognitive impairment associated with schizophrenia often limits the ability of patients to function normally, a symptom not adequately treated by commonly available treatments, for example, treatment with an atypical antipsychotic. (Rowley, M. et al., J. Med. Chem. 2001; 44: 477-501). Such cognitive deficit has been linked to dysfunction of the nicotinic cholinergic system, in particular with decreased activity at α7 receptors. (Friedman, J. I. et al., Biol Psychiatry 2002; 51: 349-357). Thus, activators of α7 receptors can provide useful treatment for enhancing cognitive function in schizophrenic patients who are being treated with atypical antipsychotics. Accordingly, the combination of an α7 nAChR ligand and an atypical antipsychotic would offer improved therapeutic utility. Specific examples of suitable atypical antipsychotics include, but are not limited to, clozapine, risperidone, olanzapine, quietapine, ziprasidone, zotepine, iloperidone, and the like.

One of the measurable abnormalities in schizophrenic patients, is the P50 auditory gating deficit, an indication of impaired information processing and diminished ability to "filter" unimportant or repetitive sensory information. On the basis of clinical observations that these deficits are normalized by nicotine, it has been suggested that the high prevalence of smoking among patients with schizophrenia (>80%) may a form of self-medication. Pharmacological studies have shown that nicotine's mechanism of action is via α7 nAChRs. Restoration of P50 gating deficits in humans by α7 selective ligands—agonists and positive allosteric modulators—could lead to discontinuation of continuous smoking. Therefore, nAChR ligands that are selective for the α7 subtype be a therapy for smoking cessation, with an improved side effect profile compared to nicotine.

Actual dosage levels of active ingredients in the pharmaceutical compositions of this invention can be varied so as to obtain an amount of the active compound(s) that is effective to achieve the desired therapeutic response for a particular patient, compositions and mode of administration. The selected dosage level will depend upon the activity of the particular compound, the route of administration, the severity of the condition being treated and the condition and prior medical history of the patient being treated. However, it is within the skill of the art to start doses of the compound at levels lower than required to achieve the desired therapeutic effect and to gradually increase the dosage until the desired effect is achieved.

When used in the above or other treatments, a therapeutically effective amount of one of the compounds of the invention can be employed in pure form or, where such forms exist, in pharmaceutically acceptable salt, ester, amide or prodrug form. Alternatively, the compound can be administered as a pharmaceutical composition containing the compound of interest in combination with one or more pharmaceutically acceptable carriers. The phrase "therapeutically effective amount" of the compound of the invention means a sufficient amount of the compound to treat disorders, at a reasonable benefit/risk ratio applicable to any medical treatment. It will be understood, however, that the total daily usage of the compounds and compositions of the invention will be decided by the attending physician within the scope of sound medical judgment. The specific therapeutically effective dose level for any particular patient will depend upon a variety of factors including the disorder being treated and the severity of the disorder; activity of the specific compound employed; the specific composition employed; the age, body weight, general health, sex and diet of the patient; the time of administration, route of administration, and rate of excretion of the specific compound employed; the duration of the treatment; drugs used in combination or coincidental with the specific compound employed; and like factors well-known in the medical arts. For example, it is well within the skill of the art to start doses of the compound at levels lower than required to achieve the desired therapeutic effect and to gradually increase the dosage until the desired effect is achieved.

The total daily dose of the compounds of this invention administered to a human or lower animal range from about 0.001 mg/kg body weight to about 1 g/kg body weight. More preferable doses can be in the range of from about 0.001 mg/kg body weight to about 100 mg/kg body weight. If desired, the effective daily dose can be divided into multiple doses for purposes of administration. Consequently, single dose compositions may contain such amounts or submultiples thereof to make up the daily dose.

Methods for Preparing Compounds of the Invention

Nitrogen protecting groups can be used for protecting amine groups present in the described compounds. Such methods, and some suitable nitrogen protecting groups, are described in Greene and Wuts (Protective Groups In Organic Synthesis, Wiley and Sons, 1999). For example, suitable nitrogen protecting groups include, but are not limited to, tert-butoxycarbonyl (Boc), benzyloxycarbonyl (Cbz), benzyl (Bn), acetyl, and trifluoroacetyl. More particularly, the Boc protecting group may be removed by treatment with an acid such as trifluoroacetic acid or hydrochloric acid. The Cbz and Bn protecting groups may be removed by catalytic hydrogenation. The acetyl and trifluoroacetyl protecting groups may be removed by a hydroxide ion.

The methods described below can entail use of various enantiomers. Where the stereochemistry is shown in the Schemes, it is intended for illustrative purposes only.

Schemes

The compounds of the invention can be better understood in connection with the following synthetic schemes and methods which illustrate a means by which the compounds can be prepared.

Abbreviations which have been used in the descriptions of the schemes and the examples that follow are: Ethyl acetate (EtOAc), N,N-dimethylformamide (DMF), N,N-dimethylacetamide (DMA), hexane (hex), dimethylsulfoxide (DMSO), dichloromethane (DCM), HPLC for high pressure liquid chromatography; tetrahydrofuran (THF), acetonitrile (MeCN), methanol (MeOH), isopropyl alcohol (IPA), triethylamine (TEA or NEt$_3$), diisopropylethylamine (DIEA), p-toluenesulfonic acid (pTSA), 4-dimethylaminopyridine (DMAP), potassium carbonate (PC), trifluoroacetic acid (TFA), tris(dibenzylidineacetone)palladium (0) (Pd$_2$(dba)$_3$), 1-hydroxybenzotriazole (HOBT), 2,2'-bis(diphenylphosphino)-1,1'-binaphthalene (BINAP), thin-layer chromatography (TLC), high pressure liquid chromatography (HPLC), ethyl ether (Et$_2$O), equivalents (eq), fetal bovine serum (FBS), 4-(2-hydroxyethyl)-1-piperazineethanesulfonic acid (HEPES), polystyrene-supported N,N'-dicyclohexylcarbodiimide (PS-DCC), and rt for "room temperature" or ambient temperature suitably ranging 20-30° C.

The compounds of this invention can be prepared according to the synthetic Schemes and/or Experimentals described. Certain groups can be substituted as described within the scope of this invention as would be known to one skilled in the art. Representative procedures are shown in, but are not limited to, Schemes 1-7.

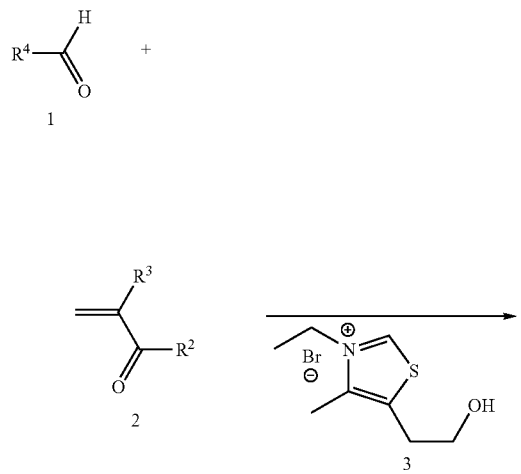

Compounds of formula 6, wherein A, R$^1$, R$^2$, R$^3$, and R$^4$ are as described in formula (I) or (II), can be obtained as outlined in Scheme 1. Compounds of formula 1 and compounds of formula 2, wherein R$^4$, R$^2$ and R$^3$ are as defined in formula (I), are heated together in the presence of compound of formula 3, (3-ethyl-5-(2-hydroxyethyl)-4-methylthiazolium bromide), and triethylamine in a solvent such as, but not limited to ethanol will provide compounds of formula 4. Compounds of formula 4 when treated with an amine of formula 5, wherein A and R$^1$ are as defined in formula (I), and a catalytic amount of para-toluenesulfonic acid under heated conditions in a solvent such as, but not limited to toluene, will provide compounds of formula 6 which are representative of compounds of the present invention.

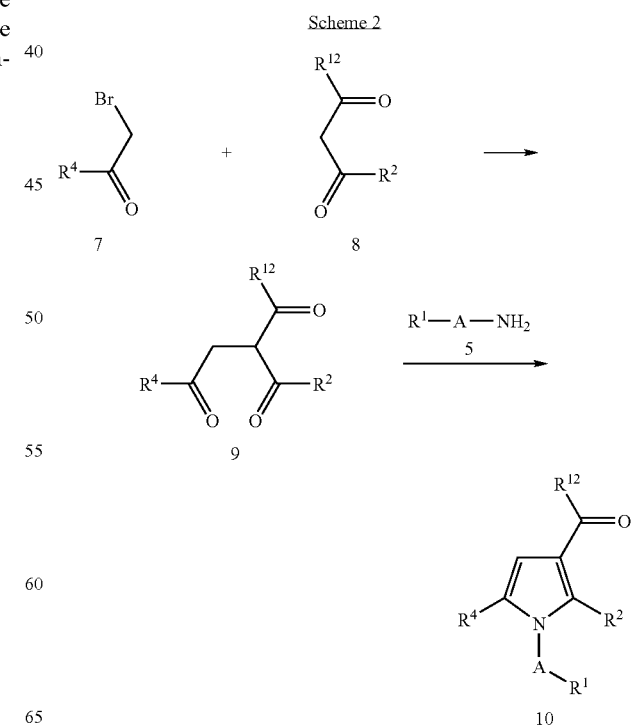

An alternative method of obtaining compounds of formula (I) is described in Scheme 2. Compounds of formula 8, when treated with a base such as, but not limited to potassium carbonate and a compound of formula 7 under heated conditions in a solvent such as, but not limited to 2-butanone, THF or acetonitrile will provide compounds of formula 9. Compounds of formula 9, when treated with compounds of formula 5, under heated conditions in a solvent such as, but not limited to glacial acetic acid will provide compounds of formula 10 which are representative of compounds of the present invention, wherein $R^{12}$ is alkyl, aryl, cycloalkyl, heteroaryl and $OR^{13}$.

Scheme 3

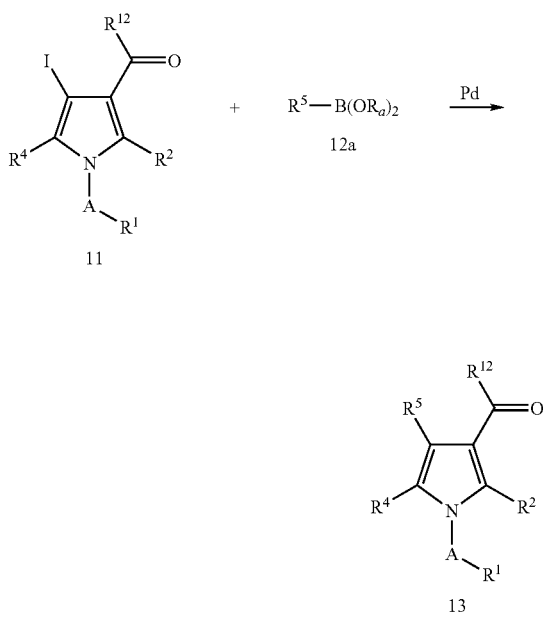

Compounds of formula 10, which can be obtained through the methods outlined in Scheme 2, when treated with iodine ($I_2$) in a solvent such as, but not limited to DMF will provide compounds of formula 11. Compounds of formula 11 when treated with a boronic acid or ester of formula 12a, wherein $R^5$ is aryl, heteroaryl or bicyclic heteroaryl, $R_a$ is hydrogen or alkyl, and a palladium catalyst such as, but not limited to palladium acetate suspended in a solvent such as, but not limited to ethanol along with an aqueous solution of a base such as, but not limited to 1 M aqueous $Cs_2CO_3$ under heated or microwave heated conditions will provide compounds of formula 13 which are representative of compounds of the present invention.

Scheme 4

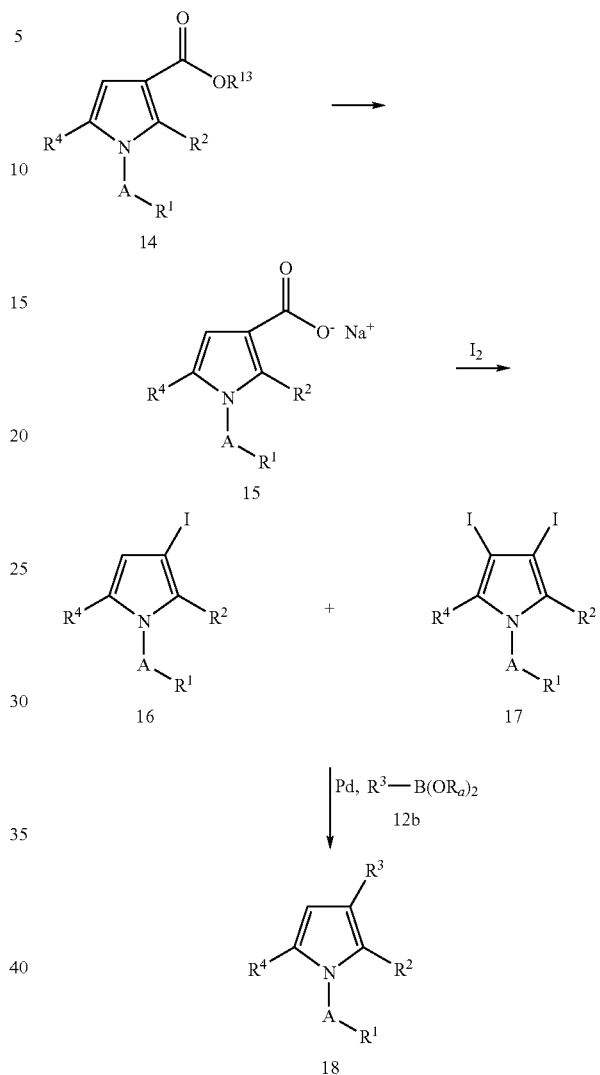

As outlined in Scheme 4, compounds of formula 14, which may be obtained according to the procedure outlined in Scheme 1 or 2, wherein $R^3$ is $C(O)R^{12}$ and $R^{12}$ is $—OR^{13}$ and $R^{13}$ is alkyl, when treated with reagents such as sodium hydroxide, potassium hydroxide or lithium hydroxide in solvents such as aqueous alcohol or aqueous THF will provide the corresponding salts of compounds of formula 15. Compounds of formula 15, when treated with iodine in solvents such as DMF according to conditions known to one skilled in the art will provide compounds of formula 16 often obtained as a mixture along with compounds of formula 17. Compounds of formula 16 which may be separated from compounds of formula 17 through chromatographic methods or other methods known to those skilled in the art, when treated with compounds of formula 12b, wherein $R^3$ is aryl, heteroaryl or bicyclic heteroaryl, $R_a$ is hydrogen or alkyl, and a palladium catalyst such as but not limited to palladium acetate suspended in a solvent such as, but not limited to ethanol along with an aqueous solution of a base such as, but not limited to 1 M aqueous $Cs_2CO_3$ under heated or microwave heated conditions will provide compounds of formula 18 which are representative of compounds of the present invention.

Scheme 5

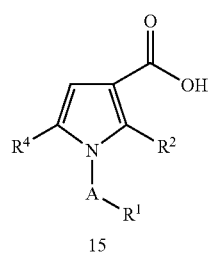

15

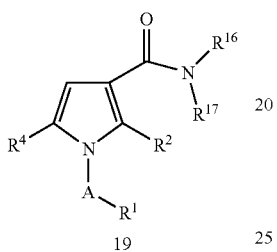

19

As outlined in Scheme 5, compounds of formula 15, which are obtained as outlined in Scheme 4, when treated with amines of formula $(R^{16}R^{17})NH$, wherein $R^{16}$ and $R^{17}$ are as described for compounds of formula (I), according to conditions known to convert carboxylic acids to amides as known to one skilled in the art, will provide compounds of formula 19 which are representative of compounds of the present invention when $R^3$ is $C(O)R^{12}$ and $R^{12}$ is $(R^{16}R^{17})N-$. Examples of conditions used to convert compounds of formula 15 into compounds of formula 19 include, treating compounds of formula 15 with reagents such as, but not limited to 1-(3-dimethylaminopropyl)-3-ethylcarbodiimide hydrochloride (EDCl), 1,3-dicyclohexylcarbodiimide (DCC), Bis(2-oxo-3-oxazolidinyl)phosphinic chloride (BOPCl), and O-benzotriazol-1-yl-N,N,N',N'-tetramethyluronium tetrafluoroborate (TBTU) along with auxiliary reagents such as 1-Hydroxy-7-azabenzotriazole (HOAT) and 1-hydroxybenzotriazole hydrate (HOBT) in solvents such as, but not limited to dichloromethane and THF. Additionally, a mixture of compounds of formula 15 and compounds of formula $(R^{16}R^{17})NH$ may be treated with PS-DCC (polymer supported DCC) and HOBT in solvents such as DMA under heated microwave conditions to provide compounds of formula 19.

Scheme 6

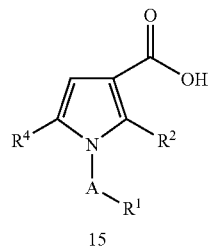

15

-continued

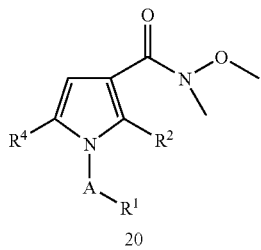 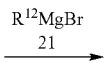

20

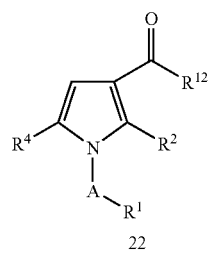

22

As outlined in Scheme 6, compounds of formula 15 may also be treated using conditions demonstrated in Scheme 5 in the presence of N,O-dimethylhydroxylamine to provide compounds of formula 20. Alternatively, compounds of formula 15 may also be converted to their corresponding acid chloride according to conditions known to one skilled in the art or by treatment with oxalyl chloride in THF along with a catalytic amount of DMF followed by treatment with N,O-dimethylhydroxylamine hydrochloride and triethylamine in THF to provide compounds of formula 20. The Weinreb amide group of compounds of formula 20 when treated with Grignard reagents of formula 21 will provide compounds of formula 22 which are representative of compounds of the present invention where $R^{12}$ is alkyl, aryl, cycloalkyl, or heteroaryl.

Scheme 7

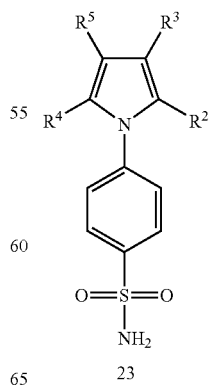

23

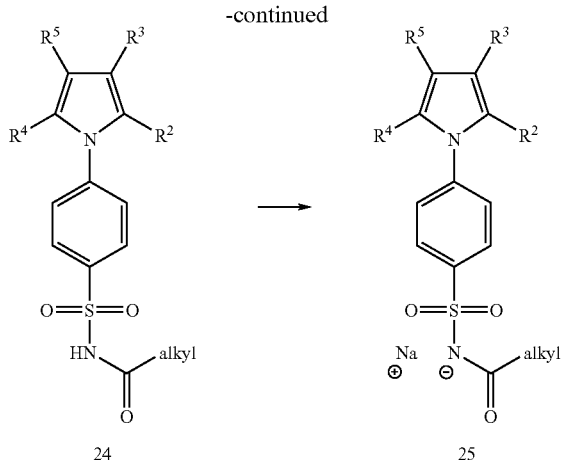

As contemplated within the scope of this invention, compounds of formula (I) may exist as prodrugs, as outlined in Scheme 7. Compounds of formula 23 are representative of compounds of the present invention, when A is phenyl, $R^1$ is $SO_2R^{10}$, $R^{10}$ is $NR^{11a}R^{11b}$, and $R^{11a}$ and $R^{11b}$ are hydrogen. Compounds of formula 23 when treated with an alkylcarbonyl anhydride such as, but not limited to ethyl or propylcarboxyanhydride, in the presence of a base such as but not limited to triethylamine in a solvent such as but not limited to THF will provide compounds of formula 24 which are considered prodrugs of the parent compounds under the scope of compounds of formula (I). Furthermore, compounds of formula 24 when treated with a mineral base such as sodium hydroxide will provide compounds of formula 25 which are considered salts of compounds of formula (I).

In addition, nitrogen protecting groups can be used for protecting amine groups during the synthesis of compounds of formula (I) or (II). Such methods, and some suitable nitrogen protecting groups, are described in Greene and Wuts (Protective Groups In Organic Synthesis, Wiley and Sons, 1999). For example, suitable nitrogen protecting groups include, but are not limited to, tert-butoxycarbonyl (Boc), benzyloxycarbonyl (Cbz), benzyl (Bn), acetyl, and trifluoroacetyl. More particularly, the Boc protecting group may be removed by treatment with an acid such as trifluoroacetic acid or hydrochloric acid. The Cbz and Bn protecting groups may be removed by catalytic hydrogenation and acetyl and trifluoroacetyl protecting groups may be removed by variety of conditions including the use of sodium hydroxide, potassium hydroxide or lithium hydroxide in aqueous, organic, or alcoholic solvents or mixtures thereof.

The compounds and intermediates of the invention may be isolated and purified by methods well-known to those skilled in the art of organic synthesis. Examples of conventional methods for isolating and purifying compounds can include, but are not limited to, chromatography on solid supports such as silica gel, alumina, or silica derivatized with alkylsilane groups, by recrystallization at high or low temperature with an optional pretreatment with activated carbon, thin-layer chromatography, distillation at various pressures, sublimation under vacuum, and trituration, as described for instance in "Vogel's Textbook of Practical Organic Chemistry", 5th edition (1989), by Furniss, Hannaford, Smith, and Tatchell, pub. Longman Scientific & Technical, Essex CM20 2JE, England.

Compositions of the Invention

The invention also provides pharmaceutical compositions comprising a therapeutically effective amount of a compound of formula (I) in combination with a pharmaceutically acceptable carrier. The compositions comprise compounds of the invention formulated together with one or more non-toxic pharmaceutically acceptable carriers. The pharmaceutical compositions can be formulated for oral administration in solid or liquid form, for parenteral injection or for rectal administration.

The term "pharmaceutically acceptable carrier," as used herein, means a non-toxic, inert solid, semi-solid or liquid filler, diluent, encapsulating material or formulation auxiliary of any type. Some examples of materials which can serve as pharmaceutically acceptable carriers are sugars such as lactose, glucose and sucrose; starches such as corn starch and potato starch; cellulose and its derivatives such as sodium carboxymethyl cellulose, ethyl cellulose and cellulose acetate; powdered tragacanth; malt; gelatin; talc; cocoa butter and suppository waxes; oils such as peanut oil, cottonseed oil, safflower oil, sesame oil, olive oil, corn oil and soybean oil; glycols; such a propylene glycol; esters such as ethyl oleate and ethyl laurate; agar; buffering agents such as magnesium hydroxide and aluminum hydroxide; alginic acid; pyrogen-free water; isotonic saline; Ringer's solution; ethyl alcohol, and phosphate buffer solutions, as well as other non-toxic compatible lubricants such as sodium lauryl sulfate and magnesium stearate, as well as coloring agents, releasing agents, coating agents, sweetening, flavoring and perfuming agents, preservatives and antioxidants can also be present in the composition, according to the judgment of one skilled in the art of formulations.

The pharmaceutical compositions of this invention can be administered to humans and other mammals orally, rectally, parenterally, intracisternally, intravaginally, intraperitoneally, topically (as by powders, ointments or drops), bucally or as an oral or nasal spray. The term "parenterally," as used herein, refers to modes of administration, including intravenous, intramuscular, intraperitoneal, intrasternal, subcutaneous, intraarticular injection and infusion.

Pharmaceutical compositions for parenteral injection comprise pharmaceutically acceptable sterile aqueous or non-aqueous solutions, dispersions, suspensions or emulsions and sterile powders for reconstitution into sterile injectable solutions or dispersions. Examples of suitable aqueous and non-aqueous carriers, diluents, solvents or vehicles include water, ethanol, polyols (propylene glycol, polyethylene glycol, glycerol, and the like, and suitable mixtures thereof), vegetable oils (such as olive oil) and injectable organic esters such as ethyl oleate, or suitable mixtures thereof. Suitable fluidity of the composition may be maintained, for example, by the use of a coating such as lecithin, by the maintenance of the required particle size in the case of dispersions, and by the use of surfactants.

These compositions can also contain adjuvants such as preservative agents, wetting agents, emulsifying agents, and dispersing agents. Prevention of the action of microorganisms can be ensured by various antibacterial and antifungal agents, for example, parabens, chlorobutanol, phenol, sorbic acid, and the like. It also can be desirable to include isotonic agents, for example, sugars, sodium chloride and the like. Prolonged absorption of the injectable pharmaceutical form can be brought about by the use of agents delaying absorption, for example, aluminum monostearate and gelatin.

In some cases, in order to prolong the effect of a drug, it is often desirable to slow the absorption of the drug from subcutaneous or intramuscular injection. This can be accomplished by the use of a liquid suspension of crystalline or amorphous material with poor water solubility. The rate of absorption of the drug can depend upon its rate of dissolution, which, in turn, may depend upon crystal size and crystalline form. Alternatively, a parenterally administered drug form can be administered by dissolving or suspending the drug in an oil vehicle.

Suspensions, in addition to the active compounds, can contain suspending agents, for example, ethoxylated isostearyl alcohols, polyoxyethylene sorbitol and sorbitan esters, microcrystalline cellulose, aluminum metahydroxide, bentonite, agar-agar, tragacanth, and mixtures thereof.

If desired, and for more effective distribution, the compounds of the invention can be incorporated into slow-release or targeted-delivery systems such as polymer matrices, liposomes, and microspheres. They may be sterilized, for example, by filtration through a bacteria-retaining filter or by incorporation of sterilizing agents in the form of sterile solid compositions, which may be dissolved in sterile water or some other sterile injectable medium immediately before use.

Injectable depot forms are made by forming microencapsulated matrices of the drug in biodegradable polymers such as polylactide-polyglycolide. Depending upon the ratio of drug to polymer and the nature of the particular polymer employed, the rate of drug release can be controlled. Examples of other biodegradable polymers include poly (orthoesters) and poly(anhydrides) Depot injectable formulations also are prepared by entrapping the drug in liposomes or microemulsions which are compatible with body tissues.

The injectable formulations can be sterilized, for example, by filtration through a bacterial-retaining filter or by incorporating sterilizing agents in the form of sterile solid compositions which can be dissolved or dispersed in sterile water or other sterile injectable medium just prior to use.

Injectable preparations, for example, sterile injectable aqueous or oleaginous suspensions can be formulated according to the known art using suitable dispersing or wetting agents and suspending agents. The sterile injectable preparation also can be a sterile injectable solution, suspension or emulsion in a nontoxic, parenterally acceptable diluent or solvent such as a solution in 1,3-butanediol. Among the acceptable vehicles and solvents that can be employed are water, Ringer's solution, U.S.P. and isotonic sodium chloride solution. In addition, sterile, fixed oils are conventionally employed as a solvent or suspending medium. For this purpose any bland fixed oil can be employed including synthetic mono- or diglycerides. In addition, fatty acids such as oleic acid are used in the preparation of injectables.

Solid dosage forms for oral administration include capsules, tablets, pills, powders, and granules. In such solid dosage forms, one or more compounds of the invention is mixed with at least one inert pharmaceutically acceptable carrier such as sodium citrate or dicalcium phosphate and/or a) fillers or extenders such as starches, lactose, sucrose, glucose, mannitol, and salicylic acid; b) binders such as carboxymethylcellulose, alginates, gelatin, polyvinylpyrrolidinone, sucrose, and acacia; c) humectants such as glycerol; d) disintegrating agents such as agar-agar, calcium carbonate, potato or tapioca starch, alginic acid, certain silicates, and sodium carbonate; e) solution retarding agents such as paraffin; f) absorption accelerators such as quaternary ammonium compounds; g) wetting agents such as cetyl alcohol and glycerol monostearate; h) absorbents such as kaolin and bentonite clay; and i) lubricants such as talc, calcium stearate, magnesium stearate, solid polyethylene glycols, sodium lauryl sulfate, and mixtures thereof. In the case of capsules, tablets and pills, the dosage form may also comprise buffering agents.

Solid compositions of a similar type may also be employed as fillers in soft and hard-filled gelatin capsules using lactose or milk sugar as well as high molecular weight polyethylene glycols.

The solid dosage forms of tablets, dragees, capsules, pills, and granules can be prepared with coatings and shells such as enteric coatings and other coatings well-known in the pharmaceutical formulating art. They can optionally contain opacifying agents and can also be of a composition that they release the active ingredient(s) only, or preferentially, in a certain part of the intestinal tract in a delayed manner. Examples of materials useful for delaying release of the active agent can include polymeric substances and waxes.

Compositions for rectal or vaginal administration are preferably suppositories which can be prepared by mixing the compounds of this invention with suitable non-irritating carriers such as cocoa butter, polyethylene glycol or a suppository wax which are solid at ambient temperature but liquid at body temperature and therefore melt in the rectum or vaginal cavity and release the active compound.

Liquid dosage forms for oral administration include pharmaceutically acceptable emulsions, microemulsions, solutions, suspensions, syrups and elixirs. In addition to the active compounds, the liquid dosage forms may contain inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethylformamide, oils (in particular, cottonseed, groundnut, corn, germ, olive, castor, and sesame oils), glycerol, tetrahydrofurfuryl alcohol, polyethylene glycols and fatty acid esters of sorbitan, and mixtures thereof.

Besides inert diluents, the oral compositions can also include adjuvants such as wetting agents, emulsifying and suspending agents, sweetening, flavoring, and perfuming agents.

Dosage forms for topical or transdermal administration of a compound of this invention include ointments, pastes, creams, lotions, gels, powders, solutions, sprays, inhalants or patches. A desired compound of the invention is admixed under sterile conditions with a pharmaceutically acceptable carrier and any needed preservatives or buffers as may be required. Ophthalmic formulation, eardrops, eye ointments, powders and solutions are also contemplated as being within the scope of this invention.

The ointments, pastes, creams and gels may contain, in addition to an active compound of this invention, animal and vegetable fats, oils, waxes, paraffins, starch, tragacanth, cellulose derivatives, polyethylene glycols, silicones, bentonites, silicic acid, talc and zinc oxide, or mixtures thereof.

Powders and sprays can contain, in addition to the compounds of this invention, lactose, talc, silicic acid, aluminum hydroxide, calcium silicates and polyamide powder, or mixtures of these substances. Sprays can additionally contain customary propellants such as chlorofluorohydrocarbons.

Compounds of the invention also can be administered in the form of liposomes. As is known in the art, liposomes are generally derived from phospholipids or other lipid substances. Liposomes are formed by mono- or multi-lamellar hydrated liquid crystals that are dispersed in an aqueous medium. Any non-toxic, physiologically acceptable and metabolizable lipid capable of forming liposomes may be used. The present compositions in liposome form may contain, in addition to the compounds of the invention, stabilizers, preservatives, and the like. The preferred lipids are the natural and synthetic phospholipids and phosphatidylcholines (lecithins) used separately or together.

Methods to form liposomes are known in the art. See, for example, Prescott, Ed., Methods in Cell Biology, Volume XIV, Academic Press, New York, N.Y., (1976), p 33 et seq.

Dosage forms for topical administration of a compound of this invention include powders, sprays, ointments and inhalants. The active compound is mixed under sterile conditions with a pharmaceutically acceptable carrier and any needed preservatives, buffers or propellants. Ophthalmic formulations, eye ointments, powders and solutions are also contemplated as being within the scope of this invention. Aqueous liquid compositions of the invention also are particularly useful.

The compounds of the invention can be used in the form of pharmaceutically acceptable salts, esters, or amides derived from inorganic or organic acids. The term "pharmaceutically acceptable salts, esters and amides," as used herein, include salts, zwitterions, esters and amides of compounds of formula (I) which are, within the scope of sound medical judgment, suitable for use in contact with the tissues of humans and lower animals without undue toxicity, irritation, allergic response, and the like, are commensurate with a reasonable benefit/risk ratio, and are effective for their intended use.

The term "pharmaceutically acceptable salt" refers to those salts which are, within the scope of sound medical judgment, suitable for use in contact with the tissues of humans and lower animals without undue toxicity, irritation, allergic response, and the like, and are commensurate with a reasonable benefit/risk ratio. Pharmaceutically acceptable salts are well-known in the art. The salts can be prepared in situ during the final isolation and purification of the compounds of the invention or separately by reacting a free base function with a suitable organic acid.

Representative acid addition salts include, but are not limited to acetate, adipate, alginate, citrate, aspartate, benzoate, benzenesulfonate, bisulfate, butyrate, camphorate, camphorsulfonate, digluconate, glycerophosphate, hemisulfate, heptanoate, hexanoate, fumarate, hydrochloride, hydrobromide, hydroiodide, 2-hydroxyethansulfonate (isethionate), lactate, maleate, methanesulfonate, nicotinate, 2-naphthalenesulfonate, oxalate, pamoate, pectinate, persulfate, 3-phenylpropionate, picrate, pivalate, propionate, succinate, tartrate, thiocyanate, phosphate, glutamate, bicarbonate, p-toluenesulfonate and undecanoate.

Also, the basic nitrogen-containing groups can be quaternized with such agents as lower alkyl halides such as methyl, ethyl, propyl, and butyl chlorides, bromides and iodides; dialkyl sulfates such as dimethyl, diethyl, dibutyl and diamyl sulfates; long chain halides such as decyl, lauryl, myristyl and stearyl chlorides, bromides and iodides; arylalkyl halides such as benzyl and phenethyl bromides and others. Water or oil-soluble or dispersible products are thereby obtained.

Examples of acids which can be employed to form pharmaceutically acceptable acid addition salts include such inorganic acids as hydrochloric acid, hydrobromic acid, sulphuric acid and phosphoric acid and such organic acids as oxalic acid, maleic acid, succinic acid, and citric acid.

Basic addition salts can be prepared in situ during the final isolation and purification of compounds of this invention by reacting a carboxylic acid-containing moiety with a suitable base such as the hydroxide, carbonate or bicarbonate of a pharmaceutically acceptable metal cation or with ammonia or an organic primary, secondary or tertiary amine. Pharmaceutically acceptable salts include, but are not limited to, cations based on alkali metals or alkaline earth metals such as lithium, sodium, potassium, calcium, magnesium, and aluminum salts, and the like, and nontoxic quaternary ammonia and amine cations including ammonium, tetramethylammonium, tetraethylammonium, methylammonium, dimethylammonium, trimethylammonium, triethylammonium, diethylammonium, ethylammonium and the like. Other representative organic amines useful for the formation of base addition salts include ethylenediamine, ethanolamine, diethanolamine, piperidine, and piperazine.

The term "pharmaceutically acceptable ester," as used herein, refers to esters of compounds of the invention which hydrolyze in vivo and include those that break down readily in the human body to leave the parent compound or a salt thereof. Examples of pharmaceutically acceptable, non-toxic esters of the invention include $C_1$-to-$C_6$ alkyl esters and $C_5$-to-$C_7$ cycloalkyl esters, although $C_1$-to-$C_4$ alkyl esters are preferred. Esters of the compounds of formula (I) can be prepared according to conventional methods. Pharmaceutically acceptable esters can be appended onto hydroxy groups by reaction of the compound that contains the hydroxy group with an acid such as hydrochloric acid and an alkylcarboxylic acid such as acetic acid, or with acid and an arylcarboxylic acid such as benzoic acid. In the case of compounds containing carboxylic acid groups, the pharmaceutically acceptable esters are prepared from compounds containing the carboxylic acid groups by reaction of the compound with base such as triethylamine and an alkyl halide or alkyl triflate, for example with methyl iodide, benzyl iodide, cyclopentyl iodide. They also may be prepared by reaction of the compound containing the carboxylic acid group with an acid such as hydrochloric acid and an alkylcarboxylic acid such as acetic acid, or with acid and an arylcarboxylic acid such as benzoic acidalcohol such as methanol or ethanol.

The term "pharmaceutically acceptable amide," as used herein, refers to non-toxic amides of the invention derived from ammonia, primary $C_1$-to-$C_6$ alkyl amines and secondary $C_1$-to-$C_6$ dialkyl amines. In the case of secondary amines, the amine can also be in the form of a 5- or 6-membered heterocycle containing one nitrogen atom. Amides derived from ammonia, $C_1$-to-$C_3$ alkyl primary amides and $C_1$-to-$C_2$ dialkyl secondary amides are preferred. Amides of the compounds of formula (I) can be prepared according to conventional methods. Pharmaceutically acceptable amides can be prepared from compounds containing primary or secondary amine groups by reaction of the compound that contains the amino group with an alkyl anhydride, aryl anhydride, acyl halide, or aroyl halide. In the case of compounds containing carboxylic acid groups, the pharmaceutically acceptable amides are prepared from compounds containing the carboxylic acid groups by reaction of the compound with base such as triethylamine, a coupling agent such as dicyclohexyl carbodiimide or carbonyl diimidazole, and an alkyl amine, dialkylamine, for example with methylamine, diethylamine, piperidine.

The term "pharmaceutically acceptable prodrug" or "prodrug," as used herein, represents those prodrugs of the compounds of the invention which are, within the scope of sound medical judgment, suitable for use in contact with the tissues of humans and lower animals without undue toxicity, irritation, allergic response, and the like, commensurate with a reasonable benefit/risk ratio, and effective for their intended use. Prodrugs of the invention can be rapidly transformed in vivo to a parent compound of formula (I), for example, by hydrolysis in blood. A thorough discussion is provided in T. Higuchi and V. Stella, Pro-drugs as Novel Delivery Systems, V. 14 of the A.C.S. Symposium Series, and in Edward B. Roche, ed., Bioreversible Carriers in Drug Design, American Pharmaceutical Association and Pergamon Press (1987).

The invention contemplates pharmaceutically active compounds either chemically synthesized or formed by in vivo biotransformation to compounds of formula (I).

The compounds, compositions, and methods of the invention will be better understood by reference to the following examples and reference examples, which are intended as an illustration of and not a limitation upon the scope of the invention.

EXAMPLES

The compounds and processes of the invention will be better understood by reference to the following examples, which are intended as an illustration of and not a limitation upon the scope of the invention.

Example 1 ethyl 1-[4-(aminosulfonyl)phenyl]-5-(4-bromophenyl)-2-methyl-1H-pyrrole-3-carboxylate Example 1A ethyl 2-acetyl-4-(4-bromophenyl)-4-oxobutanoate A mixture of 2,4'-dibromoacetophenone (3.0 g, 10.8 mmol), ethyl acetoacetate (1.48 mL, 10.8 mmol) and potassium carbonate (4.5 g, 32.4 mmol) were heated in 2-butanone (50 mL) at reflux for 24 hours. Upon cooling, the mixture was filtered over diatomaceous earth and concentrated. The residue was purified by chromatography with DCM to provide the title compound as an oil. $^1$H NMR (CDCl$_3$) δ ppm 1.30 (3H), 2.10 (3H), 3.19 (2H), 3.75 (1H), 4.15 (2H), 7.50 (2H), 7.81 (2H); MS (ESI) m/z 326/328.

Example 1B ethyl 1-[4-(aminosulfonyl)phenyl]-5-(4-bromophenyl)-2-methyl-1H-pyrrole-3-carboxylate A mixture of Example 1A (3.3 g, 10.1 mmol) and 4-aminobenzenesulfonamide (1.74 g, 10.1 mmol) in glacial acetic acid (75 mL) was heated to 100° C. for 48 hours. After cooling the mixture was concentrated under reduced pressure. Ether (50 mL) was added to the residue and the precipitate was isolated by filtration. The pale yellow solid was washed with ether and dried. $^1$H NMR (CDCl$_3$) δ ppm 1.32 (3H), 2.20 (3H), 3.50 (2H), 4.27 (2H), 6.85 (1H), 7.30-7.90 (8H); MS (ESI) m/z m/z 462/464.

Example 2 ethyl 5-(4-bromophenyl)-2-methyl-1-[3-(methylsulfonyl)phenyl]-1H-pyrrole-3-carboxylate This titled compound was prepared according to conditions described in Example 1B substituting 3-(methylsulfonyl)aniline for 4-aminobenzenesulfonamide. $^1$H NMR (CDCl$_3$) δ ppm 1.32 (3H), 2.20 (3H), 2.85 (3H), 4.27 (2H), 6.99 (1H), 7.30-7.90 (8H). MS (ESI) m/z m/z 461/463.

General Procedure A

A mixture of bromine substituted phenylpyrrole (such as but not limited to Example 1 or 2, 0.1 mmol), a boronic acid (1.3 eq), Pd(PPh$_3$)$_2$Cl$_2$ (0.05 eq) and aqueous sodium carbonate (1 M, 3 eq) in 5 mL of IPA was heated to 60° C. overnight. After cooling and filtration, the mixture was concentrated under reduced pressure and purified by chromatography eluting with a gradient of EtOAc (0-25%) in DCM.

Example 3

5-biphenyl-4-yl-2-methyl-1-(4-sulfamoyl-phenyl)-1H-pyrrole-3-carboxylic Acid Ethyl Ester The titled compound was obtained according to General Procedure A, using Example 1 and phenyl boronic acid. $^1$H NMR (CDCl$_3$) δ ppm 1.32 (3H), 2.25 (3H), 3.55 (2H), 4.20 (2H), 6.95 (1H), 7.30-7.90 (13H); MS (ESI) m/z 461 (M+H).

Example 4

5-(4'-chloro-biphenyl-4-yl)-2-methyl-1-(4-sulfamoyl-phenyl)-1H-pyrrole-3-carboxylic Acid Ethyl Ester The titled compound was obtained according to General Procedure A using Example 1 and p-chlorophenyl boronic acid. $^1$H NMR (CDCl$_3$) δ ppm 1.30 (3H), 2.30 (3H), 3.50 (2H), 4.22 (2H), 7.0 (1H), 7.30-7.90 (12H); MS (ESI) m/z 495 (M+H).

Example 5

5-(4'-methoxy-biphenyl-4-yl)-2-methyl-1-(4-sulfamoyl-phenyl)-1H-pyrrole-3-carboxylic Acid Ethyl Ester The titled compound was obtained according to General Procedure A using Example 1 and p-methoxyphenyl boronic acid. $^1$H NMR (CDCl$_3$) δ ppm 1.30 (3H), 2.30 (3H), 3.56 (2H), 3.73 (3H), 4.18 (2H), 7.0 (1H), 7.30-7.90 (12H); MS (ESI) m/z 491 (M+H).

Example 6

5-(3',5'-difluoro-biphenyl-4-yl)-2-methyl-1-(4-sulfamoyl-phenyl)-1H-pyrrole-3-carboxylic Acid Ethyl Ester The titled compound was obtained according to General Procedure A using Example 1 and 3,5-difluoro-phenyl boronic acid. $^1$H NMR (CDCl$_3$) δ ppm 1.32 (3H), 2.31 (3H), 3.56 (2H), 4.20 (2H), 6.60 (1H), 6.98 (3H), 7.50-7.90 (8H); MS (ESI) m/z 497 (M+H).

Example 7

5-(3'-cyano-biphenyl-4-yl)-2-methyl-1-(4-sulfamoyl-phenyl)-1H-pyrrole-3-carboxylic Acid Ethyl Ester The titled compound was obtained according to General Procedure A using Example 1 and m-cyanoyphenyl boronic acid. $^1$H NMR (CDCl$_3$) δ ppm 1.35 (3H), 2.40 (3H), 3.72 (2H), 4.28 (2H), 6.99 (1H), 7.45-7.95 (12H); MS (ESI) m/z 486 (M+H).

Example 8

5-(4-furan-3-yl-phenyl)-2-methyl-1-(4-sulfamoyl-phenyl)-1H-pyrrole-3-carboxylic acid ethyl ester The titled compound was obtained according to General Procedure A using Example 1 and 3-furyl boronic acid. $^1$H NMR (CDCl₃) δ ppm 1.34 (3H), 2.50 (3H), 3.70 (2H), 4.28 (2H), 6.35 (1H), 6.89 (1H), 7.44 (2H), 7.54-7.90 (8H); MS (ESI) m/z 451 (M+H).

Example 9

2-methyl-1-(4-sulfamoyl-phenyl)-5-(4-thiophen-3-yl-phenyl)-1H-pyrrole-3-carboxylic acid ethyl ester The titled compound was obtained according to General Procedure A using Example 1 and 3-thiophene boronic acid. ¹H NMR (CDCl₃) δ ppm 1.34 (3H), 2.45 (3H), 4.10 (2H), 4.28 (2H), 6.89 (1H), 7.03 (1H), 7.25 (2H), 7.60-7.93 (8H); MS (ESI) m/z 467 (M+H).

Example 10

2-methyl-5-(4-pyridin-4-yl-phenyl)-1-(4-sulfamoyl-phenyl)-1H-pyrrole-3-carboxylic acid ethyl ester The titled compound was obtained according to General Procedure A using Example 1 and 4-pyridinyl boronic acid. ¹H NMR (CDCl₃) δ ppm 1.40 (3H), 2.40 (3H), 3.89 (2H), 4.18 (2H), 6.89 (1H), 7.60-7.93 (10H), 8.68 (2H); MS (ESI) m/z 462 (M+H).

Example 11

1-(3-methanesulfanyl-phenyl)-2-methyl-5-[4-(1-methyl-1H-pyrazol-4-yl)-phenyl]-1H-pyrrole-3-carboxylic acid ethyl ester The titled compound was obtained according to General Procedure A using Example 2 and 4-[1-methyl-1H-pyrazol] boronic acid. ¹H NMR (CDCl₃) δ ppm 1.40 (3H), 2.40 (3H), 2.85 (2H), 3.80 (3H), 4.28 (2H), 6.90 (1H), 7.54-7.93 (10H), 8.20 (1H), 8.34 (1H); MS (ESI) m/z 464 (M+H).

Example 12

5-[4-(1-benzyl-1H-pyrazol-4-yl)-phenyl]-1-(3-methanesulfonyl-phenyl)-2-methyl-1H-pyrrole-3-carboxylic Acid Ethyl Ester The titled compound was obtained according to General Procedure A using Example 2 and 4-[1-benzyl-pyrazolyl] boronic acid. ¹H NMR (CDCl₃) δ ppm 1.35 (3H), 2.15 (3H), 2.85 (3H), 4.28 (2H), 5.01 (2H), 6.80 (1H), 7.05-7.20 (5H), 7.50-7.93 (8H), 8.22 (1H), 8.39 (1H); MS (ESI) m/z 540 (M+H).

Example 13

1-(3-methanesulfonyl-phenyl)-2-methyl-5-(4-pyridin-4-yl-phenyl)-1H-pyrrole-3-carboxylic Acid Ethyl Ester The titled compound was obtained according to General Procedure A using Example 2 and 4-pyridinyl boronic acid. ¹H NMR (CDCl₃) δ ppm 1.30 (3H), 2.16 (3H), 2.80 (3H), 4.28 (2H), 6.80 (1H), 7.05-7.20 (4H), 7.50-8.82 (8H); MS (ESI) m/z 461 (M+H).

Example 14

5-[4-(5-cyano-pyridin-3-yl)-phenyl]-1-(3-methanesulfonyl-phenyl)-2-methyl-1H-pyrrole-3-carboxylic Acid Ethyl Ester The titled compound was obtained according to General Procedure A using Example 2 and 5-cyanopyridin-3-ylboronic acid. ¹H NMR (CDCl₃) δ ppm 1.35 (3H), 2.21 (3H), 2.83 (3H), 4.25 (2H), 6.90 (1H), 7.05-7.20 (4H), 7.50-7.95 (4H), 8.70 (1H), 9.20 (1H), 9.35 (1H); MS (ESI) m/z 486 (M+H).

Example 15

5-(4'-chloro-biphenyl-4-yl)-1-(3-methanesulfonyl-phenyl)-2-methyl-1H-pyrrole-3-carboxylic Acid Ethyl Ester The titled compound was obtained according to General Procedure A using Example 2 and 4-chlorophenyl boronic acid. ¹H NMR (CDCl₃) δ ppm 1.31 (3H), 2.20 (3H), 2.80 (3H), 4.35 (2H), 6.89 (1H), 7.33-7.91 (12H); MS (ESI) m/z 494 (M+H).

Example 16

1-(3-methansulfonyl-phenyl)-5-(4'-methoxy-biphenyl-4-yl)-2-methyl-1H-pyrrole-3-carboxylic Acid Ethyl Ester The titled compound was obtained according to General Procedure A using Example 2 and 4-methoxyphenyl boronic acid. ¹H NMR (CDCl₃) δ ppm 1.31 (3H), 2.20 (3H), 2.80 (3H), 3.70 (3H), 4.35 (2H), 6.80 (1H), 6.85-7.40 (4H), 7.50-7.91 (8H); MS (ESI) m/z 490 (M+H).

Example 17

5-(4'-cyano-biphenyl-4-yl)-1-(3-methanesulfonyl-phenyl)-2-methyl-1H-pyrrole-3-carboxylic Acid Ethyl Ester The titled compound was obtained according to General Procedure A using Example 2 and 4-cyanophenyl boronic acid. ¹H NMR (CDCl₃) δ ppm 1.31 (3H), 2.20 (3H), 2.80 (3H), 4.35 (2H), 6.80 (1H), 7.50-7.90 (12H); MS (ESI) m/z 485 (M+H).

Example 18

1-(3-methanesulfonyl-phenyl)-2-methyl-5-(4-morpholin-4-yl-phenyl)-1H-pyrrole-3-carboxylic Acid Ethyl Ester A mixture of Example 2 (0.05 g, 0.108 mmol), morpholine (0.023 g, 0.24 mmol), Pd₂(dba)₃ (0.002 g), BINAP (0.0035 g) and sodium tert-butoxide (0.017 g) in 5 mL of toluene heated to 90° C. and stirred for 18 hours. After cooling, the mixture was filtered through diatomaceous earth, concentrated under reduced pressure and purified by flash chromatography using a gradient of ethyl acetate (0-50%) in DCM to provide the titled compound. ¹H NMR (CDCl₃) δ ppm 1.31 (3H), 2.20 (3H), 2.80 (3H), 3.1 (4H), 3.70 (4H), 4.25 (2H), 6.71 (2H), 6.80 (1H), 7.30-7.90 (6H); MS (ESI) m/z 469 (M+H).

Example 19

2-methyl-5-(4-pentyl-phenyl)-1-(4-sulfamoyl-phenyl)-1H-pyrrole-3-carboxylic Acid Ethyl Ester

Example 19A 3-oxo-2-[2-oxo-2-(4-pentyl-phenyl)-ethyl]-butyric Acid Ethyl Ester The titled compound was obtained according to the procedure described in Example 1A substituting 2-bromo-1-(4-pentylphenyl)ethan-1-one for 2,4'-dibromoacetophenone. MS (DCI) m/z 319 (M+H), 336 (M+NH$_4$).

Example 19B 2-methyl-5-(4-pentyl-phenyl)-1-(4-sulfamoyl-phenyl)-1H-pyrrole-3-carboxylic Acid Ethyl Ester The titled compound was obtained according to the procedure described in Example 1B substituting Example 19A for Example 1A. $^1$H NMR (CDCl$_3$) δ ppm 0.90-1.32 (6H), 1.35 (3H), 1.66 (2H), 2.30 (3H), 2.62 (3H), 3.80 (2H), 4.38 (2H), 6.85 (1H), 7.18 (2H), 7.40 (2H), 7.52-7.93 (4H); MS (ESI) m/z 455 (M+H).

Example 20

5-(4-chloro-phenyl)-2-methyl-1-[4-(piperidine-1-sulfonyl)-phenyl]-1H-pyrrole-3-carboxylic Acid Ethyl Ester

Example 20A

2-[2-(4-Chloro-phenyl)-2-oxo-ethyl]-3-oxo-butyric Acid Ethyl Ester

The titled compound was obtained according to the procedure described in Example 1A substituting 2-bromo-1-(4-chloro-phenyl)-ethanone for 2,4'-dibromoacetophenone. $^1$H NMR (CDCl$_3$) δ ppm 1.31 (3H), 2.20 (3H), 3.32 (2H), 3.75 (1H), 4.05 (2H), 7.35 (2H), 7.83 (2H); MS (ESI) m/z 283 (M+H).

Example 20B 5-(4-chloro-phenyl)-2-methyl-1-[4-(piperidine-1-sulfonyl)-phenyl]-1H-pyrrole-3-carboxylic Acid Ethyl Ester The titled compound was obtained according to the procedure described in Example 1B substituting Example 20A for Example 1A and 4-(piperidine-1-sulfonyl)-phenylamine for 4-aminobenzenesulfonamide. $^1$H NMR (CDCl$_3$) δ ppm 1.30 (3H), 1.55 (6H), 2.25 (3H), 2.42 (4H), 4.20 (2H), 6.89 (1H), 7.30-7.44 (4H), 7.49-7.92 (4H); MS (ESI) m/z 487 (M+H).

Example 21

5-(4-chloro-phenyl)-1-(4-dimethylsulfamoyl-phenyl)-2-methyl-1H-pyrrole-3-carboxylic Acid Ethyl Ester The titled compound was obtained according to the procedure described in Example 1B substituting Example 20A for Example 1A and substituting 4-amino-N,N-dimethyl-benzenesulfonamide for 4-aminobenzenesulfonamide. $^1$H NMR (CDCl$_3$) δ ppm 1.31 (3H), 2.15 (3H), 2.47 (6H), 4.29 (2H), 6.90 (1H), 7.33-7.82 (8H); MS (ESI) m/z 447 (M+H).

Example 22

5-(4-chloro-phenyl)-2-methyl-1-[3-(pyrrolidine-1-sulfonyl)-phenyl]-1H-pyrrole-3-carboxylic Acid Ethyl Ester The titled compound was obtained according to the procedure described in Example 1B substituting Example 20A for Example 1A and substituting 3-(pyrrolidine-1-sulfonyl)-phenylamine for 4-aminobenzenesulfonamide. $^1$H NMR (CDCl$_3$) δ ppm 1.29 (3H), 1.60 (4H), 2.18 (3H), 2.85 (4H), 4.35 (2H), 6.99 (1H), 7.30-7.80 (8H); MS (ESI) m/z 473 (M+H).

Example 23 ethyl 5-(4-chlorophenyl)-2-methyl-1-[3-(piperidin-1-ylsulfonyl)phenyl]-1H-pyrrole-3-carboxylate The titled compound was obtained according to the procedure described in Example 1B substituting Example 20A for Example 1A and substituting 3-(piperidine-1-sulfonyl)-phenylamine for 4-aminobenzenesulfonamide. $^1$H NMR (CDCl$_3$) δ ppm 1.29 (3H), 1.60 (6H), 2.40 (3H), 2.85 (4H), 4.35 (2H), 6.99 (1H), 7.30-7.80 (8H); MS (ESI) m/z 487 (M+H).

Example 24 ethyl 1-[3-(aminosulfonyl)phenyl]-5-(4-chlorophenyl)-2-methyl-1H-pyrrole-3-carboxylate The titled compound was obtained according to the procedure described in Example 1B substituting Example 20A for Example 1A and substituting 3-amino-benzenesulfonamide for 4-aminobenzenesulfonamide. $^1$H NMR (CDCl$_3$) δ ppm 1.33 (3H), 2.15 (3H), 3.40 (2H), 4.25 (2H), 6.82 (1H), 7.30-7.982 (8H); MS (ESI) m/z 419 (M+H).

Example 25 ethyl 5-(4-chlorophenyl)-2-methyl-1-(4-nitrophenyl)-1H-pyrrole-3-carboxylate

The titled compound was obtained according to the procedure described in Example 1B substituting Example 20A for Example 1A and substituting 4-amino-nitrobenzene for 4-aminobenzenesulfonamide. $^1$H NMR (CDCl$_3$) δ ppm 1.30 (3H), 2.20 (3H), 4.00 (2H), 6.52-7.00 (5H), 7.33-7.45 (4H); MS (ESI) m/z 385 (M+H).

Example 26

1-(4-amino-phenyl)-5-(4-chloro-phenyl)-2-methyl-1H-pyrrole-3-carboxylic Acid Ethyl Ester To a suspension of Example 25 (0.09 g, 0.234 mmol) in ethanol (5 mL) at −15° C. was added a solution of SnCl$_2$ (0.22 g, 1.172 mmol) in HCl (conc., 1 mL). The mixture was heated to 60° C. for 30 minutes. After cooling, the mixture was basified to a pH 12 with an aqueous solution of KOH (50%) and extracted with DCM (100 mL). The combined organic phases were dried over sodium sulfate, filtered and concentrated under reduced pressure to provide the titled compound. $^1$H NMR (CDCl$_3$) δ ppm 1.30 (3H), 2.20 (3H), 4.29 (2H), 6.93 (1H), 7.30-8.20 (8H); MS (ESI) m/z 355 (M+H).

Example 27

1-(4-azido-phenyl)-5-(4-chloro-phenyl)-2-methyl-1H-pyrrole-3-carboxylic Acid Ethyl Ester A solution of NaNO$_2$ (0.015 g, 0.216 mmol) in water (1.5 mL) was added to an ice-cold solution of Example 26 (0.075 g, 0.212 mmol) in HCl (3 mL, 37% w/v) over 10 minutes. A solution of NaN$_3$ (0.138 g, 2.12 mmol) in water (0.5 mL) was added drop wise with stirring at 0° C. over 10 minutes, and the temperature of the mixture was allowed to rise to 25° C. After stirring for another 20 minutes at room temperature, the mixture was extracted with DCM (3×25 mL), and the combined organic extracts were dried (Na$_2$SO$_4$), filtered and concentrated under reduced pressure to provide the titled compound. MS (ESI) m/z 381 (M+H); IR: 2097 cm$^{-1}$.

Example 28

5-(4-chloro-phenyl)-2-methyl-1-(4-sulfamoyl-phenyl)-1H-pyrrole-3-carboxylic Acid Ethyl Ester The titled compound was obtained according to the procedure described in Example 1B substituting Example 20A for Example 1A. $^1$H NMR (CDCl$_3$) δ ppm 1.31 (3H), 2.25 (3H), 3.42 (2H), 4.20 (2H), 6.89 (1H), 7.30-7.44 (4H), 7.49-7.92 (4H); MS (ESI) m/z 419 (M+H).

Example 29 sodium 5-(4-chloro-phenyl)-2-methyl-1-(4-sulfamoyl-phenyl)-1H-pyrrole-3-carboxylate Example 28 (4.0 g, 9.55 mmol) and aqueous NaOH (5 M, 10 mL) in 50 mL of ethanol was heated to reflux for 20 hours. After cooling the precipitate was separated by filtration and washed twice with 15 mL of ethanol and dried to supply the product as the disodium salt. $^1$H NMR (D$_2$O) δ ppm 2.16 (3H), 3.40 (2H), 6.29 (1H), 7.33-7.42 (4H), 7.53-7.98 (4H); MS (ESI) m/z 389/391. Alternatively:

Example 28 (4.19 g, 10 mmol) was suspended in ethanol (50 mL) and treated with 5 M aqueous NaOH (10 mL). The mixture was heated at reflux for 80 minutes. The suspension was filtered to collect a beige solid which was rinsed with ethanol, stirred thoroughly in 1:1 EtOAc/CH$_2$Cl$_2$, recollected by filtration, and rinsed with more 1:1 EtOAc/CH$_2$Cl$_2$. The solid was dried under vacuum to give the product as the disodium salt. MS (ESI: negative ion detection) m/z 389/391. $^1$H NMR (300 MHz, DMSO-d$_6$) δ ppm 7.67 (d, 2H), 7.20 (d, 2H), 7.07 (d, 2H), 6.98 (d, 2H), 6.54 (s, 1H), 2.32 (s, 3H).

The disodium salt (0.94 g) was partitioned between EtOAc and 0.5 M aq. aqueous HCl (10 mL) with stirring. Hexanes was added and the biphasic mixture was thoroughly stirred. The organic phase was separated, washed with water, dried over Na$_2$SO$_4$, and concentrated to provide the free acid.

Example 30

5-(4-chloro-phenyl)-1-[4-(dimethylaminomethylene-sulfamoyl)-phenyl]-2-methyl-1H-pyrrole-3-carboxylic acid N-methoxy-N-methyl-amide Example 30A 5-(4-chloro-phenyl)-1-[4-(dimethylaminomethylene-sulfamoyl)-phenyl]-2-methyl-1H-pyrrole-3-carbonyl Chloride Oxalyl chloride (2 M in DCM, 3.84 mL) was added drop wise at 0° C. to a solution of Example 29 (1.5 g, 3.84 mmol) in DCM (25 mL)/DMF (0.5 mL). Mixture was stirred for 3 hours after which the mixture was concentrated under reduced pressure and used directly for the next step. MS (ESI) m/z 464.

Example 30B 5-(4-chloro-phenyl)-1-[4-(dimethylaminomethylene-sulfamoyl)-phenyl]-2-methyl-1H-pyrrole-3-carboxylic acid N-methoxy-N-methyl-amide To a cold (0° C.) mixture of Example 30A (1.9 g, 4.64 mmol) and N,O-dimethylhydroxylamine hydrochloride (0.5 g, 5.11 mmol) in DCM (50 mL) was added TEA (1.62 mL, 11.6 mmol). The mixture was stirred at room temperature for five hours after which the solvents were removed under reduced pressure and the residue purified by chromatography using a mixture of DCM:methanol (95:5) to obtain the titled compound. $^1$H NMR (CDCl$_3$) δ ppm 2.20 (3H), 2.47 (6H), 2.74 (3H), 3.39 (3H), 6.20 (1H), 7.33-7.42 (4H), 7.50-7.90 (5H); MS (ESI) m/z 489 (M+H).

General Procedure B

To a solution of an N-methyl N-methoxy carboxylic acid amide (a Weinreb amide such as Example 30 or Example 40) (0.075 g, 0.153 mmol) in dry THF (5 mL) at room temperature was added a Grignard reagent (5 eq). The mixture was heated to reflux and monitored by TLC. Upon completion (as determined by TLC) the mixture was cooled and was quenched by careful addition of a solution of ammonium chloride (saturated, 2 mL), water (5 mL) and extracted with DCM (3×30 mL). The combined organic phase was dried over sodium sulfate, filtered and concentrated under reduced pressure and the residue was purified by chromatography using either DCM or a mixture of DCM:EtOAc (4:1).

Example 31

4-[5-(4-chloro-phenyl)-2-methyl-3-propionyl-pyrrol-1-yl]-benzenesulfonamide

The titled compound was obtained according to General Procedure B using Example 30 and ethylmagnesium bromide (1.0 M in THF). $^1$H NMR (CDCl$_3$) δ ppm 1.20 (3H), 2.20 (3H), 2.45 (2H), 3.39 (2H), 6.95 (1H), 7.33-7.90 (8H); MS (ESI) m/z 403 (M+H).

Example 32

4-[5-(4-chloro-phenyl)-3-isobutyryl-2-methyl-pyrrol-1-yl]-benzenesulfonamide

The titled compound was obtained according to General Procedure B using Example 30 and isopropylmagnesium chloride (2.0 M in THF). $^1$H NMR (CDCl$_3$) δ ppm 1.23 (6H), 2.26 (3H), 2.70 (1H), 3.45 (2H), 6.85 (1H), 7.33-7.90 (8H); MS (ESI) m/z 417 (M+H).

Example 33

4-[5-(4-chloro-phenyl)-3-cyclopropanecarbonyl-2-methyl-pyrrol-1-yl]-benzenesulfonamide The titled compound was obtained according to General Procedure B using Example 30 and cyclopropylmagnesium bromide (0.50 M in THF). $^1$H NMR (CDCl$_3$) δ ppm 0.75 (4H), 1.10 (1H), 2.26 (3H), 4.85 (2H), 6.85 (1H), 7.05-7.95 (8H); MS (ESI) m/z 415 (M+H).

Example 34

4-[5-(4-chloro-phenyl)-2-methyl-3-(4-methyl-benzoyl)-pyrrol-1-yl]-benzenesulfonamide The titled compound was obtained according to General Procedure B using Example 30 and p-tolylmagnesium bromide (1.0 M in THF). $^1$H NMR (CDCl$_3$) δ ppm 2.26 (3H), 2.35 (3H), 3.55 (2H), 6.75 (1H), 7.25-7.92 (12H); MS (ESI) m/z 465 (M+H).

Example 35

4-[3-(4-chloro-3-methyl-benzoyl)-5-(4-chloro-phenyl)-2-methyl-pyrrol-1-yl]-benzenesulfonamide The titled compound was obtained according to General Procedure B using Example 30 and 4-chloro-3-methylphenylmagnesium bromide (1.0 M in THF). $^1$H NMR (CDCl$_3$) δ ppm 2.20 (3H), 2.30 (3H), 3.80 (2H), 6.90 (1H), 7.34-7.92 (11H); MS (ESI) m/z 499.

Example 36

4-[3-(4-chloro-benzoyl)-5-(4-chloro-phenyl)-2-methyl-pyrrol-1-yl]-benzenesulfonamide The titled compound was obtained according to General Procedure B using Example 30 and 4-chlorophenylmagnesium bromide (1.0 M in THF). $^1$H NMR (CDCl$_3$) δ ppm 2.16 (3H), 3.72 (2H), 6.95 (1H), 7.33-7.99 (12H); MS (ESI) m/z 486 (M+H).

Example 37

4-[5-(4-chloro-phenyl)-3-(5-fluoro-2-methoxy-benzoyl)-2-methyl-pyrrol-1-yl]-benzenesulfonamide The titled compound was obtained according to General Procedure B using Example 30 and 5-fluoro-2-methoxyphenylmagnesium bromide (0.5 M in THF). $^1$H NMR (CDCl$_3$) δ ppm 2.22 (3H), 3.70 (3H), 3.80 (2H), 6.90 (1H), 6.95 (1H), 7.15-7.92 (10H); MS (ESI) m/z 499 (M+H).

Example 38 ethyl 5-(4-chlorophenyl)-2-methyl-1-(3-(methylsulfonyl)phenyl)-1H-pyrrole-3-carboxylate The titled compound was obtained according to the procedure described in Example 1B substituting Example 20A for Example 1A and substituting 3-methylsulfonyl-phenylamine for 4-aminobenzenesulfonamide. $^1$H NMR (CDCl$_3$) δ ppm 1.35 (3H), 2.18 (3H), 2.75 (3H), 4.27 (2H), 6.99 (1H), 7.33-7.90 (8H); MS (ESI) m/z 418 (M+H).

Example 39

5-(4-chloro-phenyl)-1-(3-methanesulfonyl-phenyl)-2-methyl-1H-pyrrole-3-carboxylic acid Example 38 (0.47 g, 1.13 mmol), NaOH (5 M, 1.14 mL) in 30 mL of ethanol was heated to reflux for 20 hours and then cooled to ambient temperature. The pH of the solution was adjusted to 4 (HCl, 6 M) after which it was extracted with DCM (3×100 mL). The combined organic phases were dried (Na$_2$SO$_4$), filtered and the organic phase was concentrated under reduced pressure to provide the titled compound. $^1$H NMR (CDCl$_3$) δ ppm 2.15 (3H), 2.65 (3H), 6.25 (1H), 7.38-7.85 (8H); MS (ESI) m/z 390 (M+H).

Example 40

5-(4-chloro-phenyl)-1-(3-methanesulfonyl-phenyl)-2-methyl-1H-pyrrole-3-carboxylic Acid Methoxymethyl Amide

Example 40A 5-(4-chloro-phenyl)-1-(3-methanesulfonyl-phenyl)-2-methyl-1H-pyrrole-3-carbonyl Chloride The titled compound was obtained according to the procedure described in Example 30A substituting Example 39 for Example 29. MS (DCI) m/z 408.

Example 40B 5-(4-chloro-phenyl)-1-(3-methanesulfonyl-phenyl)-2-methyl-1H-pyrrole-3-carboxylic Acid N-methoxy-N-methyl Amide The titled compound was obtained according to the procedure described in Example 30B substituting Example 40A for Example 30A. $^1$H NMR (CDCl$_3$) δ ppm 2.19 (3H), 2.60 (3H), 2.75 (3H), 3.40 (3H), 6.50 (1H), 7.33-7.85 (8H); MS (ESI) m/z 433 (M+H).

Example 41

1-[5-(4-chloro-phenyl)-1-(3-methanesulfonyl-phenyl)-2-methyl-1H-pyrrol-3-yl]propan-1-one The titled compound was obtained according to General Procedure B using Example 40 and ethylmagnesium bromide (1 M in THF). $^1$H NMR (CDCl$_3$) δ ppm 1.20 (3H), 2.18 (3H), 2.45 (2H), 2.75 (3H), 6.70 (1H), 7.33-7.90 (8H); MS (ESI) m/z 402 (M+H).

Example 42 ethyl 2-methyl-1-(3-(methylsulfonyl)phenyl)-5-phenyl-1H-pyrrole-3-carboxylate The titled compound was obtained according to the procedures described in Example 1 substituting acetophenone for 2,4'-dibromoacetophenone in Example 1A and 3-(methylsulfonyl)aniline for 4-aminobenzenesulfonamide in Example 1B. $^1$H NMR (CDCl$_3$) δ ppm 1.30 (3H), 2.18 (3H), 2.45 (3H), 4.29 (2H), 6.80 (1H), 7.20-7.90 (9H); MS (ESI) m/z 384 (M+H).

Example 43

5-(4-chloro-phenyl)-1-(3-ethanesulfonyl-phenyl)-2-methyl-1H-pyrrole-3-carboxylic Acid Ethyl Ester

Example 43A

1-ethanesulfonyl-3-nitro-benzene

Potassium nitrate (4.46 g, 44.12 mmol) was added portion wise to a solution of ethylphenyl sulfone in concentrated HCl (25 mL) at room temperature; then the mixture was heated to reflux for one hour. After cooling, the mixture was poured onto ice and the precipitate was collected by filtration. The solid was washed with cold water (2×50 mL) and dried. $^1$H NMR (CDCl$_3$) δ ppm 1.28 (3H), 3.45 (2H), 7.80 (1H), 8.21 (1H), 8.30 (1H), 8.85 (1H); MS (DCI) m/z 216 (M+H).

Example 43B

3-ethanesulfonyl-phenylamine

Example 43A (0.6 g, 2.78 mmol) was suspended in ethanol (35 mL) at 0° C. then a solution of SnCl$_2$ (2.64 g, 13.9 mmol) in HCl (concentrated, 10 mL) was added. The mixture was heated at 60° C. for 30 minutes and cooled to ambient temperature. The pH of the mixture was adjusted to a pH 12 using an aqueous solution of KOH (50%), and extracted with DCM (3×100 mL). The combined organic phases were dried over sodium sulfate, filtered and concentrated to dryness to provide the titled compound. $^1$H NMR (CDCl$_3$) δ ppm 1.27 (3H), 3.49 (2H), 4.6 (2H), 7.00-7.40 (4H); MS (DCI) m/z 186 (M+H).

Example 43C

5-(4-chloro-phenyl)-1-(3-ethanesulfonyl-phenylamine)-2-methyl-1H-pyrrole-3-carboxylic Acid Ethyl Ester The titled compound was obtained according to the procedure described in Example 1B substituting Example 20A for Example 1A and 3-ethanesulfonyl-phenylamine for 4-aminobenzenesulfonamide. $^1$H NMR (CDCl$_3$) δ ppm 1.28 (3H), 1.32 (3H), 2.18 (3H), 3.45 (2H), 4.20 (2H), 6.89 (1H), 7.33-7.90 (8H); MS (ESI) m/z 432 (M+H).

Example 44

1-(3-ethanesulfonyl-phenylamine)-2-methyl-5-phenyl-1H-pyrrole-3-carboxylic Acid Ethyl Ester The titled compound was obtained according to the procedures described in Example 1 substituting acetophenone for 2,4'-dibromoacetophenone in Example 1A and 3-ethane sulfonyl-phenylamine for 4-aminobenzenesulfonamide in Example 1B. $^1$H NMR (CDCl$_3$) δ ppm 1.25 (3H), 1.30 (3H), 2.16 (3H), 3.45 (2H), 4.20 (2H), 6.89 (1H), 7.25-7.90 (9H); MS (ESI) m/z 398 (M+H).

Example 45

2-methyl-5-phenyl-1-[3-(propane-2-sulfonyl)-phenyl]-1H-pyrrole-3-carboxylic Acid Ethyl Ester The titled compound was obtained according to the procedure described in Example 1 substituting acetophenone for 2,4'-dibromoacetophenone in Example 1A and 3-(propane-2-sulfonyl)-phenylamine for 4-aminobenzenesulfonamide in Example 1B. $^1$H NMR (CDCl$_3$) δ ppm 1.33 (3H), 1.33 (6H), 2.18 (3H), 3.34 (1H), 4.20 (2H), 6.80 (1H), 7.20-7.80 (9H); MS (ESI) m/z 412 (M+H).

Example 46

5-(4-chloro-phenyl)-1-(3-methanesulfonyl-phenyl)-2-phenyl-1H-pyrrole-3-carboxylic Acid Ethyl Ester

Example 46A

2-benzoyl-4-(4-chloro-phenyl)-4-oxo-butyric Acid Ethyl Ester

The titled compound was obtained according to the procedure described in Example 1A substituting 2-bromo-1-(4-chloro-phenyl)-ethanone for 2,4'-dibromoacetophenone and substituting 3-oxo-3-phenyl-propionic acid ethyl ester for ethyl acetoacetate. $^1$H NMR (CDCl$_3$) δ ppm 1.31 (3H), 3.10 (2H), 4.12 (2H), 4.45 (1H), 7.35-7.89 (9H); MS (ESI) m/z 345 (M+H).

Example 46B

5-(4-chloro-phenyl)-1-(3-methanesulfonyl-phenyl)-2-phenyl-1H-pyrrole-3-carboxylic Acid Ethyl Ester The titled compound was obtained according to the procedure described in Example 1B substituting Example 46A for Example 1A and substituting 3-methanesulfonyl-phenylamine for 4-aminobenzenesulfonamide. $^1$H NMR (CDCl$_3$) δ ppm 1.30 (3H), 2.85 (3H), 4.29 (2H), 6.90 (1H), 7.22-7.90 (13H); MS (ESI) m/z 480 (M+H).

Example 47

5-(4-chloro-phenyl)-2-(4-fluoro-phenyl)-1-(3-methanesulfonyl-phenyl)-1H-pyrrole-3-carboxylic Acid Ethyl Ester

Example 47A

4-(4-chloro-phenyl)-2-(4-fluoro-benzoyl)-4-oxo-butyric acid ethyl ester

The titled compound was obtained according to the procedure described in Example 1A substituting 2-bromo-1-(4-chloro-phenyl)-ethanone for 2,4'-dibromoacetophenone and substituting 3-(4-fluoro-phenyl)-3-oxo-propionic acid ethyl ester for ethyl acetoacetate. $^1$H NMR (CDCl$_3$) δ ppm 1.30 (3H), 3.05 (2H), 4.12 (2H), 4.45 (1H), 7.05-7.85 (8H); MS (ESI) m/z 363 (M+H).

Example 47B 5-(4-chloro-phenyl)-2-(4-fluoro-phenyl)-1-(3-methanesulfonyl-phenyl)-1H-pyrrole-3-carboxylic Acid Ethyl Ester The titled compound was obtained according to the procedure described in Example 1B substituting Example 47A for Example 1A and substituting 3-methanesulfonyl-phenylamine for 4-aminobenzenesulfonamide. $^1$H NMR (CDCl$_3$) δ ppm 1.27 (3H), 2.84 (3H), 4.23 (2H), 6.92 (1H), 7.02-7.90 (12H); MS (ESI) m/z 498 (M+H).

Example 48

5-(4-chloro-phenyl)-2-(2-fluoro-phenyl)-1-(3-methanesulfonyl-phenyl)-1H-pyrrole-3-carboxylic Acid Ethyl Ester

Example 48A 4-(4-chloro-phenyl)-2-(2-fluoro-benzoyl)-4-oxo-butyric Acid Ethyl Ester The titled compound was obtained according to the procedure described in Example 1A substituting 2-bromo-1-(4-chloro-phenyl)-ethanone for 2,4'-dibromoacetophenone and substituting 3-(2-fluoro-phenyl)-3-oxo-propionic acid ethyl ester for ethyl acetoacetate. $^1$H NMR (CDCl$_3$) δ ppm 1.30 (3H), 3.05 (2H), 4.12 (2H), 4.45 (1H), 7.00-7.80 (8H); MS (ESI) m/z 363 (M+H).

Example 48B 5-(4-chloro-phenyl)-2-(2-fluoro-phenyl)-1-(3-methanesulfonyl-phenyl)-1H-pyrrole-3-carboxylic Acid Ethyl Ester The titled compound was obtained according to the procedure described in Example 1B substituting Example 48A for Example 1A and substituting 3-methanesulfonyl-phenylamine for 4-aminobenzenesulfonamide. $^1$H NMR (CDCl$_3$) δ ppm 1.34 (3H), 2.80 (3H), 4.29 (2H), 6.90 (1H), 7.02-7.90 (12H); MS (ESI) m/z 498 (M+H).

Example 49

5-(4-chloro-phenyl)-2-ethyl-1-(3-methanesulfonyl-phenyl)-1H-pyrrole-3-carboxylic Acid Ethyl Ester

Example 49A

2-[2-(4-chloro-phenyl)-2-oxo-ethyl]-3-oxo-pentanoic acid ethyl ester

The titled compound was obtained according to the procedure described in Example 1A substituting 2-bromo-1-(4-chloro-phenyl)-ethanone for 2,4'-dibromoacetophenone and substituting 3-oxo-pentanoic acid ethyl ester for ethyl acetoacetate. $^1$H NMR (CDCl$_3$) δ ppm 1.10 (3H), 1.30 (3H), 2.49 (2H), 3.18 (2H), 3.70 (1H), 4.12 (2H), 7.35-7.80 (4H); MS (ESI) m/z 297 (M+H).

Example 49B 5-(4-chloro-phenyl)-2-ethyl-1-(3-methanesulfonyl-phenyl)-1H-pyrrole-3-carboxylic Acid Ethyl Ester The titled compound was obtained according to the procedure described in Example 1B substituting Example 49A for Example 1A and substituting 3-methanesulfonyl-phenylamine for 4-aminobenzenesulfonamide. $^1$H NMR (CDCl$_3$) δ ppm 1.20 (3H), 1.34 (3H), 2.55 (2H), 2.83 (3H), 4.30 (2H), 6.81 (1H), 7.30-7.80 (8H); MS (ESI) m/z 432 (M+H).

Example 50

5-(4-chloro-phenyl)-1-(3-methanesulfonyl-phenyl)-2-methyl-1H-pyrrole-3-carboxylic Acid Benzyl Ester

Example 50A

2-[2-(4-chloro-phenyl)-2-oxo-ethyl]-3-oxo-butyric Acid Benzyl Ester

The titled compound was obtained according to the procedure described in Example 1A substituting 2-bromo-1-(4-chloro-phenyl)-ethanone for 2,4'-dibromoacetophenone and substituting 3-oxo-butyric acid benzyl ester for ethyl acetoacetate. $^1$H NMR (CDCl$_3$) δ ppm 2.10 (3H), 3.18 (2H), 3.72 (1H), 5.12 (2H), 7.25-7.83 (9H); MS (ESI) m/z 345 (M+H).

Example 50B 5-(4-chloro-phenyl)-1-(3-methanesulfonyl-phenyl)-2-methyl-1H-pyrrole-3-carboxylic Acid Benzyl Ester The titled compound was obtained according to the procedure described in Example 1B substituting Example 50A for Example 1A and substituting 3-methanesulfonyl-phenylamine for 4-aminobenzenesulfonamide. $^1$H NMR (CDCl$_3$) δ ppm 2.20 (3H), 2.85 (3H), 5.50 (2H), 6.85 (1H), 7.20-7.80 (13H); MS (ESI) m/z 480 (M+H).

General Procedure C

A mixture of aldehyde, vinyl ketone (1.1 eq), 3-ethyl-5-(2-hydroxyethyl)-4-methylthiazolium bromide (0.15 eq) and TEA (1.5 eq) were heated in ethanol (2.5 M) at reflux for 20 hours. After cooling, the mixture was diluted with DCM and washed with a solution of NH$_4$Cl and then with aqueous sodium bicarbonate (10% solution), dried using sodium sulfate, filtered and concentrated under reduced pressure. The residue was typically purified by flash chromatography using a gradient of ethyl acetate (0-40%) in DCM.

General Procedure D 1,4-Dione obtained from General Procedure C, an amine (1.3 eq) and p-toluenesulfonic acid (0.05 eq) were heated in toluene at reflux for 24 hours. After cooling, the mixture was diluted with DCM and washed with a solution of HCl (1 M) and sodium bicarbonate (10% solution), dried using sodium sulfate, filtered and concentrated under reduced pressure. The residue may be purified by chromatography eluting with a gradient of ethyl acetate (0-40%) in DCM.

Example 51

1-(4-methanesulfonyl-phenyl)-2-methyl-5-phenyl-1H-pyrrole

Example 51A

1-phenyl-pentane-1,4-dione

The titled compound was obtained according to the procedure described in General Procedure C using benzaldehyde and but-3-en-2-one. $^1$H NMR (CDCl$_3$) δ ppm 2.10 (3H), 2.63 (2H), 2.85 (2H), 7.30-7.80 (5H); MS (DCI) m/z 177 (M+H).

Example 51B

1-(4-methanesulfonyl-phenyl)-2-methyl-5-phenyl-1H-pyrrole

The titled compound was obtained according to the procedure described in General Procedure δ using Example 51A and p-methanesulfonyl phenylamine. $^1$H NMR (CDCl$_3$) δ ppm 2.15 (3H), 2.83 (3H), 6.10 (1H), 6.20 (1H), 7.22-7.98 (9H); MS (ESI) m/z 312 (M+H).

Example 52

1-(3-methanesulfonyl-phenyl)-2-methyl-5-phenyl-1H-pyrrole

The titled compound was obtained according to the procedure described in General Procedure D using Example 51A and m-methanesulfonyl phenylamine. $^1$H NMR (CDCl$_3$) δ ppm 2.18 (3H), 2.80 (3H), 6.12 (1H), 6.24 (1H), 7.22-7.98 (9H); MS (ESI) m/z 312 (M+H).

Example 53

1-(3-ethanesulfonyl-phenyl)-2-methyl-5-phenyl-1H-pyrrole

The titled compound was obtained according to the procedure described in General Procedure D using Example 51A and m-ethanesulfonyl phenylamine. $^1$H NMR (CDCl$_3$) δ ppm 1.30 (3H), 2.16 (3H), 3.45 (2H), 6.10 (1H), 6.25 (1H), 7.25-7.99 (9H); MS (ESI) m/z 326 (M+H).

Example 54

4-(2-methyl-5-phenyl-pyrrol-1-yl)-benzenesulfonamide

The titled compound was obtained according to the procedure described in General Procedure D using Example 51A and p-amino-benzenesulfonamide. $^1$H NMR (CDCl$_3$) δ ppm 2.15 (3H), 4.00 (2H), 6.10 (1H), 6.20 (1H), 7.20-7.98 (9H); MS (ESI) m/z 313 (M+H).

Example 55

2-(4-chloro-phenyl)-1-(4-methanesulfonyl-phenyl)-5-methyl-1H-pyrrole

Example 55A

1-(4-chloro-phenyl)-pentane-1,4-dione

The titled compound was obtained according to the procedure described in General Procedure C using 4-chloro-benzaldehyde and but-3-en-2-one. $^1$H NMR (CDCl$_3$) δ ppm 2.15 (3H), 2.60 (2H), 2.87 (2H), 7.35-7.83 (4H); MS (DCI) m/z 211 (M+H).

Example 55B

2-(4-chloro-phenyl)-1-(4-methanesulfonyl-phenyl)-5-methyl-1H-pyrrole

The titled compound was obtained according to the procedure described in General Procedure D using Example 55A and p-methanesulfonyl phenylamine. $^1$H NMR (CDCl$_3$) δ ppm 2.15 (3H), 2.83 (3H), 6.10 (1H), 6.20 (1H), 7.22-7.98 (8H); MS (ESI) m/z 346 (M+H).

Example 56

2-(4-chloro-phenyl)-1-(3-ethanesulfonyl-phenyl)-5-methyl-1H-pyrrole

The titled compound was obtained according to the procedure described in General Procedure D using Example 55A and m-ethanesulfonyl phenylamine. $^1$H NMR (CDCl$_3$) δ ppm 1.28 (3H), 2.16 (3H), 3.40 (2H), 6.14 (1H), 6.22 (1H), 7.35-7.95 (8H); MS (ESI) m/z 360 (M+H).

Example 57

2-(4-chloro-phenyl)-5-methyl-1-[3-(propane-2-sulfonyl)-phenyl]-1H-pyrrole

The titled compound was obtained according to the procedure described in General Procedure D using Example 55A and m-isopropylsulfonyl phenylamine. $^1$H NMR (CDCl$_3$) δ ppm 1.28 (6H), 2.16 (3H), 3.40 (1H), 6.14 (1H), 6.22 (1H), 7.35-7.95 (8H); MS (ESI) m/z 374 (M+H).

Example 58

2-(4-chloro-phenyl)-1-(3-methanesulfonyl-phenyl)-5-methyl-1H-pyrrole

The titled compound was obtained according to the procedure described in General Procedure D using Example 55A and m-methylsulfonyl phenylamine. $^1$H NMR (CDCl$_3$) δ ppm 2.16 (3H), 2.85 (3H), 6.04 (1H), 6.20 (1H), 7.35-7.95 (8H); MS (ESI) m/z 346 (M+H).

Example 59

4-[2-(4-chloro-phenyl)-5-methyl-pyrrol-1-yl]-benzenesulfonamide

The titled compound was obtained according to the procedure described in General Procedure D using Example 55A and p-aminosulfonyl phenylamine. $^1$H NMR (CDCl$_3$) δ ppm 2.10 (3H), 4.05 (2H), 6.12 (1H), 6.17 (1H), 7.30-7.90 (8H); MS (ESI) m/z 347 (M+H).

Example 60

2-(4-chloro-phenyl)-5-methyl-1-(4-methylsulfanyl-phenyl)-1H-pyrrole

The titled compound was obtained according to the procedure described in General Procedure D using Example 55A and p-methylsulfanyl phenylamine. ¹H NMR (CDCl₃) δ ppm 2.15 (3H), 2.50 (3H), 6.15 (1H), 6.29 (1H), 7.20-7.40 (8H); MS (ESI) m/z 314 (M+H).

Example 61

2-(4-chloro-phenyl)-5-methyl-1-(4-trifluoromethyl-sulfanyl-phenyl)-1H-pyrrole

The titled compound was obtained according to the procedure described in General Procedure D using Example 55A and p-trifluoromethylsulfanyl phenylamine. ¹H NMR (CDCl₃)₆ ppm 2.15 (3H), 6.10 (1H), 6.19 (1H), 7.22-7.50 (8H); MS (ESI) m/z 368 (M+H).

Example 62

5-[2-(4-chloro-phenyl)-5-methyl-pyrrol-1-yl]-2-methyl-benzothiazole

The titled compound was obtained according to the procedure described in General Procedure D using Example 55A and 2-methyl-benzothiazol-5-ylamine. ¹H NMR (CDCl₃) δ ppm 2.19 (3H), 2.75 (3H), 6.14 (1H), 6.25 (1H), 7.32-8.20 (7H); MS (ESI) m/z 339 (M+H).

Example 63

1-{4-[2-(4-chloro-phenyl)-5-methyl-pyrrol-1-yl]-benzenesulfonyl}-piperidine

The titled compound was obtained according to the procedure described in General Procedure D using Example 55A and p-piperidinylsulfonyl phenylamine. ¹H NMR (CDCl₃) δ ppm 1.40-1.60 (6H), 2.20 (3H), 2.92 (4H), 6.18 (1H), 6.35 (1H), 7.03-7.90 (8H); MS (ESI) m/z 415 (M+H).

Example 65

4-[2-(4-chloro-phenyl)-5-methyl-pyrrol-1-yl]-N-methyl-benzenesulfonamide

The titled compound was obtained according to the procedure described in General Procedure D using Example 55A and p-amino-N-methylsulfonyl phenylamine. ¹H NMR (CDCl₃) δ ppm 2.20 (3H), 2.45 (3H), 3.05 (1H), 6.15 (1H), 6.25 (1H), 7.33-7.82 (8H); MS (ESI) m/z 361 (M+H).

Example 66

4-[2-(4-Fluoro-phenyl)-5-methyl-pyrrol-1-yl]-benzenesulfonamide

Example 66A 1-(4-fluoro-phenyl)-pentane-1,4-dione

The titled compound was obtained according to the procedure described in General Procedure C using 4-fluoro-benzaldehyde and but-3-en-2-one. ¹H NMR (CDCl₃) δ ppm 2.15 (3H), 2.60 (2H), 2.87 (2H), 7.05-7.87 (4H); MS (DCI) m/z 195 (M+H).

Example 66B

4-[2-(4-fluoro-phenyl)-5-methyl-pyrrol-1-yl]-benzenesulfonamide

The titled compound was obtained according to the procedure described in General Procedure D using Example 66A and p-aminosulfonyl phenylamine. ¹H NMR (CDCl₃) δ ppm 2.18 (3H), 4.71 (2H), 6.13 (1H), 6.34 (1H), 7.05-7.90 (8H); MS (ESI) m/z 331 (M+H).

Example 67

3-[2-(4-fluoro-phenyl)-5-methyl-pyrrol-1-yl]-benzenesulfonamide

The titled compound was obtained according to the procedure described in General Procedure D using Example 66A and m-aminosulfonyl phenylamine. ¹H NMR (CDCl₃) δ ppm 2.18 (3H), 2.50 (2H), 6.10 (1H), 6.22 (1H), 7.03-7.90 (8H); MS (ESI) m/z 331 (M+H).

Example 68

4-[2-(4-fluoro-phenyl)-5-methyl-pyrrol-1-yl]-N,N-dimethyl-benzenesulfonamide

The titled compound was obtained according to the procedure described in General Procedure D using Example 66A and p-amino-N,N-dimethylsulfonyl phenylamine. ¹H NMR (CDCl₃) δ ppm 2.18 (3H), 2.47 (6H), 6.10 (1H), 6.30 (1H), 7.03-7.90 (8H); MS (ESI) m/z 359 (M+H).

Example 69

4-[2-(4-fluoro-phenyl)-5-methyl-pyrrol-1-yl]-N-methyl-benzenesulfonamide

The titled compound was obtained according to the procedure described in General Procedure D using Example 66A and p-amino-N-methylsulfonyl phenylamine. ¹H NMR (CDCl₃)₆ ppm 2.16 (3H), 2.40 (3H), 3.95 (1H), 6.05 (1H), 6.35 (1H), 7.03-7.82 (8H); MS (ESI) m/z 345 (M+H).

Example 70

4-[2-methyl-5-(3-trifluoromethyl-phenyl)-pyrrol-1-yl]-benzenesulfonamide

Example 70A 1-(3-trifluoromethyl-phenyl)-pentane-1,4-dione

The titled compound was obtained according to the procedure described in General Procedure C using 3-trifluoromethyl-benzaldehyde and but-3-en-2-one. ¹H NMR (CDCl₃) δ ppm 2.12 (3H), 2.68 (2H), 2.81 (2H), 7.27-8.00 (4H); MS (DCI) m/z 245 (M+H).

Example 70B

4-[2-methyl-5-(3-trifluoromethyl-phenyl)-pyrrol-1-yl]-benzenesulfonamide

The titled compound was obtained according to the procedure described in General Procedure D using Example 70A and p-aminosulfonyl phenylamine. $^1$H NMR (CDCl$_3$) δ ppm 2.17 (3H), 4.09 (2H), 6.10 (1H), 6.27 (1H), 7.25-7.90 (8H); MS (ESI) m/z 381 (M+H).

Example 71

3-[2-methyl-5-(3-trifluoromethyl-phenyl)-pyrrol-1-yl]-benzenesulfonamide

The titled compound was obtained according to the procedure described in General Procedure D using Example 70A and m-aminosulfonyl phenylamine. $^1$H NMR (CDCl$_3$) δ ppm 2.14 (3H), 3.00 (2H), 6.10 (1H), 6.27 (1H), 7.25-7.90 (8H); MS (ESI) m/z 381 (M+H).

Example 72

N,N-dimethyl-4-[2-methyl-5-(3-trifluoromethyl-phenyl)-pyrrol-1-yl]-benzenesulfonamide The titled compound was obtained according to the procedure described in General Procedure D using Example 70A and p-amino-N,N-dimethylsulfonyl phenylamine. $^1$H NMR (CDCl$_3$) δ ppm 2.10 (3H), 2.52 (6H), 6.18 (1H), 6.25 (1H), 7.23-7.90 (8H); MS (ESI) m/z 409 (M+H).

Example 73

N-methyl-4-[2-methyl-5-(3-trifluoromethyl-phenyl)-pyrrol-1-yl]-benzenesulfonamide The titled compound was obtained according to the procedure described in General Procedure D using Example 70A and p-amino-N-methylsulfonyl phenylamine. $^1$H NMR (CDCl$_3$) δ ppm 2.17 (3H), 2.40 (3H), 3.45 (1H), 6.01 (1H), 6.19 (1H), 7.23-7.80 (8H); MS (ESI) m/z 395 (M+H).

Example 74

4-(2-methyl-5-o-tolyl-pyrrol-1-yl)-benzenesulfonamide

Example 74A 1-o-tolyl-pentane-1,4-dione

The titled compound was obtained according to the procedure described in General Procedure C using 2-methylbenzaldehyde and but-3-en-2-one. $^1$H NMR (CDCl$_3$) δ ppm 2.12 (3H), 2.35 (3H), 2.65 (2H), 2.81 (2H), 7.14-7.77 (4H); MS (m/z) 191 (M+H).

Example 74B 4-(2-methyl-5-o-tolyl-pyrrol-1-yl)-benzenesulfonamide

The titled compound was obtained according to the procedure described in General Procedure D using Example 74A and p-aminosulfonyl phenylamine. $^1$H NMR (CDCl$_3$) δ ppm 2.15 (3H), 2.35 (3H), 4.50 (2H), 6.10 (1H), 6.20 (1H), 7.15-7.90 (8H); MS (ESI) m/z 327 (M+H).

Example 75

4-(2-Biphenyl-4-yl-5-methyl-pyrrol-1-yl)-benzenesulfonamide

Example 75A 1-biphenyl-4-yl-pentane-1,4-dione

The titled compound was obtained according to the procedure described in General Procedure C using 4-biphenylcarboxaldehyde and but-3-en-2-one. $^1$H NMR (CDCl$_3$) δ ppm 2.08 (3H), 2.65 (2H), 2.83 (2H), 7.22-7.97 (9H); MS (DCI) m/z 253 (M+H).

Example 75B 4-(2-biphenyl-4-yl-5-methyl-pyrrol-1-yl)-benzenesulfonamide

The titled compound was obtained according to the procedure described in General Procedure D using Example 75A and p-aminosulfonyl phenylamine. $^1$H NMR (CDCl$_3$) δ ppm 2.20 (3H), 4.09 (2H), 6.18 (1H), 6.29 (1H), 7.22-7.90 (13H); MS (ESI) m/z 389 (M+H).

Example 76

4-(2-methyl-5-m-tolyl-pyrrol-1-yl)-benzenesulfonamide

Meta-methylbenzaldehyde and but-3-en-2-one were treated according to the procedure outlined in General Procedure C followed by subjecting the resulting product to conditions outlined in General Procedure D along with p-aminosulfonyl phenylamine to obtain the titled compound. $^1$H NMR (CDCl$_3$) δ ppm 2.15 (3H), 2.05 (3H), 4.90 (2H), 6.10 (1H), 6.30 (1H), 6.89-7.90 (8H); MS (ESI) m/z 327 (M+H).

Example 77

4-[2-(2,4-dichloro-phenyl)-5-methyl-pyrrol-1-yl]-benzenesulfonamide 2,4-Dichlorobenzaldehyde and but-3-en-2-one were treated according to the procedure outlined in General Procedure C followed by subjecting the resulting product to conditions outlined in General Procedure D along with p-aminosulfonyl phenylamine to obtain the titled compound. $^1$H NMR (CDCl$_3$) δ ppm 2.20 (3H), 4.82 (2H), 6.12 (1H), 6.35 (1H), 7.15-7.90 (8H); MS (ESI) m/z 381/383.

Example 78

1-{4-[2-(2,4-dichloro-phenyl)-5-methyl-pyrrol-1-yl]-benzenesulfonyl}-piperidine 2,4-Dichlorobenzaldehyde and but-3-en-2-one were treated according to the procedure outlined in General Procedure C followed by subjecting the resulting product to conditions outlined in General Procedure D along with p-piperidinylsulfonyl phenylamine to obtain the titled compound. $^1$H NMR (CDCl$_3$) δ ppm 1.50 (6H), 2.10 (3H), 2.80 (4H), 6.08 (1H), 6.35 (1H), 7.33-7.90 (7H); MS (ESI) m/z 449/451 (M+H).

Example 79

4-[2-(2,4-dichloro-phenyl)-5-methyl-pyrrol-1-yl]-N-methyl-benzenesulfonamide 2,4-Dichlorobenzaldehyde and but-3-en-2-one were treated according to the procedure outlined in General Procedure C followed by subjecting the resulting product to conditions outlined in General Procedure D along with p-amino-N-methylsulfonyl phenylamine to obtain the titled compound. $^1$H NMR (CDCl$_3$) δ ppm 2.20 (3H), 2.65 (3H), 4.25 (1H), 6.15 (1H), 6.25 (1H), 7.03-7.82 (7H); MS (ESI) m/z 395/397 (M+H).

Example 80

4-[2-(4-bromo-phenyl)-5-methyl-pyrrol-1-yl]-benzenesulfonamide

4-Bromobenzaldehyde and but-3-en-2-one were treated according to the procedure outlined in General Procedure C followed by subjecting the resulting product to conditions outlined in General Procedure D along with p-aminosulfonyl phenylamine to obtain the titled compound. $^1$H NMR (CDCl$_3$) δ ppm 2.15 (3H), 4.81 (2H), 6.15 (1H), 6.29 (1H), 6.95-7.85 (8H); MS (ESI) m/z 391/393 (M+H)

Example 81

3-[2-(4-bromo-phenyl)-5-methyl-pyrrol-1-yl]-N-methyl-benzenesulfonamide

4-Bromobenzaldehyde and but-3-en-2-one were treated according to the procedure outlined in General Procedure C followed by subjecting the resulting product to conditions outlined in General Procedure D along with m-amino-N-methylsulfonyl phenylamine to obtain the titled compound. $^1$H NMR (CDCl$_3$) δ ppm 2.15 (3H), 2.65 (3H), 4.28 (1H), 6.15 (1H), 6.35 (1H), 6.85-7.82 (8H); MS (ESI) m/z 405/407 (M+H).

Example 82

1-{4-[2-(3-bromo-phenyl)-5-methyl-pyrrol-1-yl]-benzenesulfonyl}-piperidine

3-Bromobenzaldehyde and but-3-en-2-one were treated according to the procedure outlined in General Procedure C followed by subjecting the resulting product to conditions outlined in General Procedure D along with p-piperidinylsulfonyl phenylamine to obtain the titled compound. $^1$H NMR (CDCl$_3$) δ ppm 1.45-1.60 (6H), 2.18 (3H), 3.05 (4H), 6.18 (1H), 6.40 (1H), 7.05-7.90 (8H); MS (ESI) m/z 459/461 (M+H).

Example 83

1-{4-[2-(2-fluoro-phenyl)-5-methyl-pyrrol-1-yl]-benzenesulfonyl}-piperidine

2-Fluorobenzaldehyde and but-3-en-2-one were treated according to the procedure outlined in General Procedure C followed by subjecting the resulting product to conditions outlined in General Procedure D along with p-piperidinylsulfonyl phenylamine to obtain the titled compound. $^1$H NMR (CDCl$_3$) δ ppm 1.42-1.65 (6H), 2.15 (3H), 2.95 (4H), 6.15 (1H), 6.40 (1H), 6.65-7.90 (8H); MS (ESI) m/z 399 (M+H).

Example 84

4-[2-(2-fluoro-phenyl)-5-methyl-pyrrol-1-yl]-benzenesulfonamide

2-Fluorobenzaldehyde and but-3-en-2-one were treated according to the procedure outlined in General Procedure C followed by subjecting the resulting product to conditions outlined in General Procedure D along with p-aminosulfonyl phenylamine to obtain the titled compound. $^1$H NMR (CDCl$_3$) δ ppm 2.18 (3H), 4.71 (2H), 6.13 (1H), 6.34 (1H), 7.05-7.90 (8H); MS (ESI) m/z 331 (M+H).

Example 85

1-{4-[2-(2-fluoro-phenyl)-5-methyl-pyrrol-1-yl]-benzenesulfonyl}-piperidine

2-Fluorobenzaldehyde and but-3-en-2-one were treated according to the procedure outlined in General Procedure C followed by subjecting the resulting product to conditions outlined in General Procedure D along with p-piperidinylsulfonyl phenylamine to obtain the titled compound. $^1$H NMR (CDCl$_3$) δ ppm 1.50 (6H), 2.21 (3H), 2.85 (4H), 6.15 (1H), 6.25 (1H), 7.03-7.90 (8H); MS (ESI) m/z 399 (M+H).

Example 86

4-[2-(3-fluoro-phenyl)-5-methyl-pyrrol-1-yl]-N-methyl-benzenesulfonamide

3-Fluorobenzaldehyde and but-3-en-2-one were treated according to the procedure outlined in General Procedure C followed by subjecting the resulting product to conditions outlined in General Procedure D along with m-amino-N-methylsulfonyl phenylamine to obtain the titled compound. $^1$H NMR (CDCl$_3$) δ ppm 2.15 (3H), 2.65 (3H), 4.20 (1H), 6.15 (1H), 6.40 (1H), 6.65-7.85 (8H); MS (ESI) m/z 345 (M+H).

Example 87

4-[2-(2-chloro-phenyl)-5-methyl-pyrrol-1-yl]-N-methyl-benzenesulfonamide

2-Chlorobenzaldehyde and but-3-en-2-one were treated according to the procedure outlined in General Procedure C followed by subjecting the resulting product to conditions outlined in General Procedure D along with m-amino-N-methylsulfonyl phenylamine to obtain the titled compound. $^1$H NMR (CDCl$_3$) δ ppm 2.20 (3H), 2.65 (3H), 4.25 (1H), 6.15 (1H), 6.35 (1H), 7.03-7.75 (8H); MS (ESI) m/z 361 (M+H).

Example 88

4-[2-(3-chloro-phenyl)-5-methyl-pyrrol-1-yl]-N,N-dimethyl-benzenesulfonamide

3-Chlorobenzaldehyde and but-3-en-2-one were treated according to the procedure outlined in General Procedure C followed by subjecting the resulting product to conditions outlined in General Procedure D along with p-amino-N,N-dimethylsulfonyl phenylamine to obtain the titled compound. $^1$H NMR (CDCl$_3$) δ ppm 2.15 (3H), 2.52 (6H), 6.18 (1H), 6.35 (1H), 7.00-7.90 (8H); MS (ESI) m/z 375 (M+H).

Example 89

1-{4-[2-(3-chloro-phenyl)-5-methyl-pyrrol-1-yl]-benzenesulfonyl}-piperidine

3-Chlorobenzaldehyde and but-3-en-2-one were treated according to the procedure outlined in General Procedure C followed by subjecting the resulting product to conditions outlined in General Procedure D along with p-piperidinylsulfonyl phenylamine to obtain the titled compound. $^1$H NMR (CDCl$_3$) δ ppm 1.42-1.65 (6H), 2.18 (3H), 3.00 (4H), 6.18 (1H), 6.40 (1H), 6.85-7.90 (8H); MS (ESI) m/z 415 (M+H).

Example 90

4-[2-(3-chloro-phenyl)-5-methyl-pyrrol-1-yl]-N-methyl-benzenesulfonamide

3-Chlorobenzaldehyde and but-3-en-2-one were treated according to the procedure outlined in General Procedure C followed by subjecting the resulting product to conditions outlined in General Procedure D along with m-amino-N-methylsulfonyl phenylamine to obtain the titled compound. $^1$H NMR (CDCl$_3$) δ ppm 2.15 (3H), 2.62 (3H), 4.25 (1H), 6.15 (1H), 6.39 (1H), 6.85-7.90 (8H); MS (ESI) m/z 361 (M+H).

Example 91

N-methyl-4-(2-methyl-5-m-tolyl-pyrrol-1-yl)-benzenesulfonamide

3-Methylbenzaldehyde and but-3-en-2-one were treated according to the procedure outlined in General Procedure C followed by subjecting the resulting product to conditions outlined in General Procedure D along with p-amino-N-methylsulfonyl phenylamine to obtain the titled compound. $^1$H NMR (CDCl$_3$) δ ppm 2.18 (3H), 2.30 (3H), 2.48 (3H), 3.45 (1H), 6.11 (1H), 6.29 (1H), 7.03-7.82 (8H); MS (ESI) m/z 341 (M+H).

Example 92

5-(4-chloro-phenyl)-1-(4-methanesulfonyl-phenyl)-2-methyl-1H-pyrrole-3-carboxaldehyde To a solution of Example 55 (1.0 g, 2.9 mmol) in DMF (2.2 mL, 29 mmol) and toluene (15 mL) was added POCl$_3$ over a period of 15 minutes. After stirring another 20 minutes, the mixture was heated for 5 hours at 70° C. After cooling, the mixture was poured over a cold solution of aqueous sodium acetate (50 mL, 20%), extracted with EtOAc (3×100 mL) and the combined organic phases were washed with a solution of aqueous sodium bicarbonate (150 mL, 10%), water (150 mL) and brine (150 mL). The solution was dried with sodium sulfate, filtered, concentrated under reduced pressure and the residue was purified by flash chromatography (DCM). $^1$H NMR (CDCl$_3$) δ ppm 2.15 (3H), 2.80 (3H), 6.20 (1H), 7.35-7.95 (8H), 9.65 (1H); MS (ESI) m/z 374 (M+H).

Examples 93A and 93B

4-[5-(4-chloro-phenyl)-3-iodo-2-methyl-pyrrol-1-yl]-benzenesulfonamide (93A) and 4-[2-(4-chloro-phenyl)-3,4-diiodo-5-methyl-pyrrol-1-yl]-benzenesulfonamide (93B)

To a solution of the disodium salt of Example 29 (2.07 g, 4.76 mmol) in DMF (30 mL) and water (7.5 mL) cooled with an ice bath was added iodine (2.67 g, 10.5 mmol) over 10 minutes, and the resulting solution stirred cold for 20 minutes and another 45 minutes at ambient temperature. The mixture was quenched with 10% aqueous Na$_2$S$_2$O$_3$ (25 mL) and partitioned between 0.1 M aqueous KH$_2$PO$_4$ and 2:1 EtOAc/hexanes. The layers were separated and the aqueous phase (pH~7) was extracted with additional 2:1 EtOAc/hexanes (2×). The combined organic phases were washed with water, dried (Na$_2$SO$_4$) and filtered and concentrated onto silica. The resulting powder was placed atop an Alltech silica column (average pore size 60 Å, particle size 50 μM) and chromatographed (0→10% EtOAc/CH$_2$Cl$_2$). The obtained material was boiled in MeOH (120 mL), hot filtered with a hot MeOH rinse, returned to boiling, treated with water (6 mL), and permitted to cool overnight. The resulting white powder was collected by filtration and dried under vacuum to provide the monoiodo compound, Example 93A. $^1$H NMR (400 MHz, DMSO-d$_6$) δ ppm 7.86 (d, 2H), 7.46 (bs, 2H), 7.42 (d, 2H), 7.26 (d, 2H), 7.02 (d, 2H), 6.56 (s, 1H), 2.08 (s, 3H); MS (DCI) m/z 473/475.

The mother liquor was concentrated and purified twice by preparative HPLC [Waters XTerra RP18 column, 30×100 mm, flow 40 mL/min, 20% for 3 minutes then gradient 20-70% of MeCN in buffer (0.1 M aqueous ammonium bicarbonate, adjusted to pH 10 with concentrated aqueous NH$_4$OH) over 32 min] to provide the diiodo compound, Example 93B. $^1$H NMR (400 MHz, DMSO-d$_6$) δ ppm 7.79 (d, 2H), 7.44 (bs, 2H), 7.40 (d, 2H), 7.34 (d, 2H), 7.16 (d, 2H), 2.16 (s, 3H); MS (ESI: negative ion detection) m/z 597/599.

Example 94

4-[5-(4-chloro-phenyl)-3-(4-hydroxymethyl-phenyl)-2-methyl-pyrrol-1-yl]-benzenesulfonamide The monoiodo compound of Example 93A (29 mg, 0.060 mmol), 4-(hydroxymethyl)phenylboronic acid (14 mg, 0.090 mmol), and palladium acetate (2.2 mg, 0.010 mmol) were suspended into ethanol (0.50 mL) along with 1 M aqueous Cs$_2$CO$_3$ (0.090 mL, 0.090 mmol), then heated in a microwave (Personal Chemistry: Emrys Creator) at 90° C. for 15 minutes and at 100° C. for 10 minutes. The mixture was diluted with EtOAc (2 mL), filtered through diatomaceous earth with an EtOAc rinse. The filtrate was diluted with hexanes (2 mL) and washed with 1 M aqueous NaOH. The organic phase was kept aside, but the gum that formed was separated, dissolved into EtOAc (2 mL), diluted with hexanes (0.5 mL), and washed with water. This second organic phase was combined with the first organic phase, dried (Na$_2$SO$_4$), concentrated, chromatographed (with a drop of acetic acid) on an Alltech silica column (average pore size 60 Å, particle size 50 μM) (30→20% hexanes/Et$_2$O), then rechromatographed similarly (30→10% hexanes/Et$_2$O) to provide the titled compound. $^1$H NMR (500 MHz, DMSO-d$_6$) δ ppm 7.89 (d, 2H), 7.50-7.46 (m, 4H), 7.44 (d, 2H), 7.37 (d, 2H), 7.28 (d, 2H), 7.09 (d, 2H), 6.65 (s, 1H), 5.16 (bs, 1H), 4.52 (s, 2H), 2.18 (s, 3H); MS (ESI: negative ion detection) m/z 451/453.

Example 95

4-[3-benzofuran-2-yl-5-(4-chloro-phenyl)-2-methyl-pyrrol-1-yl]-benzenesulfonamide To a solution of benzofuran-2-ylboronic acid (0.385 mL of 0.2 M in ethanol, 0.077 mmol) was added to a 2 mL microwave vial containing palladium acetate (2.3 mg, 0.010 mmol) followed by 1 M aqueous solution of $Cs_2CO_3$ (0.06 mL) and the monoiodo compound of Example 93A as a solution in ethanol (0.650 mL, 0.027 mmol). The mixture was heated in the microwave at 120° C. for 15 minutes, cooled and filtered through a Si-Carbonate cartridge supplied by Silicycle Chemical Division, and concentrated under reduced pressure. The residue was dissolved in 1:1 DMSO/MeOH and purified by reverse phase HPLC using an acetonitrile/water 0.1% TFA gradient elution method. $^1$H NMR (500 MHz, DMSO-$d_6$/$D_2O$) δ ppm 7.92 (d, 2H), 7.62 (m, 1H), 7.57 (m, 1H), 7.50 (d, 2H), 7.30 (d, 2H), 7.28-7.22 (m, 2H), 7.12 (d, 2H), 6.95 (s, 1H), 6.88 (s, 1H), 2.38 (s, 3H); MS (ESI: negative ion detection) m/z 561 (M−1).

Example 96

5-(4-chloro-phenyl)-4-iodo-2-methyl-1-(4-sulfamoyl-phenyl)-1H-pyrrole-3-carboxylic Acid Ethyl Ester Example 28 (4.19 g, 10 mmol) was dissolved into DMF (20 mL, 0.5 M) and treated portionwise over 15 minutes with iodine (5.33 g, 21.0 mmol). After another 30 minutes the mixture was quenched with 10% aqueous $Na_2S_2O_3$ (50 mL), and partitioned between 2:1 EtOAc/hexanes and water. The aqueous phase was separated and extracted with additional 2:1 EtOAc/hexanes (2×150 mL), and the combined organic phases washed with water, dried ($Na_2SO_4$), and concentrated under reduced pressure. The resulting solid was slurried with $CH_2Cl_2$, filtered, rinsed with more $CH_2Cl_2$, and dried under vacuum to provide a powder. The filtrate was slurried with MeCN, filtered, rinsed with more MeCN, and dried under vacuum. The slurry wash with MeCN was repeated to provide the titled compound as a powder. $^1$H NMR (400 MHz, DMSO-$d_6$) δ ppm 7.81 (d, 2H), 7.46 (bs, 2H), 7.45 (d, 2H), 7.34 (d, 2H), 7.18 (d, 2H), 4.27 (q, 2H), 2.28 (s, 3H), 1.32 (t, 3H); MS (ESI: negative ion detection) m/z 543/545.

Example 97

5-(4-chloro-phenyl)-4-(4-hydroxymethyl-phenyl)-2-methyl-1-(4-sulfamoyl-phenyl)-1H-pyrrole-3-carboxylic Acid Ethyl Ester To a mixture of Example 96 (33 mg, 0.060 mmol), 4-(hydroxymethyl)phenylboronic acid (12 mg, 0.080 mmol), palladium acetate (2.2 mg, 0.010 mmol) suspended in ethanol (0.50 mL) was added 1 M aqueous $Cs_2CO_3$ (0.080 mL, 0.080 mmol), and heated in a microwave (Personal Chemistry: Emrys Creator) at 110° C. for 15 minutes. The mixture was diluted with $Et_2O$ (2 mL), stirred thoroughly, filtered through diatomaceous earth with $Et_2O$ rinse. The filtrate was washed with 1 M pH 7 potassium phosphate buffer, dried ($Na_2SO_4$), filtered and concentrated under reduced pressure and the residue chromatographed on an Alltech silica column (average pore size 60 Å, particle size 50 μM) (30→10% hexanes/$Et_2O$) to provide a white foam. $^1$H NMR (300 MHz, DMSO-$d_6$) δ ppm 7.81 (d, 2H), 7.49 (d, 2H), 7.48 (bs, 2H), 7.14 (d, 2H), 7.14 (d, 2H), 7.06 (d, 2H), 6.95 (d, 2H), 5.10 (t, 1H), 4.45 (d, 2H), 4.02 (q, 2H), 2.32 (s, 3H), 1.0 (t, 3H); MS (ESI) m/z m/z 525/527.

General Procedure E

To a solution of a boronic acid (0.593 mL of 0.2 M in ethanol, 0.12 mmol) in a 2 mL microwave vial containing (3.3 mg, 0.015 mmol) palladium acetate was added a 1 M aqueous solution of $Cs_2CO_3$ (0.091 mL) and Example 96 as a solution in ethanol (0.471 mL, 0.065 mmol). The vial was sealed and heated in a microwave at 120° C. for 15 minutes. The mixture was then passed through a Si-Carbonate cartridge supplied by Silicycle Chemical Division, and concentrated under reduced pressure. The residues dissolved in 1:1 DMSO/MeOH were purified by reverse phase HPLC using an acetonitrile/water 0.1% TFA gradient elution method.

Example 98

5-(4-chloro-phenyl)-2-methyl-4-phenyl-1-(4-sulfamoyl-phenyl)-1H-pyrrole-3-carboxylic Acid Ethyl Ester The titled compound was obtained according to the procedure described in General Procedure E, using phenyl boronic acid. $^1$H NMR (500 MHz, DMSO-$d_6$/$D_2O$) δ ppm 7.84 (d, 2H), 7.48 (d, 2H), 7.25-7.10 (m, 7H), 6.96 (d, 2H), 4.00 (q, 2H), 2.33 (s, 3H), 0.97 (t, 3H); MS (ESI) m/z 495 (M+1).

Example 99

4-(3-amino-phenyl)-5-(4-chloro-phenyl)-2-methyl-1-(4-sulfamoyl-phenyl)-1H-pyrrole-3-carboxylic Acid Ethyl Ester The titled compound was obtained according to the procedure described in General Procedure E, using 3-aminophenyl boronic acid. $^1$H NMR (500 MHz, DMSO-$d_6$/$D_2O$) δ ppm 7.83 (d, 2H), 7.46 (d, 2H), 7.14 (d, 2H), 6.95 (d, 2H), 6.85 (t, 1H), 6.43-6.38 (m, 2H), 6.28 (d, 1H), 4.01 (q, 2H), 2.31 (s, 3H), 1.01 (t, 3H); MS (ESI) m/z negative ion 508 (M−1).

Example 100

5-(4-chloro-phenyl)-4-(3-hydroxy-phenyl)-2-methyl-1-(4-sulfamoyl-phenyl)-1H-pyrrole-3-carboxylic Acid Ethyl Ester The titled compound was obtained according to the procedure described in General Procedure E, using 3-hydroxyphenyl boronic acid. $^1$H NMR (500 MHz, DMSO-$d_6$/$D_2O$) δ ppm 7.82 (d, 2H), 7.45 (d, 2H), 7.14 (d, 2H), 7.00 (t, 1H), 6.95 (d, 2H), 6.59 (d, 1H), 6.57-6.51 (m, 2H), 4.02 (q, 2H), 2.32 (s, 3H), 1.00 (t, 3H); MS (ESI) m/z negative ion 509 (M−1).

Example 101

5-(4-chloro-phenyl)-4-(3-methoxy-phenyl)-2-methyl-1-(4-sulfamoyl-phenyl)-1H-pyrrole-3-carboxylic Acid Ethyl Ester The titled compound was obtained according to the procedure described in General Procedure E, using 3-methoxyphenyl boronic acid. $^1$H NMR (500 MHz, DMSO-$d_6$/$D_2O$) δ ppm 7.84 (d, 2H), 7.48 (d, 2H), 7.18-7.11 (m, 3H), 6.99 (d, 2H), 6.77 (d, 1H), 6.70-6.66 (m, 2H), 4.02 (q, 2H), 3.64 (s, 3H), 2.32 (s, 3H), 0.99 (t, 3H); MS (ESI) m/z negative ion 523 (M−1).

Example 102

5-(4-chloro-phenyl)-4-(3-chloro-phenyl)-2-methyl-1-(4-sulfamoyl-phenyl)-1H-pyrrole-3-carboxylic Acid Ethyl Ester The titled compound was obtained according to the procedure described in General Procedure E, using 3-chlorophenyl boronic acid. $^1$H NMR (500 MHz, DMSO-$d_6$/$D_2$O) δ ppm 7.84 (d, 2H), 7.48 (d, 2H), 7.26-7.22 (m, 2H), 7.20-7.15 (m, 3H), 7.04 (d, 1H), 6.98 (d, 2H), 4.03 (q, 2H), 2.34 (s, 3H), 1.01 (t, 3H); MS (ESI) m/z negative ion 527 (M−1).

Example 103

4,5-bis-(4-chloro-phenyl)-2-methyl-1-(4-sulfamoyl-phenyl)-1H-pyrrole-3-carboxylic Acid Ethyl Ester The titled compound was obtained according to the procedure described in General Procedure E, using 4-chlorophenyl boronic acid. $^1$H NMR (500 MHz, DMSO-$d_6$/$D_2$O) δ ppm 7.84 (d, 2H), 7.48 (d, 2H), 7.28 (d, 2H), 7.17 (d, 2H), 7.14 (d, 2H), 6.96 (d, 2H), 4.03 (q, 2H), 2.33 (s, 3H), 1.01 (t, 3H); MS (ESI) m/z negative ion 527 (M−1).

Example 104

5-(4-chloro-phenyl)-4-(3-cyano-phenyl)-2-methyl-1-(4-sulfamoyl-phenyl)-1H-pyrrole-3-carboxylic Acid Ethyl Ester The titled compound was obtained according to the procedure described in General Procedure E, using 3-cyanophenyl boronic acid. $^1$H NMR (500 MHz, DMSO-$d_6$/$D_2$O) δ ppm 7.85 (d, 2H), 7.66 (m, 1H), 7.59 (m, 1H), 7.43 (d, 2H), 7.44-7.41 (m, 2H), 7.18 (d, 2H), 6.99 (d, 2H), 4.03 (q, 2H), 2.35 (s, 3H), 0.99 (t, 3H); MS (ESI) m/z negative ion 518 (M−1).

Example 105

5-(4-chloro-phenyl)-4-(4-cyano-phenyl)-2-methyl-1-(4-sulfamoyl-phenyl)-1H-pyrrole-3-carboxylic Acid Ethyl Ester The titled compound was obtained according to the procedure described in General Procedure E, using 4-cyanophenyl boronic acid. $^1$H NMR (500 MHz, DMSO-$d_6$/$D_2$O) δ ppm 7.84 (d, 2H), 7.68 (d, 2H), 7.49 (d, 2H), 7.32 (d, 2H), 7.18 (d, 2H), 6.98 (d, 2H), 4.03 (q, 2H), 2.34 (s, 3H), 0.99 (t, 3H).

Example 106

4-(3-acetyl-phenyl)-5-(4-chloro-phenyl)-2-methyl-1-(4-sulfamoyl-phenyl)-1H-pyrrole-3-carboxylic Acid Ethyl Ester The titled compound was obtained according to the procedure described in General Procedure E, using 3-acetylphenyl boronic acid. $^1$H NMR (500 MHz, DMSO-$d_6$/$D_2$O) δ ppm 7.84 (d, 2H), 7.78 (m, 1H), 7.72 (m, 1H), 7.49 (d, 2H), 7.40-7.35 (m, 2H), 7.16 (d, 2H), 7.00 (d, 2H), 4.01 (q, 2H), 2.49 (s, 3H), 2.35 (s, 3H), 0.95 (t, 3H).

Example 107

4-benzo[1,3]dioxol-5-yl-5-(4-chloro-phenyl)-2-methyl-1-(4-sulfamoyl-phenyl)-1H-pyrrole-3-carboxylic Acid Ethyl Ester The titled compound was obtained according to the procedure described in General Procedure E, using 5-benzo[1,3]dioxolyl boronic acid. $^1$H NMR (500 MHz, DMSO-$d_6$/$D_2$O) δ ppm 7.83 (d, 2H), 7.46 (d, 2H), 7.17 (d, 2H), 6.97 (d, 2H), 6.74 (d, 1H), 6.69 (d, 1H), 6.54 (d, 1H), 5.95 (s, 2H), 4.04 (q, 2H), 2.32 (s, 3H), 1.04 (t, 3H); MS (ESI) m/z negative ion 537 (M−1).

Example 108

5-(4-chloro-phenyl)-4-(3,5-dichloro-phenyl)-2-methyl-1-(4-sulfamoyl-phenyl)-1H-pyrrole-3-carboxylic Acid Ethyl Ester The titled compound was obtained according to the procedure described in General Procedure E, using 3,5-dichlorophenyl boronic acid. $^1$H NMR (500 MHz, DMSO-$d_6$/$D_2$O) δ ppm 7.85 (d, 2H), 7.47 (d, 2H), 7.42 (t, 1H), 7.21 (d, 2H), 7.14 (d, 2H), 7.02 (d, 2H), 4.06 (q, 2H), 2.34 (s, 3H), 1.04 (t, 3H); MS (ESI) m/z negative ion 563 (M+1).

Example 109

5-(4-chloro-phenyl)-4-furan-3-yl-2-methyl-1-(4-sulfamoyl-phenyl)-1H-pyrrole-3-carboxylic Acid Ethyl Ester The titled compound was obtained according to the procedure described in General Procedure E, using 3-furyl boronic acid. $^1$H NMR (500 MHz, DMSO-$d_6$/$D_2$O) δ ppm 7.82 (d, 2H), 7.51 (m, 1H), 7.45 (d, 2H), 7.38 (m, 1H), 7.23 (d, 2H), 7.07 (d, 2H), 6.27 (m, 1H), 4.14 (q, 2H), 2.30 (s, 3H), 1.16 (t, 3H); MS (ESI) m/z negative ion 483 (M−1).

Example 110

5-(4-chloro-phenyl)-2-methyl-1-(4-sulfamoyl-phenyl)-4-thiophen-3-yl-1H-pyrrole-3-carboxylic Acid Ethyl Ester The titled compound was obtained according to the procedure described in General Procedure E, using 3-thienyl boronic acid. $^1$H NMR (500 MHz, DMSO-$d_6$/$D_2$O) δ ppm 7.83 (d, 2H), 7.46 (d, 2H), 7.36 (d, 1H), 7.18 (d, 2H), 7.07 (m, 1H), 7.00 (d, 2H), 6.90 (d, 1H), 4.06 (q, 2H), 2.31 (s, 3H), 1.03 (t, 3H); MS (ESI) m/z negative ion 499 (M−1).

Example 111

4-benzofuran-2-yl-5-(4-chloro-phenyl)-2-methyl-1-(4-sulfamoyl-phenyl)-1H-pyrrole-3-carboxylic Acid Ethyl Ester The titled compound was obtained according to the procedure described in General Procedure E, using 2-benzofuryl boronic acid. $^1$H NMR (500 MHz, DMSO-$d_6$/$D_2$O) δ ppm 7.86 (d, 2H), 7.55-7.50 (m, 3H), 7.44 (d, 1H), 7.27-7.12 (m, 6H), 6.63 (m, 1H), 4.05 (q, 2H), 2.34 (s, 3H), 0.91 (t, 3H); MS (ESI) m/z negative ion 533 (M−1).

Example 112

5-(4-chloro-phenyl)-2-methyl-4-(3-nitro-phenyl)-1-(4-sulfamoyl-phenyl)-1H-pyrrole-3-carboxylic Acid Ethyl Ester The titled compound was obtained according to the procedure described in General Procedure E, using 3-nitrophenyl boronic acid. $^1$H NMR (500 MHz, DMSO-d$_6$/D$_2$O) δ ppm 8.08 (m, 1H), 7.98 (m, 1H), 7.86 (d, 2H), 7.57-7.49 (m, 4H), 7.18 (d, 2H), 7.02 (d, 2H), 4.04 (q, 2H), 2.36 (s, 3H), 0.97 (t, 3H); MS (ESI) m/z negative ion 538 (M−1).

Example 113

5-(4-chloro-phenyl)-2-methyl-4-naphthalen-2-yl-1-(4-sulfamoyl-phenyl)-1H-pyrrole-3-carboxylic Acid Ethyl Ester The titled compound was obtained according to the procedure described in General Procedure E, using 2-naphthyl boronic acid. $^1$H NMR (500 MHz, DMSO-d$_6$/D$_2$O) δ ppm 7.89-7.85 (m, 3H), 7.76 (d, 2H), 7.63 (s, 1H), 7.51 (d, 2H), 7.48-7.43 (m, 2H), 7.30 (d, 1H), 7.11 (d, 1H), 7.00 (d, 1H), 3.98 (q, 2H), 2.37 (s, 3H), 0.87 (t, 3H); MS (ESI) m/z negative ion 543 (M−1).

Example 114

5-(4-chloro-phenyl)-4-(4-methanesulfonyl-phenyl)-2-methyl-1-(4-sulfamoyl-phenyl)-1H-pyrrole-3-carboxylic Acid Ethyl Ester The titled compound was obtained according to the procedure described in General Procedure E, using 4-methanesulfonylphenyl boronic acid. $^1$H NMR (500 MHz, DMSO-d$_6$/D$_2$O) δ ppm 7.85 (d, 2H), 7.77 (d, 2H), 7.50 (d, 2H), 7.40 (d, 2H), 7.18 (d, 2H), 7.00 (d, 2H), 4.03 (q, 2H), 3.17 (s, 3H), 2.35 (s, 3H), 0.97 (t, 3H); MS (ESI) m/z negative ion 571 (M−1).

Example 115

5-(4-chloro-phenyl)-4-(1H-indol-4-yl)-2-methyl-1-(4-sulfamoyl-phenyl)-1H-pyrrole-3-carboxylic Acid Ethyl Ester The titled compound was obtained according to the procedure described in General Procedure E, using 4-indolyl boronic acid. $^1$H NMR (500 MHz, DMSO-d$_6$/D$_2$O) δ ppm 7.85 (d, 2H), 7.55-7.45 (m, 2H), 7.25 (d, 1H), 7.19 (m, 1H), 7.03 (d, 2H), 6.95 (d, 1H), 6.89 (d, 2H), 6.71 (d, 1H), 6.09 (m, 1H), 3.78 (q, 2H), 2.37 (s, 3H), 0.62 (t, 3H).

Example 116

5-(4-chloro-phenyl)-4-(3-dimethylamino-phenyl)-2-methyl-1-(4-sulfamoyl-phenyl)-1H-pyrrole-3-carboxylic Acid Ethyl Ester The titled compound was obtained according to the procedure described in General Procedure E, using 3-dimethylaminophenyl boronic acid. $^1$H NMR (500 MHz, DMSO-d$_6$/D$_2$O) δ ppm 7.84 (d, 2H), 7.47 (d, 2H), 7.15 (d, 2H), 7.05-6.95 (m, 3H), 6.56 (d, 1H), 6.48-6.41 (m, 2H), 4.03 (q, 2H), 2.76 (s, 6H), 2.31 (s, 3H), 1.01 (t, 3H); MS (ESI) m/z negative ion 536 (M−1).

Example 117

4-(4-acetylamino-phenyl)-5-(4-chloro-phenyl)-2-methyl-1-(4-sulfamoyl-phenyl)-1H-pyrrole-3-carboxylic Acid Ethyl Ester The titled compound was obtained according to the procedure described in General Procedure E, using 4-acetylaminophenyl boronic acid. $^1$H NMR (500 MHz, DMSO-d$_6$/D$_2$O) δ ppm 7.84 (d, 2H), 7.47 (d, 2H), 7.40 (d, 2H), 7.15 (d, 2H), 7.04 (d, 2H), 6.95 (d, 2H), 4.02 (q, 2H), 2.32 (s, 3H), 2.03 (s, 3H), 1.01 (t, 3H); MS (ESI) m/z negative ion 550 (M−1).

Example 118

5-(4-chloro-phenyl)-4-(4-methanesulfonylamino-phenyl)-2-methyl-1-(4-sulfamoyl-phenyl)-1H-pyrrole-3-carboxylic Acid Ethyl Ester The titled compound was obtained according to the procedure described in General Procedure E, using 4-methylsulfonylaminophenyl boronic acid. $^1$H NMR (500 MHz, DMSO-d$_6$/D$_2$O) δ ppm 7.84 (d, 2H), 7.47 (d, 2H), 7.15 (d, 2H), 7.07 (d, 2H), 7.04 (d, 2H), 6.96 (d, 2H), 4.02 (q, 2H), 2.92 (s, 3H), 2.33 (s, 3H), 0.99 (t, 3H).

Example 119

5-(4-chloro-phenyl)-4-(3-dimethylcarbamoyl-phenyl)-2-methyl-1-(4-sulfamoyl-phenyl)-1H-pyrrole-3-carboxylic Acid Ethyl Ester The titled compound was obtained according to the procedure described in General Procedure E, using 3-(dimethylcarbamoyl)phenylboronic acid. $^1$H NMR (500 MHz, DMSO-d$_6$/D$_2$O) δ ppm 7.85 (d, 2H), 7.49 (d, 2H), 7.32 (d, 1H), 7.24 (m, 1H), 7.22 (m, 1H), 7.15 (d, 2H), 7.03 (m, 1H), 6.96 (d, 2H), 4.03 (q, 2H), 2.92 (s, 3H), 2.66 (s, 3H), 2.35 (s, 3H), 1.00 (s, 3H).

Example 120

5-(4-chloro-phenyl)-4-(4-cyanomethyl-phenyl)-2-methyl-1-(4-sulfamoyl-phenyl)-1H-pyrrole-3-carboxylic Acid Ethyl Ester The titled compound was obtained according to the procedure described in General Procedure E, using 4-(cyanomethyl)benzeneboronic acid. $^1$H NMR (500 MHz, DMSO-d$_6$/D$_2$O) δ ppm 7.84 (d, 2H), 7.48 (d, 2H), 7.20 (d, 2H), 7.16 (d, 2H), 7.15 (d, 2H), 6.98 (d, 2H), 4.03 (q, 2H), 3.70 (s, 2H), 2.33 (s, 3H), 1.00 (s, 3H); MS (ESI) m/z negative ion 532 (M−1).

Example 121

5-(4-chloro-phenyl)-2-methyl-4-[3-(4-methyl-piperazine-1-carbonyl)-phenyl]-1-(4-sulfamoyl-phenyl)-1H-pyrrole-3-carboxylic Acid Ethyl Ester The titled compound was obtained according to the procedure described in General Procedure E, using 3-(4-methyl-piperazine-1-carbonyl)-phenyl boronic acid. $^1$H NMR (500 MHz, DMSO-d$_6$/D$_2$O) δ ppm 7.84 (d, 2H), 7.48 (d, 2H), 7.35-7.25 (m, 2H), 7.21 (d, 1H), 7.16 (d, 2H), 6.94-6.93 (m, 3H), 4.04 (q, 2H), 3.54 (bs, 2H), 3.00 (bs, 2H), 2.34 (s, 3H), 2.29 (bs, 2H), 2.16 (s, 3H), 2.06 (bs, 2H), 1.02 (t, 3H); MS (ESI) m/z positive ion 621 (M+1).

General Procedure F

In a microwave vial containing 3 eq. of PS-DCC, a solution of 5-(4-chloro-phenyl)-2-methyl-1-(4-sulfamoyl-phenyl)-1H-pyrrole-3-carboxylic acid (the free acid of Example 29) (29 mg, 0.06 mmol) in DMA (1.0 mL) was added, followed in succession by a solution of HOBT (8 mg, 0.06 mmol) in MeCN (0.6 mL), and a solution of DIEA (23 mg, 0.18 mmol) in MeCN (0.6 mL). Then a solution of a representative amine (0.07 mmol) in MeCN (0.4 mL) was added. The mixture was heated in the microwave to 100° C. for 10 minutes. The mixture was filtered through a Si-Carbonate cartridge supplied by Silicycle Chemical Division and concentrated to dryness under reduced pressure. The residues were dissolved in 1:1 DMSO/MeOH and purified by reverse phase HPLC (Waters Symmetry C8 column (25 mm×100 mm, 7 um particle size) using a gradient of 10% to 100% acetonitrile: 0.1% aqueous TFA over 8 minutes at a flow rate of 40 mL/minute).

Example 122

5-(4-chloro-phenyl)-2-methyl-1-(4-sulfamoyl-phenyl)-1H-pyrrole-3-carboxylic Acid Isopropylamide The titled compound was obtained according to the procedure described in General Procedure F using 2-aminopropane. $^1$H NMR (500 MHz, DMSO-$d_6$/$D_2O$) δ ppm 1.15 (d, 6H) 2.26-2.36 (m, 3H) 3.97-4.18 (m, 1H) 6.93-6.97 (m, 1H) 7.00-7.07 (m, 2H) 7.24-7.35 (m, 2H) 7.40-7.48 (m, 2H) 7.55-7.65 (m, 1H) 7.85-7.92 (m, 2H); MS (ESI: negative ion detection) m/z 430 (M−1).

Example 123

5-(4-chloro-phenyl)-2-methyl-1-(4-sulfamoyl-phenyl)-1H-pyrrole-3-carboxylic Acid Butylamide The titled compound was obtained according to the procedure described in General Procedure F using 1-aminobutane. $^1$H NMR (500 MHz, DMSO-$d_6$/$D_2O$) δ ppm 0.90 (t, 3H) 1.28-1.39 (m, 2H) 1.43-1.56 (m, 2H) 2.26-2.35 (m, 3H) 3.15-3.25 (m, 2H) 6.85-6.92 (m, 1H) 6.98-7.07 (m, 2H) 7.23-7.35 (m, 2H) 7.38-7.49 (m, 2H) 7.80-7.86 (m, 1H) 7.86-7.91 (m, 2H); MS (ESI: negative ion detection) m/z 444 (M−1).

Example 124

5-(4-chloro-phenyl)-2-methyl-1-(4-sulfamoyl-phenyl)-1H-pyrrole-3-carboxylic Acid (2-methoxyethyl)-amide The titled compound was obtained according to the procedure described in General Procedure F using 2-methoxy-1-aminoethane. $^1$H NMR (500 MHz, DMSO-$d_6$/$D_2O$) δ ppm 2.31-2.35 (m, 3H) 3.26-3.29 (m, 3H) 3.37-3.38 (m, 2H) 3.41-3.45 (m, 2H) 6.90-6.93 (m, 1H) 6.99-7.06 (m, 2H) 7.23-7.33 (m, 2H) 7.40-7.48 (m, 2H) 7.85-7.92 (m, 2H); MS (ESI: negative ion detection) m/z 446 (M−1).

Example 125

5-(4-chloro-phenyl)-2-methyl-1-(4-sulfamoyl-phenyl)-1H-pyrrole-3-carboxylic Acid-(3-propoxy-propyl)-amide The titled compound was obtained according to the procedure described in General Procedure F using 1-amino-3-propoxypropane. $^1$H NMR (500 MHz, DMSO-$d_6$/$D_2O$) δ ppm 0.87 (t, 3H) 1.46-1.57 (m, 2H) 1.69-1.79 (m, 2H) 2.30-2.33 (m, 3H) 3.23-3.29 (m, 2H) 3.30-3.35 (m, 2H) 3.40-3.44 (m, 2H) 6.85-6.90 (m, 1H) 6.97-7.05 (m, 2H) 7.27-7.34 (m, 2H) 7.39-7.47 (m, 2H) 7.81-7.87 (m, 1H) 7.87-7.91 (m, 2H); MS (ESI: negative ion detection) m/z 488 (M−1).

Example 126

5-(4-chloro-phenyl)-2-methyl-1-(4-sulfamoyl-phenyl)-1H-pyrrole-3-carboxylic Acid-(R)-(tetrahydrofuran-2-ylmethyl)-amide The titled compound was obtained according to the procedure described in General Procedure F using (2R)-tetrahydrofuran-2-ylmethanamine. $^1$H NMR (500 MHz, DMSO-$d_6$/$D_2O$) δ ppm 1.53-1.66 (m, 1H) 1.70-1.97 (m, 3H) 2.28-2.35 (m, 3H) 3.23-3.30 (m, 2H) 3.57-3.67 (m, 1H) 3.72-3.83 (m, 1H) 3.85-4.06 (m, 1H) 6.90-6.96 (m, 1H) 6.99-7.06 (m, 2H) 7.24-7.34 (m, 2H) 7.40-7.50 (m, 2H) 7.85-7.90 (m, 2H);

Example 127

5-(4-chloro-phenyl)-2-methyl-1-(4-sulfamoyl-phenyl)-1H-pyrrole-3-carboxylic Acid (tetrahydro-furan-3-ylmethyl)-amide The titled compound was obtained according to the procedure described in General Procedure F using 1-tetrahydrofuran-3-ylmethanamine. $^1$H NMR (500 MHz, DMSO-$d_6$/$D_2O$) δ ppm 1.51-1.69 (m, 1H) 1.85-1.98 (m, 1H) 2.26-2.36 (m, 3H) 2.41-2.48 (m, 1H) 3.11-3.29 (m, 2H) 3.44-3.51 (m, 1H) 3.56-3.65 (m, 1H) 3.65-3.71 (m, 1H) 3.71-3.81 (m, 1H) 6.87-6.93 (m, 1H) 7.00-7.06 (m, 2H) 7.23-7.33 (m, 2H) 7.40-7.51 (m, 2H) 7.81-7.96 (m, 2H); MS (ESI: negative ion detection) m/z 472 (M−1).

Example 128

5-(4-chloro-phenyl)-2-methyl-1-(4-sulfamoyl-phenyl)-1H-pyrrole-3-carboxylic Acid cyclobutylamide The titled compound was obtained according to the procedure described in General Procedure F using cyclobutylamine. $^1$H NMR (500 MHz, DMSO-$d_6$/$D_2O$) δ ppm 1.49-1.72 (m, 2H) 1.99-2.10 (m, 2H) 2.14-2.25 (m, 2H) 2.27-2.33 (m, 3H) 4.20-4.48 (m, 1H) 6.93-6.96 (m, 1H) 7.00-7.05 (m, 2H) 7.23-7.34 (m, 2H) 7.38-7.50 (m, 2H) 7.82-7.92 (m, 2H); MS (ESI: negative ion detection) m/z 442 (M−1).

Example 129

5-(4-chloro-phenyl)-2-methyl-1-(4-sulfamoyl-phenyl)-1H-pyrrole-3-carboxylic Acid Dimethylamide The titled compound was obtained according to the procedure described in General Procedure F using dimethylamine. $^1$H NMR (500 MHz, DMSO-$d_6$/$D_2O$) δ ppm 2.09-2.13 (m, 3H) 2.84-3.24 (m, 6H) 6.52-6.58 (m, 1H) 6.98-7.10 (m, 2H)

7.23-7.31 (m, 2H) 7.41-7.51 (m, 2H) 7.83-7.94 (m, 2H); MS (ESI: negative ion detection) m/z 416 (M−1).

Example 130

5-(4-chloro-phenyl)-2-methyl-1-(4-sulfamoyl-phenyl)-1H-pyrrole-3-carboxylic Acid Ethyl-methyl-amide The titled compound was obtained according to the procedure described in General Procedure F using methylethylamine. $^1$H NMR (500 MHz, DMSO-d$_6$/D$_2$O) δ ppm 1.14 (t, 3H) 2.07-2.10 (m, 3H) 2.81-3.17 (m, 3H) 3.42-3.59 (m, 2H) 6.45-6.54 (m, 1H) 6.97-7.08 (m, 2H) 7.21-7.30 (m, 2H) 7.41-7.51 (m, 2H) 7.81-7.93 (m, 2H); (ESI) m/z negative ion 430 (M−1).

Example 131

5-(4-chloro-phenyl)-2-methyl-1-(4-sulfamoyl-phenyl)-1H-pyrrole-3-carboxylic Acid Isopropyl-methyl-amide The titled compound was obtained according to the procedure described in General Procedure F using isopropyl-methylamine. $^1$H NMR (500 MHz, DMSO-d$_6$/D$_2$O) δ ppm 1.14 (d, 6H) 2.02-2.10 (m, 3H) 2.71-2.99 (m, 3H) 6.40-6.55 (m, 1H) 6.97-7.12 (m, 2H) 7.22-7.34 (m, 2H) 7.36-7.54 (m, 2H) 7.80-7.94 (m, 2H); MS (ESI: negative ion detection) m/z 444 (M−1).

Example 132

4-[5-(4-chloro-phenyl)-2-methyl-3-(pyrrolidine-1-carbonyl)-pyrrol-1-yl]-benzenesulfonamide The titled compound was obtained according to the procedure described in General Procedure F using pyrrolidine. $^1$H NMR (500 MHz, DMSO-d$_6$/D$_2$O) δ ppm 1.81-1.92 (m, 4H) 2.12-2.25 (m, 3H) 3.41-3.54 (m, 2H) 3.55-3.81 (m, 2H) 6.60-6.72 (m, 1H) 6.99-7.09 (m, 2H) 7.21-7.32 (m, 2H) 7.40-7.53 (m, 2H) 7.77-7.97 (m, 2H); MS (ESI: negative ion detection) m/z 442 (M−1).

Example 133

4-[5-(4-chloro-phenyl)-2-methyl-3-(piperidine-1-carbonyl)-pyrrol-1-yl]-benzenesulfonamide The titled compound was obtained according to the procedure described in General Procedure F using piperidine. $^1$H NMR (500 MHz, DMSO-d$_6$/D$_2$O) δ ppm 1.43-1.59 (m, 4H) 1.59-1.73 (m, 2H) 2.08-2.10 (m, 3H) 3.48-3.67 (m, 4H) 6.40-6.54 (m, 1H) 6.98-7.11 (m, 2H) 7.22-7.34 (m, 2H) 7.40-7.52 (m, 2H) 7.77-7.94 (m, 2H); MS (ESI: negative ion detection) m/z 456 (M−1).

Example 134

5-(4-chloro-phenyl)-2-methyl-1-(4-sulfamoyl-phenyl)-1H-pyrrole-3-carboxylic Acid-(2-methoxyethyl)-methyl-amide The titled compound was obtained according to the procedure described in General Procedure F using N-(methoxyethyl)-N-methylamine. $^1$H NMR (500 MHz, DMSO-d$_6$/D$_2$O) δ ppm 2.05-2.10 (m, 3H) 3.20-3.30 (m, 3H) 3.47-3.58 (m, 3H) 3.57-3.69 (m, 3H) 6.49-6.56 (m, 1H) 6.97-7.12 (m, 2H) 7.23-7.31 (m, 2H) 7.40-7.48 (m, 2H) 7.48-7.54 (m, 1H) 7.79-7.97 (m, 2H); MS (ESI: negative ion detection) m/z 460 (M−1).

Example 135

5-(4-chloro-phenyl)-2-methyl-1-(4-sulfamoyl-phenyl)-1H-pyrrole-3-carboxylic Acid-bis-(2-methoxyethyl)-amide The titled compound was obtained according to the procedure described in General Procedure F using N,N-bis(2-methoxyethyl)amine. $^1$H NMR (500 MHz, DMSO-d$_6$/D$_2$O) δ ppm 2.01-2.08 (m, 3H) 3.16-3.30 (m, 6H) 3.45-3.55 (m, 4H) 3.57-3.71 (m, 4H) 6.46-6.56 (m, 1H) 6.93-7.13 (m, 2H) 7.20-7.34 (m, 2H) 7.39-7.48 (m, 2H) 7.78-7.93 (m, 2H); MS (ESI: negative ion detection) m/z 504 (M−1).

Example 136

4-[5-(4-chloro-phenyl)-2-methyl-3-(morpholine-4-carbonyl)-pyrrol-1-yl]-benzenesulfonamide The titled compound was obtained according to the procedure described in General Procedure F using morpholine. $^1$H NMR (500 MHz, DMSO-d$_6$/D$_2$O) δ ppm 2.10-2.13 (m, 3H) 3.56-3.75 (m, 8H) 6.49-6.52 (m, 1H) 7.02-7.09 (m, 2H) 7.22-7.30 (m, 2H) 7.42-7.55 (m, 2H) 7.84-7.94 (m, 2H); MS (ESI: negative ion detection) m/z 458 (M−1).

Example 137

5-(4-chloro-phenyl)-2-methyl-1-(4-sulfamoyl-phenyl)-1H-pyrrole-3-carboxylic Acid Benzylamide The titled compound was obtained according to the procedure described in General Procedure F using benzylamine. $^1$H NMR (500 MHz, DMSO-d$_6$/D$_2$O) δ ppm 2.33-2.35 (m, 3H) 4.39-4.48 (m, 2H) 6.94-6.98 (m, 1H) 7.01-7.06 (m, 2H) 7.20-7.26 (m, 1H) 7.27-7.31 (m, 2H) 7.31-7.36 (m, 4H) 7.42-7.52 (m, 2H) 7.81-7.92 (m, 2H); MS (ESI: negative ion detection) m/z 478 (M−1).

Example 138

5-(4-chloro-phenyl)-2-methyl-1-(4-sulfamoyl-phenyl)-1H-pyrrole-3-carboxylic Acid (pyridin-3-ylmethyl)-amide The titled compound was obtained according to the procedure described in General Procedure F using 3-(aminomethyl)pyridine. $^1$H NMR (500 MHz, DMSO-d$_6$/D$_2$O) δ ppm 2.26-2.38 (m, 3H) 4.35-4.51 (m, 2H) 6.90-6.97 (m, 1H) 7.00-7.06 (m, 2H) 7.24-7.34 (m, 2H) 7.40-7.53 (m, 3H) 7.76-7.84 (m, 1H) 7.84-7.98 (m, 2H) 8.42-8.54 (m, 1H) 8.54-8.62 (m, 1H).

Example 139

5-(4-chloro-phenyl)-2-methyl-1-(4-sulfamoyl-phenyl)-1H-pyrrole-3-carboxylic Acid (2-dimethylamino-ethyl)-amide The titled compound was obtained according to the procedure described in General Procedure F using N,N-dimethylethane-1,2-diamine. $^1$H NMR (500 MHz, DMSO-d$_6$/D$_2$O) δ ppm 2.27-2.37 (m, 3H) 2.58-2.71 (m, 6H) 2.84-3.05 (m, 2H) 3.44-3.55 (m, 2H) 6.82-6.91 (m, 1H) 6.99-7.06 (m, 2H) 7.23-7.35 (m, 2H) 7.38-7.50 (m, 2H) 7.80-7.96 (m, 2H); MS (ESI: negative ion detection) m/z 459 (M−1).

Example 140

5-(4-chloro-phenyl)-2-methyl-1-(4-sulfamoyl-phenyl)-1H-pyrrole-3-carboxylic Acid-(3-dimethylamino-propyl)-amide The titled compound was obtained according to the procedure described in General Procedure F using $N^1,N^1$-dimethylpropane-1,3-diamine. $^1$H NMR (500 MHz, DMSO-$d_6$/$D_2O$) δ ppm 1.76-1.88 (m, 2H) 2.28-2.36 (m, 3H) 2.68-2.75 (m, 6H) 2.90-3.03 (m, 2H) 3.23-3.31 (m, 2H) 6.82-6.94 (m, 1H) 6.96-7.08 (m, 2H) 7.23-7.33 (m, 2H) 7.39-7.46 (m, 2H) 7.84-7.92 (m, 2H); (ESI) m/z positive ion 475 (M+1).

Example 141

5-(4-chloro-phenyl)-2-methyl-1-(4-sulfamoyl-phenyl)-1H-pyrrole-3-carboxylic Acid-2-hydroxyethyl)-propyl-amide The titled compound was obtained according to the procedure described in General Procedure F using 2-(propylamino)ethanol. $^1$H NMR (500 MHz, DMSO-$d_6$/$D_2O$) δ ppm 0.70-0.96 (m, 3H) 1.40-1.66 (m, 2H) 2.04-2.09 (m, 3H) 3.41-3.46 (m, 2H) 3.46-3.52 (m, 2H) 3.53-3.64 (m, 2H) 6.26-6.75 (m, 1H) 6.97-7.10 (m, 2H) 7.21-7.31 (m, 2H) 7.40-7.48 (m, 2H) 7.83-7.91 (m, 2H); MS (ESI: negative ion detection) m/z 474 (M−1).

Example 142

5-(4-chloro-phenyl)-2-methyl-1-(4-sulfamoyl-phenyl)-1H-pyrrole-3-carboxylic Acid-(3-hydroxy-propyl)-amide The titled compound was obtained according to the procedure described in General Procedure F using 3-aminopropanol. $^1$H NMR (500 MHz, DMSO-$d_6$/$D_2O$) δ ppm 1.55-1.72 (m, 2H) 2.27-2.35 (m, 3H) 3.21-3.30 (m, 2H) 3.42-3.51 (m, 2H) 6.81-6.94 (m, 1H) 6.98-7.06 (m, 2H) 7.22-7.32 (m, 2H) 7.36-7.49 (m, 2H) 7.81-7.93 (m, 2H); MS (ESI: negative ion detection) m/z 446 (M−1).

Example 143

N-acetyl-4-[5-(4-chloro-phenyl)-2-methyl-3-propionyl-pyrrol-1-yl]-benzenesulfonamide To a solution of 4-[5-(4-chloro-phenyl)-2-methyl-3-propionyl-pyrrol-1-yl]-benzenesulfonamide (Example 31, 0.12 g, 0.31 mmol) in dry THF (5 mL) was added triethylamine (0.4 mmol, 0.06 mL) and DMAP (0.031 mmol, 4 mg) at room temperature. 10 Minutes later acetic anhydride (0.62 mmol, 0.06 mL) was added drop wise and the mixture stirred at room temperature for 16 hours. The mixture was diluted with ethyl acetate (100 mL), washed with sodium bicarbonate (saturated solution, 50 mL), water (50 mL) and brine (50 mL). The organic phase was dried over sodium sulfate, filtered and evaporated under reduced pressure. The residue was purified over silica using $CH_2Cl_2$:MeOH (95:5) as eluant to provide the titled compound. $^1$H NMR (CDCl$_3$) δ ppm 1.18 (3H), 2.05 (3H), 2.16 (3H), 2.45 (2H), 3.39 (2H), 6.90 (1H), 7.33-7.90 (8H), 8.50 (1H); MS (ESI) m/z 445 (M+H).

Example 144

N-acetyl-4-[5-(4-chloro-phenyl)-2-methyl-3-propionyl-pyrrol-1-yl]-benzenesulfonamide-N-sodium Salt A mixture of Example 143 (0.1 g, 0.22 mmol) in 5 mL of absolute ethanol and 2 mL of water was treated with aqueous sodium hydroxide (5 M, 0.22 mmol, 0.04 mL) with stirring at room temperature. After 45 minutes, the solution was concentrated in vacuo to provide the titled compound. Anal Calc'd for $C_{22}H_{20}ClN_2NaO_4S$: C, 56.59, H, 4.32; N, 6.00. Found C, 56.61; H, 4.33; N, 5.88.

Example 145

4-[5-(4-chloro-phenyl)-2-methyl-3-propionyl-pyrrol-1-yl]-N-propionyl-benzenesulfonamide The titled compound was obtained according to the procedure described in Example 143 substituting propionic anhydride for acetic anhydride. $^1$H NMR (CDCl$_3$) δ ppm 1.15 (3H), 1.20 (3H), 2.16 (3H), 2.20 (2H), 2.44 (2H), 3.39 (2H), 6.95 (1H), 7.33-7.90 (8H), 8.70 (1H); MS (ESI) m/z 459 (M+H).

Example 146

4-[5-(4-chloro-phenyl)-2-methyl-3-propionyl-pyrrol-1-yl]-N-propionyl-benzenesulfonamide-N-sodium Salt The titled compound was obtained according to the procedure described in Example 144 substituting Example 145 for Example 143. Anal Calc'd for $C_{23}H_{22}ClN_2NaO_4S$: C, 57.44, H, 4.61; N, 5.82. Found C, 57.39; H, 4.71; N, 5.95.

Determination of Biological Activity

To determine the effectiveness of compounds of formula (I) or (II), as allosteric modulators, the compounds of the invention were evaluated according to two high-throughput functional assays using (i) IMR-32 cells endogenous expressing α7 nAChRs and measuring $Ca^{2+}$ flux or membrane potential changes utilizing the fluorescence-imaging plate reader (FLIPR)-based assays and (ii) measurement of phospho-ERK activity using western blot assays. These assays allow for higher throughput screening of positive allosteric modulators using cells or cell lines expressing endogenous α7 nAChRs.

(i) High-Throughput Calcium Flux Assays Using Cells Expressing Endogenous α7 nAChRs Since allosteric modulators affect the kinetics of channel function and thus affect calcium dynamics, it is demonstrated that novel modulators can be identified when assays are conducted in the presence of a selective agonist, and conversely, novel agonists can be identified when screened or tested in the presence an allosteric modulator. As such, positive allosteric modulators can be identified or nicotinic acetylcholine receptor agonists can be identified by using IMR-32 cells that endogenously express various nicotinic receptors including α7 nAChRs. It is contemplated that such assay can be utilized with a number of cell lines conventionally not amenable to α7 nicotinic compound screening. Accordingly, allosteric modulator compounds described herein can be identified using fluorescence-based throughput functional assay using cell lines such as IMR-32 neuroblastoma or primary dissociated neurons. Although cell types such as IMR-32 neuroblastoma and neurons are known to contain several nicotinic receptor subunits, α7 selective agonists in the present assay selectively stimulate calcium responses only in presence of positive allosteric modulators. Any suitable selective α7 agonist can be used. Selective α7 agonists from a range of structural types may be used such as those described in the literature including PNU-282987, SSR180711A and AR-R17779 and others described in earlier patent applications, such as 2-methyl-5-(6-phenyl-pyridazin-3-yl)-octahydro-pyrrolo[3,4-c]pyrrole (published in US 20050065178); 5-[6-(5-methyl-hexahydro-pyrrolo[3,4-c]pyrrol-2-yl)-pyridazin-3-yl]-1H-indole (published in US 20050065178), 3-[6-(1H-indol-5-yl)-pyradazin-3-yloxy]-1-aza-bicyclo[2.2.2]octane (published in US 2005/0137204 and US 2005/0245531); and 4-(5-phenyl-[1,3,4] oxadiazol-2-yl)-1,4-diaza-bicyclo[3.2.2]nonane (published in WO 2004/029053).

IMR-32 neuroblastoma cells (ATCC) were grown to confluency in 162 cm$^2$ tissue culture flasks in minimum essential media supplemented with 10% FBS and 1 mM sodium puruvate, 0.1 mM non-essential amino acids and 1% antibiotic-antimycotic. The cells were then dissociated using cell dissociation buffer and 40 µl of 3.5×10$^5$ cells/ml cell suspension was plated (~15,000 cells/well) into black plates with clear bottom and maintained for 48 hours in a tissue culture incubator at 37° C. under an atmosphere of 5% $CO_2$: 95% air. Other clonal cell lines or dissociated primary cortical neurons that express endogenous α7 nicotinic receptors may also be used in this assay. Calcium flux was measured using calcium-3 assay kit (Molecular Devices, Sunnyvale, Calif.) or fluo-4. A stock solution of the dye was prepared by dissolving each vial supplied by the vendor in Hank's balanced salt solution buffer (HBSS) containing 20 mM HEPES. The stock solution was diluted 1:20 using the same buffer before use. The growth media was removed from the cells and loaded with 45 µl of the dye and incubated at room temperature for three hours. Fluorescence measurements were read simultaneously from all the wells by a Fluorometic Imaging Plate Reader (FLIPR) at an excitation wavelength of 480 nm and an emission wavelength of 520 nm. Baseline fluorescence was measured for the first 10 seconds, at which point 5× concentrations of modulator/test compounds were added to the cell plate and incubated for three minutes. The fluorescence intensity was captured every second for the first 1 minute followed by every 5 seconds for an additional 2 minutes. This procedure was followed by 20 µl of 4× concentration of agonist and readings were taken for a period of three minutes as described above. Data was normalized to maximal responses and plotted as a function of concentration. The concentration dependence of changes fluorescence responses was fitted by non-linear regression analysis (GraphPad Prism, San Diego, Calif.) to obtain $EC_{50}$ values. Neither agonist alone nor modulator alone would evoke responses. However, in presence of an allosteric modulator, agonist elicited concentration dependent increase in calcium response and likewise in presence of a α7 selective agonist, modulator responses were revealed. The α7 selective antagonist, methyllycaconitine, abolished response demonstrating that the effects are mediated via the α7 receptor.

As shown in FIG. 1, positive allosteric modulators were identified by measuring fluorescence changes to intracellular calcium in a fluorimetric plate reader in the presence of selective α7 nAChR agonists using cells natively expressing α7 nAChRs. In FIG. 1, a compound with positive allosteric modulator activity (example 31) evoked calcium fluorescence response in IMR-32 neuroblastoma cell line, a cell line that expresses endogenous α7 nAChRs. Agonist alone or modulator alone did not evoke a calcium response. However, when an agonist and a modulator were co-applied together, calcium responses were triggered. To obtain the data represented in FIG. 1, 2-methyl-5-(6-phenyl-pyridazin-3-yl)-octahydro-pyrrolo[3,4-c]pyrrole (published in US 20050065178) was used as an agonist in the absence or presence of 5 µM of a compound in Example 31. Other α7 nicotinic receptor agonists including 5-[6-(5-Methyl-hexahydro-pyrrolo[3,4-c]pyrrol-2-yl)-pyridazin-3-yl]-1H-indole (published in US 20050065178); 4-(5-phenyl-[1,3,4]oxadiazol-2-yl)-1,4-diaza-bicyclo[3.2.2]nonane (published in WO 2004/029053); various quinuclidine derivatives (published in US 2005/0137204 and US 2005/0245531); and PNU-282987 (Hajos et al., J Pharmacol. Exp Ther., 312: 1213-22, 2005) also are suitable for the assay. Likewise, primary neurons and other clonal cell lines that express α7 nAChRs also may be used. Other fluorescence measurements, such as those monitoring changes in membrane potential, also are suitable for the assay.

Figure 2:
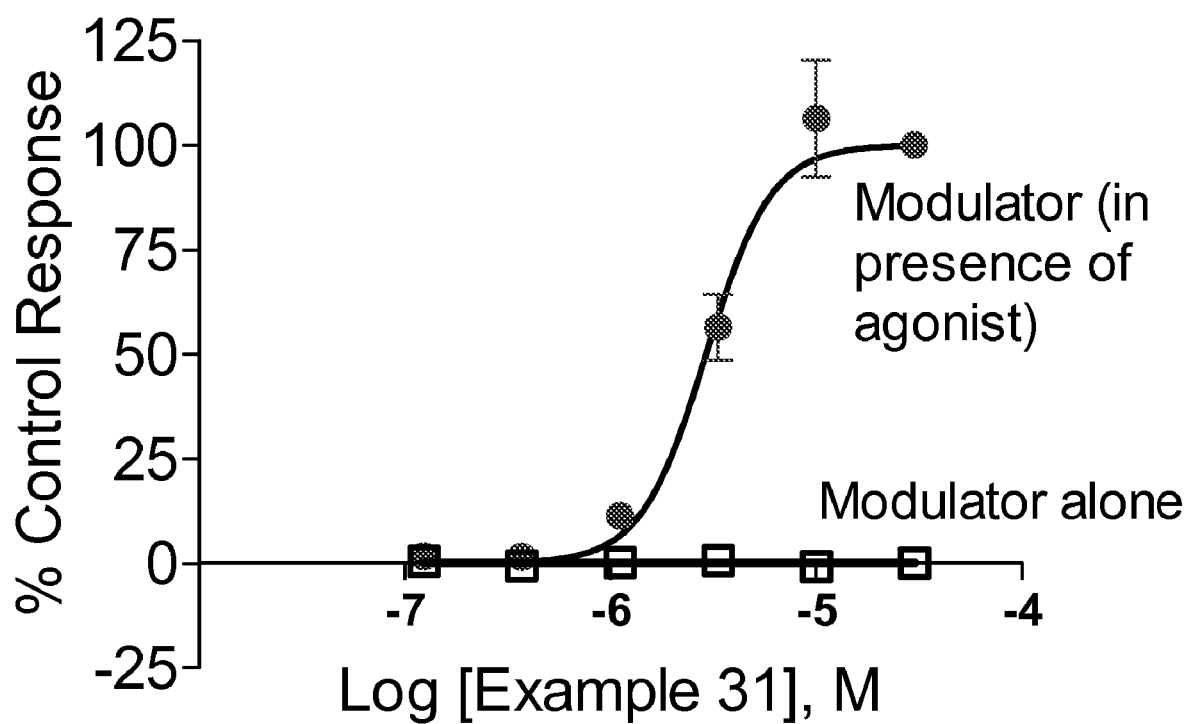
FIG. 2 is a graphical representation of a concentration response curve wherein control response measured in percentages is represented as a function of the log of the concentration of the positive allosteric modulator. The data were obtained by assaying a compound, Example 31, in the presence or absence of selective α7 nAChR agonists in cells natively expressing α7 nAChRs.

A concentration response curve of the α7 nAChR positive allosteric modulator also can be useful for characterizing the activity of a nAChR compound. To obtain data represented in FIG. 2, the compound of Example 31 was allowed to interact with the IMR-32 cell line in the presence of, or absence of, a selective α7 nAChR agonist. Modulator alone did not trigger calcium responses. However, when combined with the selective α7 nAChR agonist, fluorescence responses were evoked in a concentration-dependent manner. In FIG. 2, the Y-axis represents the normalized change in fluorescence and the X-axis represents increasing concentrations of the modulator. Typical $EC_{50}$ values for positive allosteric modulator compounds derived in this assay range from about 10 nM to about 30 µM. In the example above, 4-(5-phenyl-[1,3,4]oxadiazol-2-yl)-1,4-diaza-bicyclo[3.2.2]nonane (published in WO 2004/029053) was used as the agonist. The $EC_{50}$ value of example 31 was determined to be 2.9 µM. Other α7 nicotinic receptor agonists including-methyl-5-(6-phenyl-pyridazin-3-yl)-octahydro-pyrrolo[3,4-c]pyrrole (published in US 20050065178), 5-[6-(5-methyl-hexahydro-pyrrolo[3,4-c] pyrrol-2yl)-pyridazin-3-yl]-1H-indole (published in US 20050065178), various quinuclidine derivatives (published in US 2005/0137204 and US 2005/0245531), and PNU-282987 (Hajos et al., J Pharmacol. Exp. Ther. 2005; 312: 1213-22) also are suitable.

Figure 3:
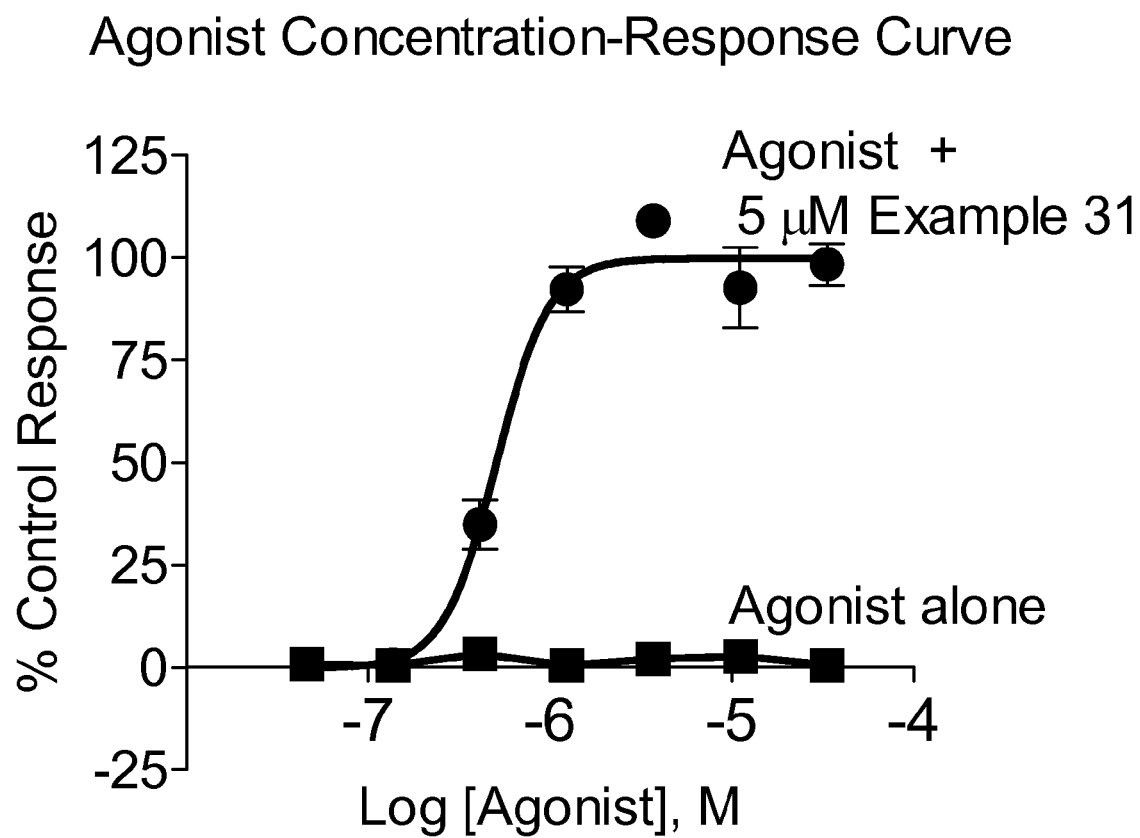
FIG. 3 is a graphical representation of a concentration response curve wherein control response measured in percentages is represented as a function of the log of the concentration of the agonist. The data were obtained by assaying a compound, Example 31, in the presence or absence of selective α7 nAChR agonists in cells natively expressing α7 nAChRs, for example the IMR-32 cell line.

The concentration response curve of α7 nAChR agonist also can be useful for characterizing the activity of a α7 positive allosteric modulator. In FIG. 3, concentration response curves to α7 nAChR agonist in the presence of allosteric modulator (example 31) or in its absence are shown. Agonist alone did not trigger calcium responses. However, when combined with a selective α7 nAChR modulator, such as a compound of Example 31, fluorescence responses were evoked in a concentration-dependent manner. In FIG. 3, the Y-axis represents the normalized change in fluorescence and the X-axis represents increasing concentrations of the agonist. The fixed concentration of the allosteric modulator was 5 µM. The $EC_{50}$ values for an α7 nAChR agonist identified in this assay can typically range from 1 nM to 30 µM. To obtain the data for FIG. 3, 2-methyl-5-(6-phenyl-pyridazin-3-yl)-octahydro-pyrrolo[3,4-c]pyrrole (published in US 20050065178) was used as the agonist and was determined to have an $EC_{50}$ value of 507 nM. Other α7 nicotinic receptor agonists including 5-[6-(5-methyl-hexahydro-pyrrolo[3,4-c] pyrrol-2yl)-pyridazin-3-yl]-1H-indole (published in US 20050065178), 4-(5-phenyl-[1,3,4]oxadiazol-2-yl)-1,4- diaza-bicyclo[3.2.2]nonane (published in WO 2004/029053), various quinuclidine derivatives (published in US 2005/0137204 and US 2005/0245531), and PNU-282987 (Hajos et al., J Pharmacol. Exp. Ther. 2005; 312: 1213-22) also are suitable for the assay.

(ii) High-Throughput Phospho-ERK Assays Using Cells Expressing Endogenous α7 nAChRs Rat pheochromocytoma (PC-12) cells (ATCC, Manassas, Va.) were cultured and maintained in F-12K media supplemented with 15% horse serum, 2.5% fetal calf serum, and 2 mM L-Glutamine in poly-D lysine coated dishes at 37° C. and 5% $CO_2$. Cells were plated in black-walled clear bottom 96-well Biocoat™ plates coated with poly-D-lysine (BD Biosciences, Bedford, Mass.) and grown for 2-3 days. Afterward, the culture media is replaced with serum-free media to starve cells overnight. On the day of the assay, cell media was removed and cells (60-80% confluent) were treated with agonist and/or modulator in Dulbecco's phosphate buffer saline (D-PBS) (with $Ca^{2+}$, $Mg^{2+}$, and 1 mg/ml D-glucose), as indicated in the result section.

PC-12 cells are treated for 10 minutes at 37° C. with test positive allosteric modulator compounds and then challenged with a selective α7 agonist for 5 minutes at 37° C. in a final volume of 100 μl/well, unless otherwise indicated. After treatment, media was discarded and adherent cells were immediately fixed in the presence of 150 μl/well of 3.7% formaldehyde/phosphate-buffered saline for 30-60 minutes at room temperature. Cells were then washed (4 times/5 minutes) and permeabilized with 200 μl/well of 0.1% Triton X-100/PBS. Permeabilized cells were blocked using the Odyssey blocking buffer (100 μl/well) and plates were rocked overnight at 4° C. Both anti-total ERK (rabbit) and anti-phospho ERK (mouse) antibodies were diluted to 1/1000 and 1/500, respectively, in Odyssey blocking buffer and added together at 50 μl/well for 2-3 hours at room temperature. Polyclonal rabbit anti-ERK1/2 and monoclonal mouse anti-phospho-ERK 1/2 were purchased from Sigma-Aldrich (St. Louis, Mo.). The plates were washed 4 times with 0.1% Tween 20/PBS (200 ul/well), and incubated with secondary antibodies (1/1000 dilution) in blocking buffer supplemented with 0.2% Tween for 1 hour. Alexa Fluor 680-labeled goat anti-rabbit antibodies were added to recognize total ERK labeling (red color) and IRDye800-labeled donkey anti-mouse antibodies were added to recognize phospho-ERK labeling (green color). Alexa Fluor 680-labeled goat-anti-rabbit antibodies were obtained from Molecular Probes (Eugene, Oreg.). IRDye 800CW-labeled Donkey-anti-mouse antibodies were purchased from Rockland (Gilbertsville, Pa.). The plates were washed 4 times with 0.2% Tween and 0.01% SDS/PBS and scanned using the Odyssey infrared scanner. Well intensities were quantitated and phospho-ERK signals were normalized to total ERK signals by the Odyssey software. Data analysis was performed using GraphPad Prism (GraphPad Software, San Diego, Calif.).

Figure 4:
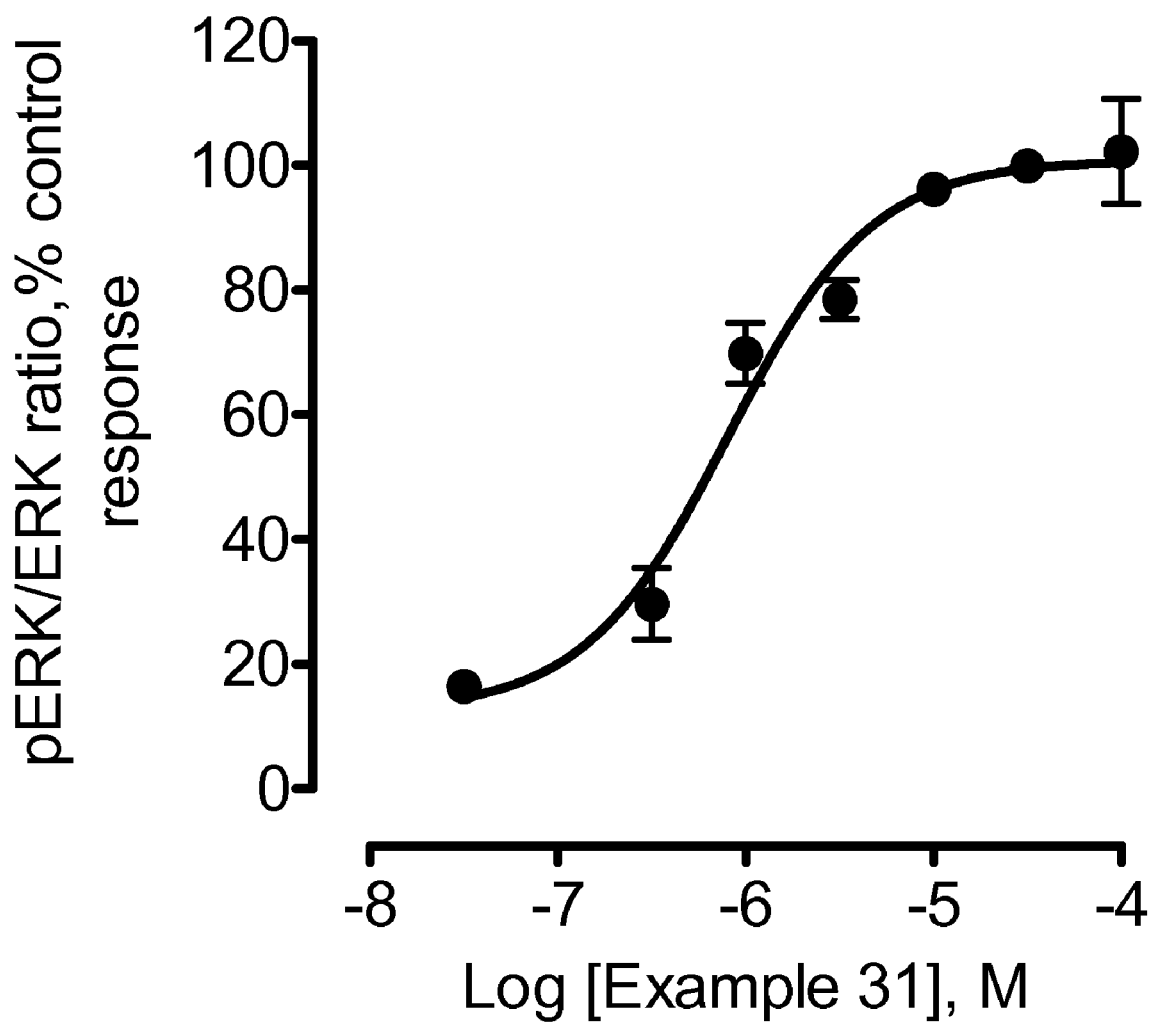
FIG. 4 is a graphical representation of phosphorylation of extracellular receptor kinase (ERK) represented as a function of the log of the concentration of a positive allosteric modulator. The data were obtained by assaying a compound, Example 31, in the presence of selective α7 nAChR agonists in cells natively expressing α7 nAChRs, for example PC-12 cells.

Positive allosteric modulators can be also identified by measuring changes in the phosphorylation of ERK (extracellular receptor kinase) by in-cell western analysis. To obtain the data represented in FIG. 4, a positive allosteric modulator increases ERK phosphorylation in rat pheochromocytoma PC-12 cells in the presence of selective α7 agonists. The assay identified positive allosteric modulators in cells expressing endogenous α7 nAChRs without the need for overexpressing recombinant receptors. FIG. 4 represents a concentration-response relationship wherein the Y-axis is the normalized change in phospho-ERK to total ERK ratio and the X-axis represents increasing concentrations of the allosteric modulator. Compounds with allosteric modulator activity, such as example 31 (shown in FIG. 1), evoked concentration-dependent increases in ERK phosphorylation. The $EC_{50}$ values for positive allosteric modulator compounds derived in this assay typically range from about 10 nM to about 30 μM. In the example above, PNU-282987 (Hajos et al., J Pharmacol. Exp. Ther. 2005; 312: 1213-22) is used as the α7 selective agonist. The $EC_{50}$ value of the compound of Example 31 was determined to be about 2.9 μM. Other α7 nicotinic receptor agonists including 2-methyl-5-(6-phenyl-pyridazin-3-yl)-octahydro-pyrrolo[3,4-c]pyrrole (published in US 20050065178); 5-[6-(5-methyl-hexahydro-pyrrolo[3,4-c]pyrrol-2-yl)-pyridazin-3-yl]-1H-indole and other analogs (published in US 20050065178); various quinuclidine derivatives (published in US 2005/0137204 and US 2005/0245531); 4-(5-phenyl-[1,3,4]oxadiazol-2-yl)-1,4-diaza-bicyclo[3.2.2]nonane (published in WO 2004/029053); and other related compounds also are suitable for the assay.

Compounds of the invention are positive allosteric modulators of α7 nAChR that can enhance the effects of naturally occurring neurotransmitter, acetylcholine or exogenous administered agonist. Although not being limited by theory, positive allosteric modulators generally amplify agonist (acetylcholine) responses by (i) attenuating receptor desensitization so that the receptor remains open for longer duration and/or (ii) by directly amplifying the efficacy of ACh by enhancing maximal receptor activation. In either case, such compounds typically boost endogenous transmission of acetylcholine, and can do so in a temporally and spatially restricted manner since these effects will be localized to regions where the α7 receptors are expressed. Allosteric modulator compounds can modulate function of α7 nAChRs by enhancing ion channel function as measured by calcium responses or ERK phosphorylation described herein, or other approaches such as current or membrane potential studies. Preferred compounds are those that behave as positive allosteric modulators in these assays between concentration range of about 0.1 nM to about 30 μM. Allosteric modulation of the α7 receptor can trigger key signaling processes that are important to effects on memory, cytoprotection, gene transcription and disease modification. Therefore, the administration of a therapeutically effective amount of a compound of formula (I) to a mammal provides a method of selectively modulating the effects of α7 nAChRs.

It is understood that the foregoing detailed description and accompanying examples are merely illustrative and are not to be taken as limitations upon the scope of the invention, which is defined solely by the appended claims and their equivalents. Various changes and modifications to the disclosed embodiments will be apparent to those skilled in the art. Such changes and modifications, including without limitation those relating to the chemical structures, substituents, derivatives, intermediates, syntheses, formulations and/or methods of use of the invention, may be made without departing from the spirit and scope thereof.

What is claimed is:

1. A compound of the formula (I):

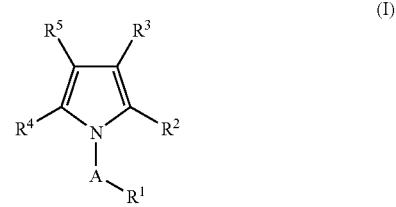

or a pharmaceutically acceptable salt, ester, amide thereof, wherein:

A is a 6-membered aryl ring;
$R^1$ is —$SO_2R^{10}$;
$R^2$ is hydrogen or alkyl;

R³ is —C(O)R¹²;

R⁴ is aryl substituted with 0, 1, 2, 3, 4, or 5 substituents independently elected from acyl, acyloxy, alkenyl, alkoxyalkoxy, alkoxyalkyl, alkoxycarbonyl, alkoxyimino, alkoxysulfonyl, alkyl, alkylcarbonyl, alkylsulfonyl, alkynyl, amino, carboxy, cyano, cyanoalkyl, formyl, haloalkoxy, haloalkyl, halo, hydroxy, hydroxyalkyl, mercapto, nitro, thioalkoxy, —NR$_A$R$_B$, (NR$_A$R$_B$)alkyl, (NR$_A$R$_B$)alkoxy, (NR$_A$R$_B$)carbonyl, and (NR$_A$R$_B$)sulfonyl, wherein R$_A$ and R$_B$ are independently selected from hydrogen, alkyl, alkylcarbonyl, alkylsulfonyl, and formyl, or —R¹⁴R¹⁵;

R⁵ is hydrogen, halo, aryl, heteroaryl, bicyclic heteroaryl, —R²³—R²⁴, or —R²³—C(O)—R²⁴;

R¹⁰ is NR¹¹ᵃR¹¹ᵇ;

R¹¹ᵃ and R¹¹ᵇ are independently hydrogen or alkyl; or R¹¹ᵃ and R¹¹ᵇ taken together with the nitrogen atom to which each is attached form a 4-, 5-, or 6-membered heterocycle;

R¹² is hydrogen, alkyl, heterocycle, heteroarylalkyl, or —NR¹⁶R¹⁷,

R¹⁴ is aryl;

R¹⁵ is aryl, heteroaryl, heterocycle or

R¹⁶ and R¹⁷ are independently hydrogen, alkyl, alkoxy, alkoxyalkyl, aryl, arylalkyl, cycloalkyl, heteroaryl, heteroarylalkyl, heterocycle, heterocyclealkyl, hydroxyalkyl or R¹⁸R¹⁹N-alkyl-;

R¹⁸ and R¹⁹ are independently hydrogen or alkyl;

R²¹ is aryl or heteroaryl;

R²² is arylalkyl;

R²³ is aryl; and

R²⁴ is heteroaryl or heterocycle.

2. The compound of claim 1, wherein
A is phenyl; and
R² is alkyl.

3. The compound of claim 1, wherein
A is phenyl; and
R² is methyl.

4. The compound of claim 1, wherein
A is phenyl;
R² is methyl; and
R¹ is —SO₂NH₂.

5. The compound of claim 1, wherein
A is phenyl;
R² is methyl;
R¹ is —SO₂NH₂;
R⁴ is aryl, wherein aryl is optionally substituted with 1, 2, or 3 selected from the group consisting of alkyl, alkylcarbonyl, alkylsulfonyl, cyano, halo, haloalkyl, nitro, —NR$_A$R$_B$, wherein R$_A$ and R$_B$ are independently hydrogen, alkyl, alkylcarbonyl and alkylsulfonyl.

6. A pharmaceutical composition comprising a compound of claim 1 and a pharmaceutically acceptable carrier.

7. The compound of claim 1, wherein the compound is selected from the group consisting of:

5-(4-chloro-phenyl)-1-[4-(dimethylaminomethylene-sulfamoyl)-phenyl]-2-methyl-1H-pyrrole-3-carboxylic acid N-methoxy-N-methyl amide;
4-[5-(4-chloro-phenyl)-2-methyl-3-propionyl-pyrrol-1yl]-benzenesulfonamide;
4-[5-(4-chloro-phenyl)-3-isobutyryl-2-methyl-pyrrol-1yl]-benzenesulfonamide;
4-[5-(4-chloro-phenyl)-3-cyclopropanecarbonyl-2-methyl-pyrrol-1yl]-benzenesulfonamide;
5-(4-chloro-phenyl)-1-(3-methanesulfonyl-phenyl)-2-methyl-1H-pyrrole-3-carboxylic acid;
5-(4-chloro-phenyl)-1-(3-methanesulfonyl-phenyl)-2-methyl-1H-pyrrole-3-carboxylic acid methoxy-methyl amide;
1-[5-(4-chloro-phenyl)-1-(3-methanesulfonyl-phenyl)-2-methyl-1H-pyrrol-3-yl]propan-1-one;
5-(4-chloro-phenyl)-1-(4-methanesulfonyl-phenyl)-2-methyl-1H-pyrrole-3-carboxaldehyde;
4-[5-(4-chloro-phenyl)-3-(4-hydroxymethyl-phenyl)-2-methyl-pyrrol-1yl]-benzenesulfonamide;
4-[3-benzofuran-2-yl-5-(4-chloro-phenyl)-2-methyl-pyrrol-1-yl]-benzenesulfonamide;
5-(4-chloro-phenyl)-2-methyl-1-(4-sulfamoyl-phenyl)-1H-pyrrole-3-carboxylic acid isopropylamide;
5-(4-chloro-phenyl)-2-methyl-1-(4-sulfamoyl-phenyl)-1H-pyrrole-3-carboxylic acid butylamide;
5-(4-chloro-phenyl)-2-methyl-1-(4-sulfamoyl-phenyl)-1H-pyrrole-3-carboxylic acid (2-methoxy-ethyl)-amide;
5-(4-chloro-phenyl)-2-methyl-1-(4-sulfamoyl-phenyl)-1H-pyrrole-3-carboxylic acid-(3-prop oxy-propyl)-amide;
5-(4-chloro-phenyl)-2-methyl-1-(4-sulfamoyl-phenyl)-1H-pyrrole-3-carboxylic acid-(R)-(tetrahydro-furan-2-ylmethyl)-amide;
5-(4-chloro-phenyl)-2-methyl-1-(4-sulfamoyl-phenyl)-1H-pyrrole-3-carboxylic acid (tetrahydro-furan-3-ylmethyl)-amide;
5-(4-chloro-phenyl)-2-methyl-1-(4-sulfamoyl-phenyl)-1H-pyrrole-3-carboxylic acid cyclobutylamide;
5-(4-chloro-phenyl)-2-methyl-1-(4-sulfamoyl-phenyl)-1H-pyrrole-3-carboxylic acid dimethylamide;
5-(4-chloro-phenyl)-2-methyl-1-(4-sulfamoyl-phenyl)-1H-pyrrole-3-carboxylic acid ethyl-methyl-amide;
5-(4-chloro-phenyl)-2-methyl-1-(4-sulfamoyl-phenyl)-1H-pyrrole-3-carboxylic acid isopropyl-methyl-amide;
4-[5-(4-chloro-phenyl)-2-methyl-3-(pyrrolidine-1-carbonyl)-pyrrol-1yl]-benzenesulfonamide;
4-[5-(4-chloro-phenyl)-2-methyl-3-(piperidine-1-carbonyl)-pyrrol-1yl]-benzenesulfonamide;
5-(4-chloro-phenyl)-2-methyl-1-(4-sulfamoyl-phenyl)-1H-pyrrole-3-carboxylic acid-(2-methoxy-ethyl)-methyl-amide;
5-(4-chloro-phenyl)-2-methyl-1-(4-sulfamoyl-phenyl)-1H-pyrrole-3-carboxylic acid-bis-(2-methoxy-ethyl)-amide;
4-[5-(4-chloro-phenyl)-2-methyl-3-(morpholine-4-carbonyl)-pyrrol-1yl]-benzenesulfonamide;
5-(4-chloro-phenyl)-2-methyl-1-(4-sulfamoyl-phenyl)-1H-pyrrole-3-carboxylic acid benzylamide;
5-(4-chloro-phenyl)-2-methyl-1-(4-sulfamoyl-phenyl)-1H-pyrrole-3-carboxylic acid (pyridin-3-ylmethyl)-amide;
5-(4-chloro-phenyl)-2-methyl-1-(4-sulfamoyl-phenyl)-1H-pyrrole-3-carboxylic acid (2-dimethylamino-ethyl)-amide;
5-(4-chloro-phenyl)-2-methyl-1-(4-sulfamoyl-phenyl)-1H-pyrrole-3-carboxylic acid-(3-dimethylamino-propyl)-amide;
5-(4-chloro-phenyl)-2-methyl-1-(4-sulfamoyl-phenyl)-1H-pyrrole-3-carboxylic acid-(2-hydroxy-ethyl)-propyl-amide;
5-(4-chloro-phenyl)-2-methyl-1-(4-sulfamoyl-phenyl)-1H-pyrrole-3-carboxylic acid-(3-hydroxy-propyl)-amide;
N-acetyl-4-[5-(4-chloro-phenyl)-2-methyl-3-propionyl-pyrrol-1-yl]-benzenesulfonamide;

N-acetyl-4-[5-(4-chloro-phenyl)-2-methyl-3-propionyl-pyrrol-1-yl]-benzenesulfonamide-N-sodium salt;
4-[5-(4-chloro-phenyl)-2-methyl-3-propionyl-pyrrol-1yl]-N-propionyl-benzenesulfonamide; and
4-[5-(4-chloro-phenyl)-2-methyl-3-propionyl-pyrrol-1yl]-N-propionyl-benzenesulfonamide-N-sodium salt.

* * * * *

UNITED STATES PATENT AND TRADEMARK OFFICE
CERTIFICATE OF CORRECTION

PATENT NO. : 7,741,364 B2
APPLICATION NO. : 11/769395
DATED : June 22, 2010
INVENTOR(S) : Ramin Faghih et al.

It is certified that error appears in the above-identified patent and that said Letters Patent is hereby corrected as shown below:

Column 73, Line 23
"heterocycle or" should read --heterocycle or $-R^{21}$ $-R^{22}$;--

Column 73, Lines 66-67
delete "5-(4-chloro-phenyl)-1-(3-methanesulfonyl-phenyl)-2-methyl-1H—pyrrole-3-carboxylic acid;"

Signed and Sealed this
First Day of February, 2011

David J. Kappos
*Director of the United States Patent and Trademark Office*